(12) United States Patent
Gage et al.

(10) Patent No.: US 12,612,662 B2
(45) Date of Patent: Apr. 28, 2026

(54) DNA REPAIR SITE DETECTION FOR PERSONAL GENOMICS, EPIGENOMICS, AND GENE THERAPY

(71) Applicant: SALK INSTITUTE FOR BIOLOGICAL STUDIES, La Jolla, CA (US)

(72) Inventors: Fred H. Gage, La Jolla, CA (US); Dylan A. Reid, San Diego, CA (US); Patrick J. Reed, San Diego, CA (US)

(73) Assignee: SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 762 days.

(21) Appl. No.: 17/913,352

(22) PCT Filed: Jun. 15, 2020

(86) PCT No.: PCT/US2020/037757
§ 371 (c)(1),
(2) Date: Sep. 21, 2022

(87) PCT Pub. No.: WO2021/194531
PCT Pub. Date: Sep. 30, 2021

(65) Prior Publication Data
US 2023/0111083 A1 Apr. 13, 2023

Related U.S. Application Data

(60) Provisional application No. 62/993,499, filed on Mar. 23, 2020.

(51) Int. Cl.
*C12Q 1/6883* (2018.01)
*C12Q 1/6806* (2018.01)
*C12Q 1/6869* (2018.01)

(52) U.S. Cl.
CPC ......... *C12Q 1/6883* (2013.01); *C12Q 1/6806* (2013.01); *C12Q 1/6869* (2013.01)

(58) Field of Classification Search
CPC .. C12Q 1/6883; C12Q 1/6806; C12Q 1/6869; C12Q 1/6886; C12Q 2600/156; G16H 50/20; Y02A 90/10; G16B 20/20; G16B 30/10
See application file for complete search history.

(56) References Cited

U.S. PATENT DOCUMENTS

| | | | |
|---|---|---|---|
| 8,377,640 B2 | 2/2013 | Nagy | |
| 10,280,451 B2 | 5/2019 | Berman et al. | |
| 2012/0076871 A1* | 3/2012 | Cinque | A61K 33/242 435/6.19 |
| 2021/0008161 A1* | 1/2021 | D'Souza | A61K 38/1709 |

FOREIGN PATENT DOCUMENTS

WO WO 2019/094984 A1 5/2019

OTHER PUBLICATIONS

Georgieva et al., "Detection of Base Analogs Incorporated During DNA Replication by Nanopore Sequencing," *Nucleic Acids Research*, 48(15):1-12 (2020).
Reid et al., "Incorporation of a nucleoside analog maps genome repair sites in postmitotic human neurons," *Science* 372:91-94, 2021.
International Search Report and Written Opinion for International Application No. PCT/US2020/037757, dated Sep. 25, 2020 (10 pages).
Shanbhag et al., "Early Neuronal Accumulation of DNA Double Strands Breaks in Alzheimer's Disease," *Acta Neuropathological Communications*, 7:77, pp. 1-18 (May 17, 2019).
Wang et al., "Increased Neural Progenitor Proliferation in a hiPSC Model of Autism Induces Replication Stress-Associated Genome Instability," *Cell Stem Cell* 26:221-233 (Feb. 6, 2020).

* cited by examiner

*Primary Examiner* — Cynthia B Wilder

(74) *Attorney, Agent, or Firm* — KLARQUIST SPARKMAN, LLP

(57) ABSTRACT
Provided are methods for identification of DNA repair locations in a genome of a non-dividing cell, by incorporating a reactive nucleoside analogs into the genome of the non-dividing cell, then sequencing the regions of the genome that incorporated the nucleoside analog.

20 Claims, 37 Drawing Sheets

Input

DNA Repair 0 kb

*XRCC5*

100 kb

Input

DNA Repair 0 kb

*DLG2*

2,225 kb

Human neuron DNA repair peaks
(ATAC & H3K27Ac Bkgr)

| Motif | p-value | Targ/Bkgr | Best match |
|---|---|---|---|
| ATTGAT I | 1.6e-1061 | 3.531 | HNF6 |
| ACG | 2.7e-458 | 1.721 | ATF3 |
| AGAAA | 2e-370 | 1.480 | NFAT5 |
| TA T A | 5.2e-255 | 1.382 | FOXB1 |
| C G G | 2.9e-246 | 1.193 | UBP1 |
| CA G | 4.9e-120 | 1.184 | ZNF563 |
| TGACTCA AGAAA | 4.7e-80 | 2.575 | JUN |
| AGAAA | 5.1e-76 | 1.172 | ZFP28 |
| CCCT G G | 3.6e-62 | 1.283 | COE1 |

DNA Repair

ATAC

H3K27Ac 0 kb    50 kb

CD3EAP  ERCC1 log₂(Repair Reads)

0 2 4 6 8 log₂(H3K27Ac Reads)

10.0    1.0    0.1 log₂(ATAC Reads)

0.1    1.0    10.0

- Repair
+ Repair

ATAC    H3K27Ac log₂(Reads)

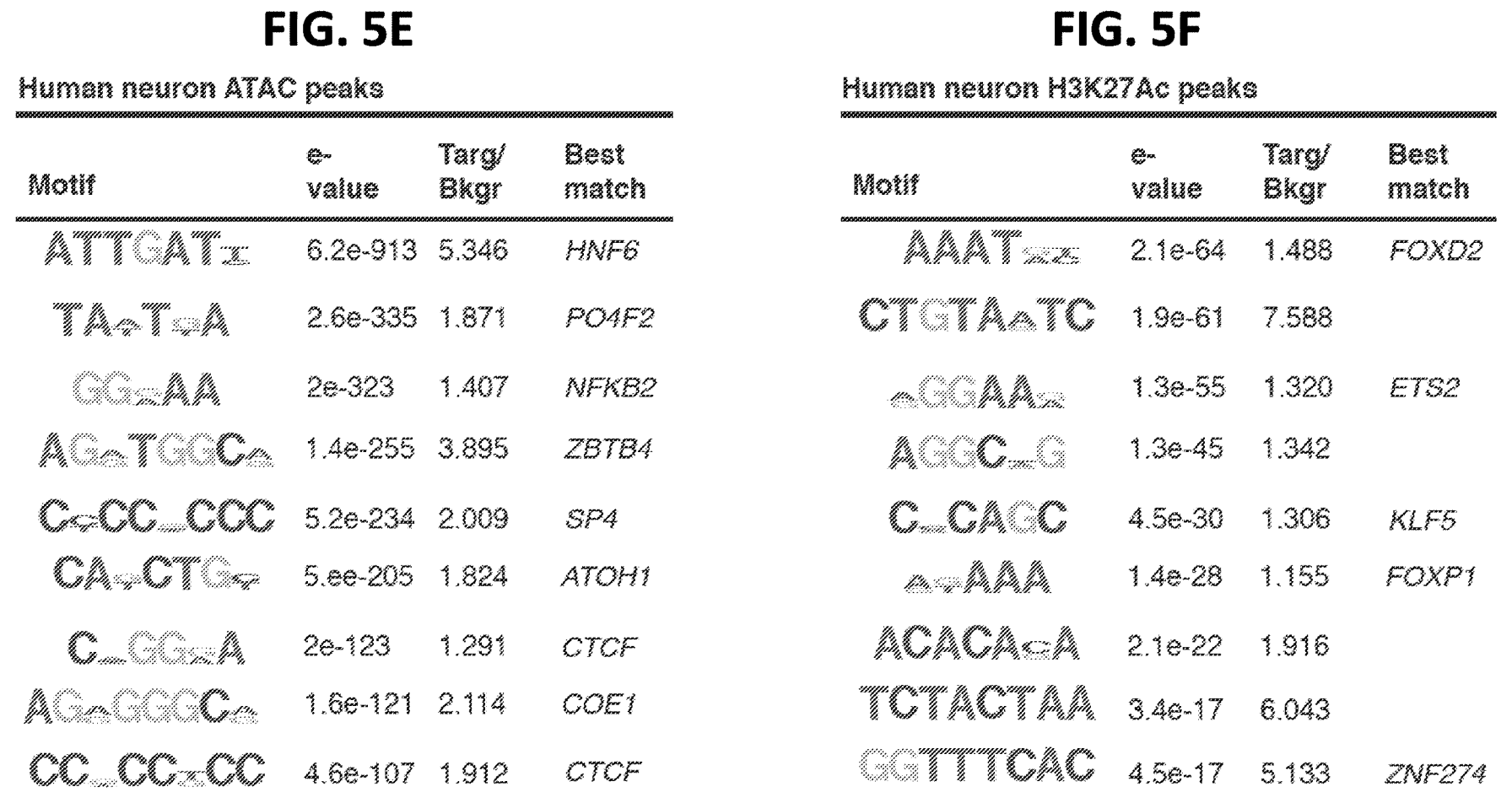

Human neuron H3K27Ac peaks

| Motif | e-value | Targ/Bkgr | Best match |
|---|---|---|---|
| AAAT___ | 2.1e-64 | 1.488 | FOXD2 |
| CTGTAAATC | 1.9e-61 | 7.588 | |
| _GGAA__ | 1.3e-55 | 1.320 | ETS2 |
| ACGC_G | 1.3e-45 | 1.342 | |
| C__CAGC | 4.5e-30 | 1.306 | KLF5 |
| __AAA | 1.4e-28 | 1.155 | FOXP1 |
| ACACA__A | 2.1e-22 | 1.916 | |
| TCTACTAA | 3.4e-17 | 6.043 | |
| GGTTTCAC | 4.5e-17 | 5.133 | ZNF274 |

FIG. 5E

Human neuron ATAC peaks

| Motif | e-value | Targ/Bkgr | Best match |
|---|---|---|---|
| ATTGAT_ | 6.2e-913 | 5.346 | HNF6 |
| TA_T_A | 2.6e-335 | 1.871 | PO4F2 |
| GG__AA | 2e-323 | 1.407 | NFKB2 |
| AG_TGGC_ | 1.4e-255 | 3.895 | ZBTB4 |
| C_CC_CCC | 5.2e-234 | 2.009 | SP4 |
| CA__CTC_ | 5.ee-205 | 1.824 | ATOH1 |
| C_GG__A | 2e-123 | 1.291 | CTCF |
| AG_GGGC_ | 1.6e-121 | 2.114 | COE1 |
| CC_CC_CC | 4.6e-107 | 1.912 | CTCF |

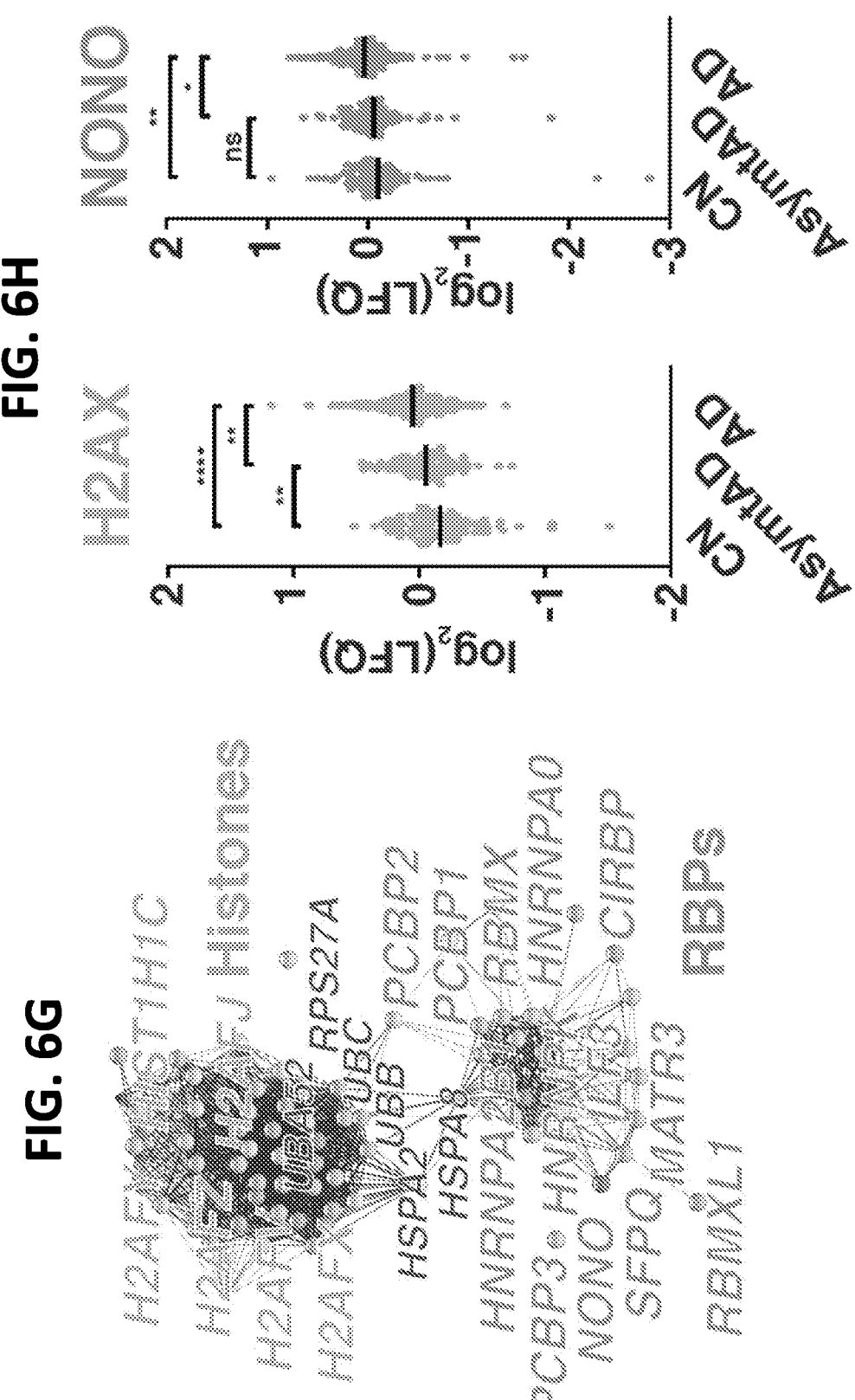

Eigenvector:
A Compartment
B Compartment chr4:0-190,214,555 (500 kb bins)

DNA Repair

FIG. 10B
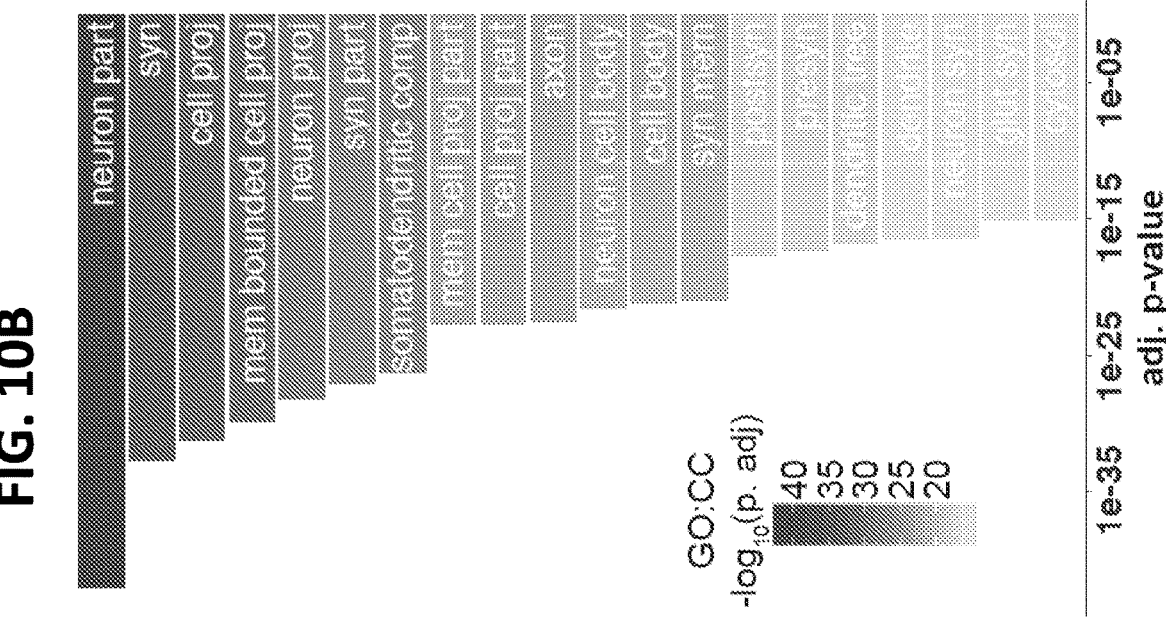
FIG. 10A
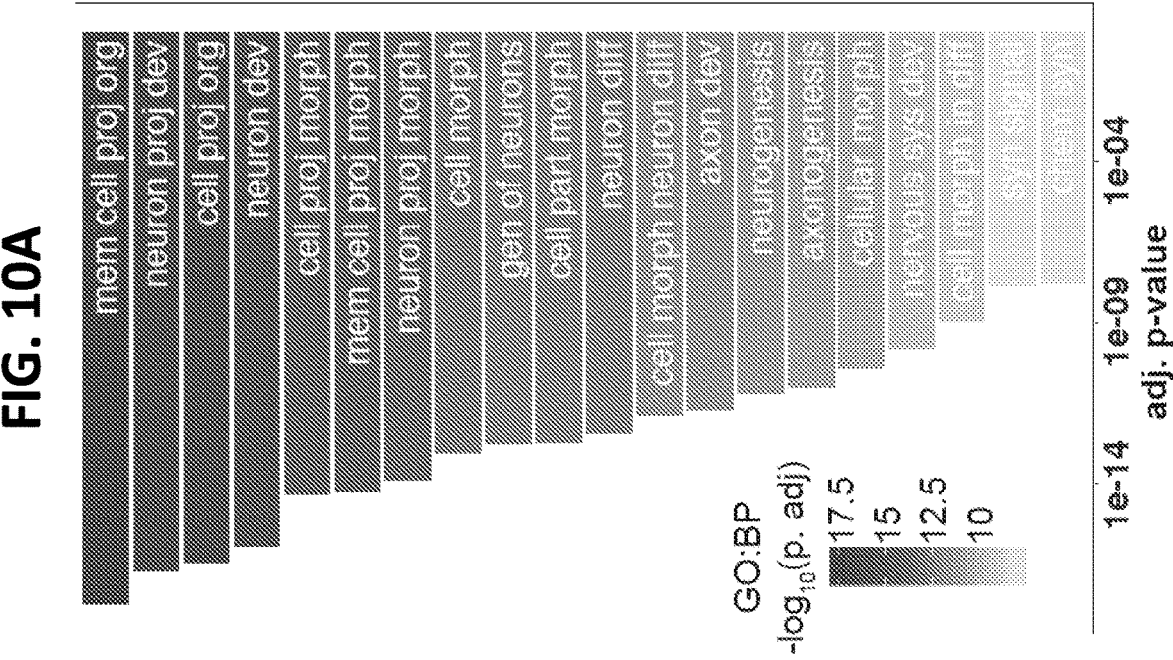

FIG. 17A
FIG. 17B
FIG. 17C
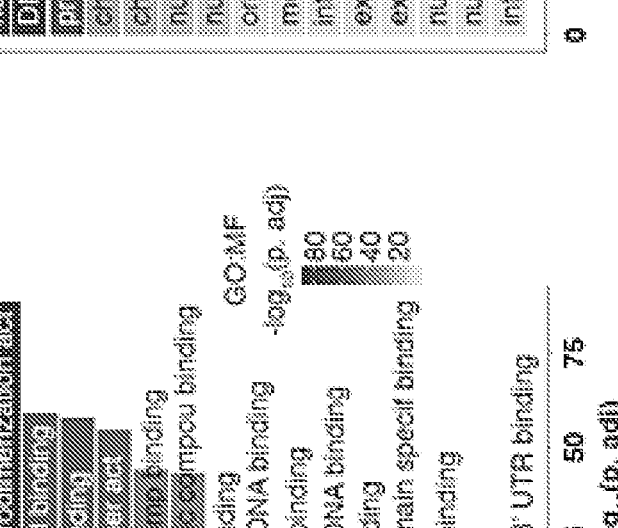
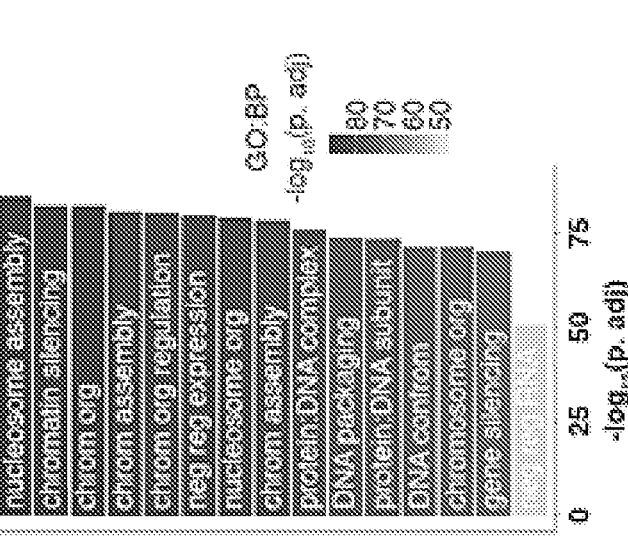

DNA REPAIR SITE DETECTION FOR PERSONAL GENOMICS, EPIGENOMICS, AND GENE THERAPY

CROSS REFERENCE TO RELATED APPLICATIONS

This is the U.S. National Stage of International Application No. PCT/US2020/037757, filed Jun. 15, 2020, which was published in English under PCT Article 21(2), which in turn claims priority to U.S. Provisional Application No. 62/993,449, filed Mar. 23, 2020, both herein incorporated herein in their entireties.

ACKNOWLEDGMENT OF GOVERNMENT SUPPORT

This invention was made with government support under AG056306 and R01AG056511-02 awarded by The National Institutes of Health. The government has certain rights in the invention.

FIELD

Provided are methods for identifying DNA repair locations in a genome of a non-dividing cell.

BACKGROUND

Neurons are highly specialized post-mitotic cells comprising the major functional cell type of the nervous system. While there is a limited capacity to generate new neurons throughout life, the majority of neurons age in parallel with the organism, making them especially susceptible to decline from age-related disruptions in cellular homeostasis (Goncalves et al., *Cell* 167:897-914, 2016; Mattson and Magnus, *Nat Rev Neurosci* 7:278-94, 2006). Neurons must repair $\sim 10^{4-5}$ DNA lesions each day, amounting to more than one billion over the lifespan (Jackson and Bartek, *Nature* 461: 1071-8, 2009). Deficiencies in DNA repair pathways have been linked to developmental neurodegenerative disorders and to genome instability—a primary cellular hallmark of aging often associated with age-related neurodegenerative diseases (McKinnon, Nat Neurosci 16:1523-9, 2013; Lopez-Otin et al., Cell 153:1194-1217 (2013; Chow et al., *Nat Rev Neurosci* 16:672-684, 2015; Hou et al., Mech Ageing Dev 161:83-94, 2017).

Early work on genome integrity in neurons indicated that DNA repair was primarily focused on transcribed genes at the expense of inactive regions of the genome not essential for neuronal function (Nouspikel and Hanawalt, Mol Cell Biol 20:1562-70, 2000; Nouspikel and Hanawalt, DNA Repair (Amst) 1:59-75, 2002). Accumulation of DNA lesions drives age-associated changes in transcription that lead to a decline in neuronal function (Lu et al., Nature 429:883-91, 2004; Vermeij et al., Nature 537:427-431, 2016). Additionally, neuronal activity has been suggested as a source of DNA double strand breaks (DSBs), potentially contributing to genomic instability (Suberbielle et al., Nat Neurosci 16:613-21, 2013; Madabhushi et al., Cell 161: 1592-1605, 2015). Despite a clear link between genome maintenance and neuronal health, surprisingly little is known about how neurons maintain genome integrity, as most of knowledge comes from studies of mitotic neural progenitor cells or expensive whole genome sequencing of single-neurons to address somatic mosaicism (Wei et al., Cell 164:644-655, 2016; Wang et al., Cell Stem Cell 26:221-

233 e226, 2020; Bae et al., Science 359:550-5, 2018; Lee et al., Nature 563:639-45, 2018; Lodato et al., Science 359: 555-9, 2018). Most genomic approaches require a substantial number of cells for targeted specific DNA lesion detection, limiting their adoption (Wei et al., Cell 164:644-655, 2016; Canela et al., *Mol Cell* 63:898-911, 2016). These technical limitations hamper the ability to define the genome protection strategies that neurons have evolved to ensure their unique longevity.

SUMMARY

Provided herein are methods for identifying DNA repair locations in the genome of a non-dividing cell. Such methods include incubating a non-dividing cell containing genomic DNA (gDNA) or chromatin with at least one reactive nucleoside analog under conditions that permit the salvage of the at least one reactive nucleoside analog and incorporation into the gDNA via DNA repair polymerases of the non-dividing cell, thereby generating gDNA comprising the at least one reactive nucleoside analog. In some examples, this incubation is for at least 12 hours, or at least 24 hours. The gDNA or chromatin containing the at least one reactive nucleoside analog is obtained or isolated from the non-dividing cells. This isolated/obtained gDNA or chromatin containing the at least one reactive nucleoside analog is then fragmented, for example by sonication or sheering (e.g., transposase mediated sheering), generating a population of gDNA (or chromatin) fragments. This population of gDNA (or chromatin) fragments contains (1) gDNA (or chromatin) fragments containing the at least one reactive nucleoside analog, and (2) gDNA (or chromatin) fragments not containing the at least one reactive nucleoside analog. Those gDNA (or chromatin) fragments containing the at least one reactive nucleoside analog are isolated or purified away from the gDNA (or chromatin) fragments not containing the at least one reactive nucleoside analog, and are then optionally amplified, and then sequenced, for example using next generation sequencing. Sequencing of the isolated gDNA (or chromatin) fragments containing the at least one reactive nucleoside analog identifies DNA repair locations in the genome of the non-dividing cell. A 'repaired' site map of a region of the genome of the cells can be generated by mapping information obtained from the sequence reads to the region.

In some examples, the non-dividing cell is a myocyte, adipocyte, neuron, skeletal muscle cell, cardiac muscle cell, keratinocyte, pancreatic islet cell, fibroblast, osteocyte, or quiescent stem cell. In some examples, the non-dividing cell is a neuron generated from a subject with a neurodegenerative disease, such as Alzheimer's disease (AD), Parkinson's disease, Amyotrophic Lateral Sclerosis (ALS), Huntington's disease, Batten disease, or Frontotemporal Dementia. Such cells can be generated, for example, by direct trans-differentiation of somatic cells to neurons or reprogramming somatic cells to induced pluripotent stem cells and subsequently deriving or inducing them to neurons. In some examples, the non-dividing cell is obtained from a subject who has previously been administered a CRISPR/Cas therapy, or is a cell that has been treated with CRISPR/Cas therapy and the method identifies off-target CRISPR/Cas gene editing. In such examples, the non-dividing cell can include a guide RNA and a Cas protein (or nucleic acid molecule encoding the Cas protein). In some examples, the non-dividing cell is obtained from a subject having a genetic disorder, such as one listed in Table 1.

In some examples, the at least one reactive nucleoside analog is a thymidine analog or a cytidine analog, such as 5-ethynyl-2'-deoxyuradine (EdU), 5-iodo-2'-deoxyuridine (IdU), 5-chloro-2'-deoxyuridine (CldU), bromodeoxyuridine (BrdU), or 5-ethynyl-2'-deoxycytidine (EdC).

In some examples, gDNA (or chromatin) fragments containing the at least one reactive nucleoside analog are isolated or purified away from the gDNA (or chromatin) fragments that do not contain the at least one reactive nucleoside analog, by a method that includes contacting the population of gDNA (or chromatin) fragments with a reporter molecule (e.g., azide) conjugated to a molecule (such as biotin) that can bind to a solid support or resin (such as avidin or streptavidin), thereby conjugating the reporter molecule to the at least one reactive nucleoside analog, contacting the population of gDNA (or chromatin) fragments with the solid support, wherein gDNA (or chromatin) fragments containing the at least one reactive nucleoside analog bind to the solid support, and removing gDNA (or chromatin) fragments not containing the at least one reactive nucleoside analog. For example, EdU can be reacted with biotin-TEG/PEG-azide in a click chemistry reaction (CuAAC or other), and the resulting biotinylated gDNA (or chromatin) fragments containing the at least one reactive nucleoside analog bind to the solid support, the gDNA (or chromatin) fragments not containing the at least one reactive nucleoside analog are washed away, and the gDNA (or chromatin) fragments containing the at least one reactive nucleoside analog eluted from the solid support. In some examples, gDNA (or chromatin) fragments (or chromatin) containing the at least one reactive nucleoside analog are isolated or purified away from the gDNA (or chromatin) fragments by a method that includes denaturing the population of gDNA (or chromatin) fragments into single-stranded (ss) gDNA (or chromatin) fragments, contacting the population of ssgDNA (or ss chromatin DNA) fragments with an antibody specific for the at least one reactive nucleoside analog, under conditions that allow the antibody to bind to the at least one reactive nucleoside analog, wherein the antibody is attached to a solid support; and separating ssgDNA (or ss chromatin DNA) fragments bound to the antibody and solid support, away from ssgDNA (or ss chromatin DNA) fragments not bound to the antibody and solid support.

The methods can further include incorporating molecular bar codes to a 5'-end, 3'-end, or both ends, of the population of gDNA (or chromatin) fragments or the isolated gDNA (or chromatin) fragments including the at least one reactive nucleoside analog. In some examples the bar code is a sequencing platform adaptor, e.g., "tagging" for subsequent amplification and next generation sequencing (NGS).

The methods can further include amplifying the isolated gDNA (or chromatin) fragments including the at least one reactive nucleoside analog, for example by using PCR or other amplification method. Examples of in vitro amplification methods that can be used include, but are not limited to, PCR, quantitative real-time PCR, isothermal amplification methods, strand displacement amplification; transcription-free isothermal amplification; repair chain reaction amplification; and NASBA™ RNA transcription-free amplification. In one example, the primers specifically hybridize to at least a portion of a molecular tag added to the isolated gDNA (or chromatin) fragments including the at least one reactive nucleoside analog.

The methods can further include aligning the sequenced isolated gDNA (or chromatin) containing the at least one reactive nucleoside analog to a reference genome, such as a human or mouse genome. For example, the non-dividing cell can be a human cell and the reference genome a human reference genome.

The methods can further include incubating the non-dividing cell with one or more test agents before or during the incubating with the at least one reactive nucleoside analog, and the method determines if the one or more test agents can increase or decrease (such as an increase of at least 20%, at least 40%, at least 50%, at least 75%, at least 90%, at least 100%, at least 200%, or at least 500%, or a decrease of at least 20%, at least 40%, at least 50%, at least 75%, at least 90%, or at least 95%) DNA repair as compared to an amount of DNA repair without the one or more test agents.

In some examples, the method includes comparing the identified DNA repair locations between two different non-dividing cells, such as two different non-dividing cells from different subjects (e.g., two neurons from two different subjects), or two different non-dividing cells of different types (e.g., a skeletal muscle cell vs a neuron).

The foregoing and other objects and features of the disclosure will become more apparent from the following detailed description, which proceeds with reference to the accompanying figures.

BRIEF DESCRIPTION OF THE DRAWINGS

FIGS. 1C-1D: Production of post-mitotic ESC-iNs. (A) Schematic for the production of pure ESC-iNs without flow sorting. (B) Representative digital images of ESC-iNs demonstrate no EdU-positive nuclei (fed 24 hrs), and low levels of Ki67 staining (<5%; background) indicate that all cells are non-dividing during this period. Scale bar is 10 microns.

FIGS. 2A-2B. EdU incorporated into the genomes of human post-mitotic neurons by DNA repair can be mapped by next-generation sequencing. (A) Representative super-resolution image of ESC-iN nucleus (dashed line) with EdU repair foci and select zoomed regions. Small EdU clusters are evident in the nucleus (nDNA), whereas mitochondrial biogenesis leads to bright mitochondrial nucleoids (mtDNA) in the cell body. (B) DNA repair peaks from the SNCA locus in EdU-fed ESC-iNs compared with input genomes sequenced to the same depth show substantial enrichment at some sites. Scale bars are 5 microns and 250 nm respectively.

FIGS. 5A-5G. Chromatin accessibility is a primary driver of DNA repair in neurons. (A) Scatter plots of Repair-Seq vs ATAC-Seq, Repair-Seq vs H3K27Ac ChIP-Seq and ATAC-Seq vs H3K27Ac ChIP-Seq. (B) Repair-Seq, ATAC-Seq, and H3K27AC ChIP-Seq peak overlaps. (C) TSS plots for ATAC-Seq and H3K27Ac ChIP-Seq peaks centered on nearest Repair-Seq peak. (D) Genomic annotations for Repair-Seq, ATAC-Seq, H3K27Ac ChIP-Seq peak overlaps. (E) DNA sequence motifs identified de novo in Repair-Seq peaks using all ATAC-Seq peaks as background. (F) DNA sequence motifs identified de novo in Repair-Seq peaks using all H3K27Ac ChIP-Seq peaks as background. (G) Comparison of the enrichment de novo DNA sequence motifs identified in DNA repair hotspots in genes that have hotspots and lack hotspots.

FIGS. 6A-6H. Transcriptional output correlates with total DNA repair but not DNA repair hotspots. (A) Total DNA repair-associated TPMs (transcripts per kilobase million) from Repair-Seq compared with RNA-associated reads from total RNA-Seq. (B) DNA repair-associated reads from DRHs compared with RNA-associated reads from total RNA-Seq. (C) Total DNA repair-associated reads compared with RNA-associated reads from total RNA-Seq in length-normalized TADs. (D) Peak DNA repair-associated reads compared with RNA-associated reads from total RNA-Seq in length-normalized TADs. (E) Select biological process gene ontology terms for genes containing DRHs. (F) Scatter plot of DNA repair-associated reads in DRHs compared with gene length (colored by total DNA repair level). (G) String network representation of peptides enriched for histones (green), RNA binding proteins (RBPs; blue), and some chaperones and ubiquitin (purple). (H) Brain Consensus Protein Coexpression Study labels free quantification (LFQ) proteomics data for H2AX and NONO abundance in cognitively normal (CN), asymptomatic Alzheimer's disease (AsymptAD), and Alzheimer's disease (AD). * p-value<0.5,  p-value<0.01, ** p-value<0.0001 by ANOVA with Tukey's multiple comparison test.

FIGS. 10A-10B. Complete GO terms for biological process and cellular component for genes with DNA repair hotspots. (A) Top 20 biological process GO terms for genes with SGRHs. (B) Top 20 cellular component GO terms for genes with SGRHs.

FIGS. 17A-17C. GO analysis of RIME proteins from DRHs. (A) Top 15 biological process GO terms for DRH proteins. (B) Top 15 molecular pathways GO terms for DRH proteins. (C) Top 15 cellular component GO terms for DRH proteins.

DETAILED DESCRIPTION

Figure 1A:
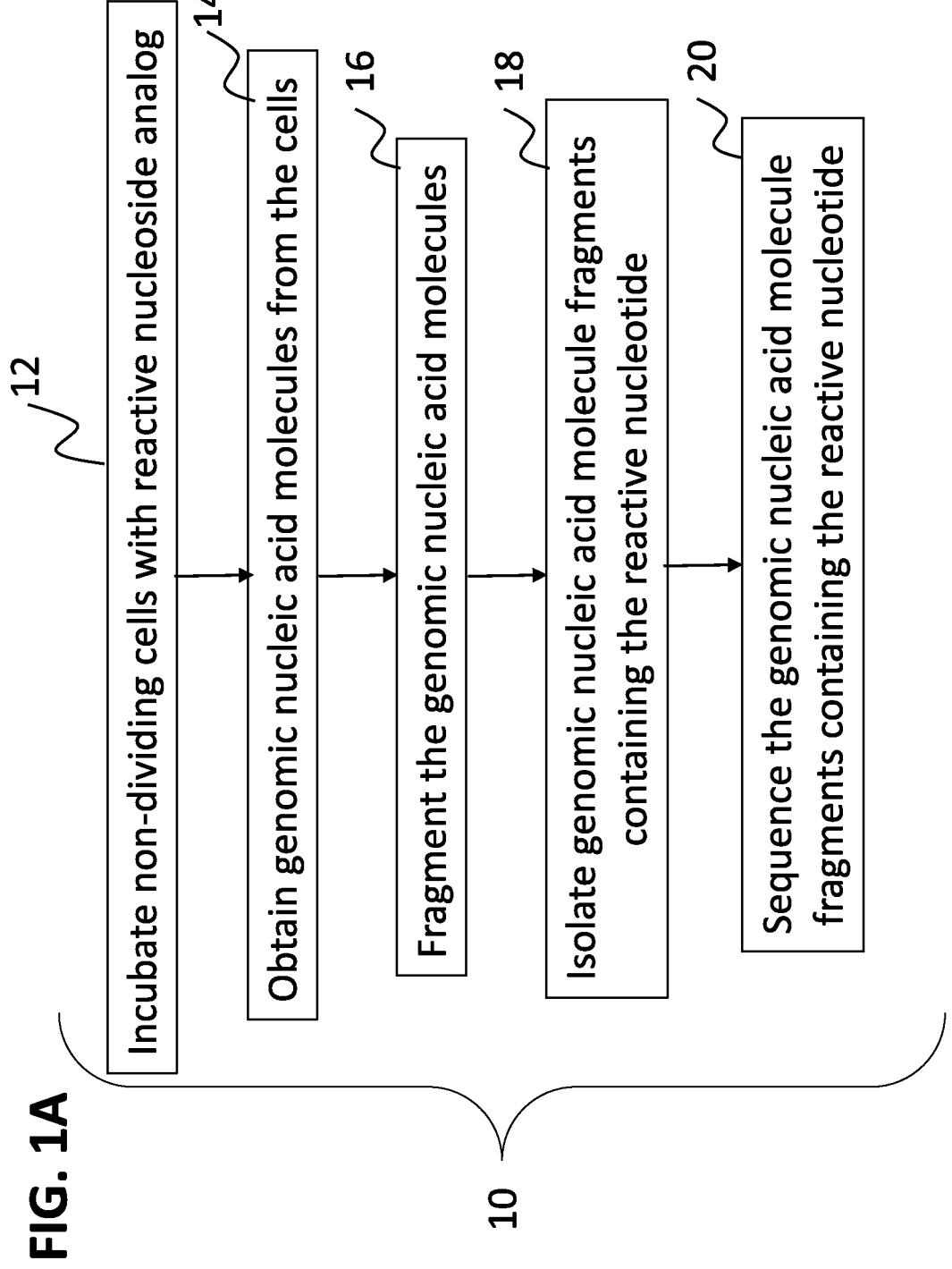
FIG. 1A. Schematic overview of Repair-Seq method. The method 10 includes the following steps. Non-dividing cells (i.e., terminally-differentiated) cells are incubated/cultured in the presence of a reactive nucleoside analog (e.g., EdU) 12. Genomic nucleic acid molecules containing the incorporated reactive nucleoside analog are obtained from the cells 14. The genomic nucleic acid molecules are fragmented 16, for example by using sonication. Genomic nucleic acid molecule fragments containing the nucleoside analog are isolated 18, for example by adding biotin or denaturing the genomic fragments and isolating the desired ss nucleic acid molecules using an antibody. The isolated genomic nucleic acid molecule fragments containing the nucleoside analog are then sequenced 20. In some examples, the method includes preparing a library of genomic nucleic acid molecule fragments containing the nucleoside analog prior to sequencing, for example by adding barcodes to the 5'- and/or 3'-ends of the genomic nucleic acid molecule fragments, to assist in sequencing (such as next-generating sequencing). In some examples, prior to sequencing 20, the method includes amplification of the genomic nucleic acid molecule fragments containing the nucleoside analog.

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers (for the sequence present on Mar. 17, 2020). In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

In order to facilitate review of the various embodiments of the disclosure, the following explanations of specific terms are provided:

Administration: To provide or give a subject an agent, such as a therapeutic agent (such as a guide molecule, Cas9 protein), by any effective route. Exemplary routes of administration include, but are not limited to, injection (such as subcutaneous, intramuscular, intradermal, intraperitoneal, intratumoral, intrathecal, intracerebroventricular, and intravenous), transdermal, intranasal, and inhalation routes.

Antibody: A polypeptide ligand comprising at least a light chain or heavy chain immunoglobulin variable region which specifically recognizes and binds an epitope of an antigen, such as a reactive nucleoside analog. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include portions of antibodies, such as those not having an Fc region, such as Fab fragments, Fab' fragments, F(ab')$_2$ fragments, CH2 deleted Ab, single domain V-region Ab, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, IL); Kuby, J., *Immunology,* 3$^{rd}$ Ed., W. H. Freeman & Co., New York, 1997.

In some examples, antibodies include immunoglobulins that have an Fc region that is mutated or even deleted to substantially decrease the function of the Fc region. In some examples, the mutation decreases the function of the Fc region, such as an ability to bind to Fcγ receptor, by at least 50%, at least 75%, at least 80%, at least 90%, at least 95%, at least 99%, or 100% as compared to the function of the Fc region without the mutation.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a V$_H$ CDR3 is located in the variable domain of the heavy chain of the antibody in which it is found, whereas a V$_L$ CDR1 is the CDR1 from the variable domain of the light chain of the antibody in which it is found. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "V$_H$" or "V$_H$" refer to the variable region of an immunoglobulin heavy chain, including that of an Fv, scFv, dsFv or Fab. References to "V$_L$" or "V$_L$" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

"Specifically binds" refers to the ability of individual antibodies to specifically immunoreact with an antigen, such as reactive nucleoside analog, relative to binding to unrelated antigens. For example, a reactive nucleoside analog-specific binding agent binds substantially only to a particular reactive nucleoside analog in vitro or in vivo. As used herein, the term "reactive nucleoside analog-specific binding agent" includes reactive nucleoside analog-specific antibodies and other agents that bind substantially only to a particular reactive nucleoside analog (e.g., EdU) in that preparation.

The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

In some examples, an antibody or fragment thereof (such as an anti-reactive nucleoside analog molecule) specifically binds to a target (such as a EdU) with a binding constant that is at least 10$^3$ M$^{-1}$ greater, 10$^4$M$^{-1}$ greater or 10$^5$M$^{-1}$ greater than a binding constant for other molecules in a sample or subject. In some examples, an antibody (e.g., monoclonal antibody) or fragments thereof, has an equilibrium constant (Kd) of 1 nM or less. For example, an antibody or fragment thereof binds to a target, such as reactive nucleoside analog (e.g, EdU) with a binding affinity of at least about 0.1× $10^{-8}$M, at least about $0.3×10^{-8}$M, at least about $0.5×10^{-8}$M, at least about $0.75×10^{-8}$M, at least about $1.0×10^{-8}$M, at least about $1.3×10^{-8}$M at least about $1.5×10^{-8}$M, or at least about $2.0×10^{-8}$M, at least about $2.5×10^{-8}$, at least about $3.0×10^{-8}$, at least about $3.5×10^{-8}$, at least about $4.0×10^{-8}$, at least about $4.5×10^{-8}$, or at least about $5.0×10^{-8}$M. In certain embodiments, a specific binding agent that binds to target has a dissociation constant (Kd) of $≤104$ nM, $≤100$ nM, $≤10$ nM, $≤1$ nM, $≤0.1$ nM, $≤0.01$ nM, or $≤0.001$ nM (e.g., $10^{-8}$M or less, e.g., from $10^{-8}$M to $10^{-13}$M, e.g., from $10^{-9}$M to $10^{-13}$M). In one embodiment, Kd is measured by a radio-labeled antigen binding assay (RIA) performed with the Fab version of an antibody of interest and its antigen (see, e.g., Chen et al., *J. Mol. Biol.* 293:865-881, 1999). In another example, Kd is measured using surface plasmon resonance assays using a BIACORES-2000 or a BIACORES-3000 (BIAcore, Inc., Piscataway, N.J.) at 25° C. with immobilized antigen CM5 chips at about 10 response units (RU).

Cas9: An RNA-guided RNA endonuclease enzyme that can cut DNA. Cas9 has two active cutting sites (HNH and RuvC), one for each strand of the double helix. Catalytically inactive (deactivated) Cas9 (dCas9) as also encompassed by this disclosure. In some examples, a dCas9 includes one or more of the following point mutations: D10A, H840A, and N863A.

Cas9 sequences are publicly available. For example, GenBank® Accession Nos. nucleotides 796693 . . . 800799 of CP012045.1 and nucleotides 1100046 . . . 1104152 of CP014139.1 disclose Cas9 nucleic acids, and GenBank® Accession Nos. AMA70685.1 and AKP81606.1 disclose Cas9 proteins. In some examples, the Cas9 is a deactivated form of Cas9 (dCas9), such as one that is nuclease deficient (e.g., those shown in GenBank® Accession Nos. AKA60242.1 and KR011748.1). In certain examples, Cas9 has at least 80% sequence identity, for example at least 85%, at least 90%, at least 95%, at least 96%, at least 97%, at least 98%, or at least 99% sequence identity to such sequences, and retains the ability to cut DNA.

Cell Culture: Cells grown under controlled conditions. A primary cell culture is a culture of cells, tissues or organs taken directly from an organism (such as a human or other mammal). Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time. In some examples, a cell culture includes cells in a non-dividing state, that is, they are terminally-differentiated or growth arrested through removal of growth factors/contact inhibition/or treatment with pharmacological agents.

Complementarity: The ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

Contact: Placement in direct physical association, including a solid or a liquid form. Contacting can occur in vitro or ex vivo, for example, by adding a reagent (such as a reactive nucleoside analog) to a culture of non-dividing cells, or in vivo by administering to a subject.

CRISPRs (Clustered Regularly InterSpaced Repeats): The CRISPR RNA array is a defining feature of CRISPR systems. The term "CRISPR" refers to the architecture of the array which includes constant direct repeats (DRs) interspaced with the variable spacers. In some examples, a CRISPR array includes at least a DR-spacer-DR-spacer. CRISPRs are found in approximately 40% of sequenced bacteria genomes and 90% of sequenced archaea. CRISPRs are often associated with cas genes that code for proteins related to CRISPRs (such as Cas9 proteins). CRISPR/Cas systems can be used for DNA or RNA targeting, for example to detect a target DNA or RNA, modify a target DNA or RNA at any desired location, or cut the target DNA or RNA at any desired location.

The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. CRISPR/Cas systems can be used for gene editing (adding, disrupting or changing the sequence of specific genes) and gene regulation. By delivering a Cas9 protein and appropriate guide RNAs into a cell, the organism's genome or RNA can be cut at any desired location.

DNA repair polymerase: A DNA polymerase capable of correcting an erroneously incorporated nucleotide into a DNA strand, for example by double-strand break repair, single-strand break repair, mismatch repair, nucleotide excision repair, base excision repair, transcription coupled, or trans-lesion repair. In one example, the repair DNA polymerase is DNA polymerase beta, delta or epsilon which are used in base excision-repair and removes many modified bases and abasic sites. In one example, the repair DNA polymerase is DNA polymerases delta or epsilon, which are used in nucleotide excision-repair to resynthesize the bases removed during repair of pyrimidine dimers and other bulky adducts in DNA, and in mismatch-repair of replication errors. DNA polymerase alpha is required for semi-conservative replication of DNA but not for repair of DNA. In one example, the DNA repair polymerase is DNA polymerase zeta, which is involved in the bypass of damage, without excision, and occurs during DNA replication of a damaged template. This includes the incorporation of nucleotides that differ from the template DNA strand. In one example, this includes DNA polymerase theta, which is involved in theta mediated end joining following the failure of nonhomologous end joining.

Gene Editing: A type of genetic engineering in which a nucleic acid molecule, such as DNA, is inserted, deleted or replaced in the genome of an organism using engineered nucleases, which create site-specific double-strand breaks (DSBs) at desired locations in the genome. The induced double-strand breaks are repaired through nonhomologous end-joining (NHEJ) or homologous recombination (HR), resulting in targeted mutations or repairs. CRISPR/Cas methods can be used to edit the sequence of one or more target genes, such as one associated with cancer (e.g., CIVIL, lung cancer, breast cancer, colon cancer), infectious disease (such as HIV, SARS-CoV-2, hepatitis, HPV, and West Nile virus), or neurodegenerative disorder (e.g., Huntington's disease or ALS). For example, gene editing can be used to treat a disease, or to make a disease more susceptible to a therapy. Gene editing can also be used to mutate a gene in a test organism, to examine the role of the gene in vivo.

Gene Silencing: A specific type of gene regulation, namely significantly reducing (e.g., a reduction of at least 90%, at least 95%, or at least 99%) or preventing expression of a gene. Can also be referred to as knocking out gene expression, when the gene is completely silenced. CRISPR/Cas methods can be used to silence expression of one or more target genes, such as one associated with cancer (e.g., CIVIL, breast cancer, colon cancer), infectious disease (such as HIV, SARS-CoV-2, hepatitis, HPV, and West Nile virus), or neurodegenerative disorder (e.g., Huntington's disease or ALS).

Genomic insertion site: A site of the genome that is targeted for, or has undergone, insertion of an exogenous polynucleotide.

Guide sequence: A polynucleotide sequence having sufficient complementarity with a target polynucleotide sequence to hybridize with the target sequence and direct sequence-specific binding of a Cas9 to the target sequence. In some examples, the guide sequence is RNA. In some examples, the guide sequence is DNA. The guide nucleic acid can include modified bases or chemical modifications (e.g., see Latorre et al., *Angewandte Chemie* 55:3548-50, 2016). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about, or at least, about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, a guide sequence is 15-25 nucleotides (such as 18-22 or 18 nucleotides).

The ability of a guide sequence to direct sequence-specific binding of a CRISPR complex to a target sequence may be assessed by a suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

Isolated: An "isolated" biological component (such as a cell, protein, or nucleic acid molecule) has been substantially separated, produced apart from, or purified away from other biological components in the cell or tissue of an organism in which the component occurs, such as other cells, chromosomal and extrachromosomal DNA and RNA, and proteins. Nucleic acids and proteins that have been "isolated" include nucleic acids (e.g., gDNA, chromatin, or fragments thereof) and proteins purified by standard purification methods. The term also embraces nucleic acids and proteins prepared by recombinant expression in a host cell as well as chemically synthesized nucleic acid molecules and proteins. Isolated proteins or nucleic acid molecules (e.g., gDNA, chromatin, or fragments thereof), or cells containing such, in some examples are at least 50% pure, such as at least 75%, at least 80%, at least 90%, at least 95%, at least 98%, or at least 100% pure.

Mammal: This term includes both human and non-human mammals. Similarly, the term "subject" includes both human and veterinary subjects.

Non-dividing cell: Includes cells that are not replicating and terminally differentiated. Includes primary cells and established cell lines. In some examples, a non-dividing cell is in a post-mitotic state and cannot re-enter the cell cycle. In some examples, the non-dividing cell is isolated from a subject, such as a mammalian subject, such as a human or veterinary subject that has received CRISPR/Cas9 therapy. In some examples, a non-dividing cell is a non-dividing glial cells (e.g., astrocyte, oligodendrocyte, or microglia). In some examples, a non-dividing cell is a myocyte, adipocyte, neuron, skeletal muscle cell, cardiac muscle cell (cardiomyocyte), keratinocyte, pancreatic islet cell, fibroblast, osteocyte, tissue resident macrophage, astrocytes, hepatocyte, T-cell, B-cell, oocyte, or quiescent stem cell.

Reactive nucleoside analog: An analog of a nucleoside or ribonucleoside containing a detectable label, which can incorporate into a DNA or RNA strand, and thus be used to detect where a nucleotide has been recently incorporated into a nucleic acid molecule, for example due to nucleic acid (e.g., DNA) repair. Examples of detectable labels include those that can be subsequently detected with a fluorescent azide or biotin azide via "click" chemistry. Other examples of detectable labels include those that can be subsequently detected with an antibody.

Includes analogs of adenosine, guanosine, cytidine, thymidine and uridine. Exemplary thymidine and uridine analogs include 5-ethynyl-2'-deoxyuradine (EdU), 5-iodo-2'-deoxyuridine (IdU), 5-chloro-2'-deoxyuridine (CldU), and 5-bromo-2'-deoxyuridine (BrdU). In one example, the nucleoside analog is a halogenated nucleoside, such as one containing a F, Cl or Br, such as BrdU and IdU. In some examples, nucleoside analogs are provided in a pro-drug form, for example to improve their toxicological profiles in animals or cells.

Subject: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a disorder or genetic disease that can be treated using CRISPR/Cas. In some examples, the subject is a laboratory animal/organism, such as a zebrafish, *Xenopus, C. elegans, Drosophila*, mouse, rabbit, or rat.

Under conditions sufficient for: A phrase used to describe any environment that permits a desired activity. In one example the desired activity is incorporation of at least one reactive nucleoside analog into the genomic DNA (or chromatin) of a non-dividing cell.

Overview

Neurons are the longest-living cells in our bodies, becoming post-mitotic in early development upon terminal differentiation. Their lack of DNA replication makes them reliant on DNA repair mechanisms to maintain genome fidelity. These repair mechanisms decline with age, potentially giving rise genomic dysfunction that may influence cognitive decline and neurodegenerative diseases. Despite this challenge, knowledge of how genome instability emerges and what mechanisms neurons and other long-lived cells may have evolved to protect their genome integrity over the human life span is limited. Using a targeted sequencing approach, it is shown herein that neurons consolidate much of their DNA repair efforts into well-defined hotspots that protect genes that are essential for their identity and function. These hotspots are enriched with histone H2A isoforms and RNA binding proteins and are associated with evolutionarily conserved elements of the human genome. These results provide a basis to understand genome integrity as it relates to aging and disease in the nervous system. Based on these results, other non-dividing cells can be examined using the same methods. For example, such methods can be used to identify off-target CRISPR/Cas9 activity.

Aging is a crucial risk factor for complex neurodegenerative diseases such as Alzheimer's disease (AD), Parkinson's disease, Amyotrophic Lateral Sclerosis, and Frontotemporal Dementia. With the exception of rare inherited forms of these conditions, the vast majorities are sporadic—lacking a clear etiological link between genetics or environment and the manifestation of symptoms. A major driver of age-dependent cellular dysfunction and neurodegeneration in humans is DNA damage. A typical mammalian cell weathers ~100,000 DNA lesions per day. In most cases, damage does not result in lasting somatic mutations because cells possess efficient DNA damage response (DDR) pathways capable of resolving even the most deleterious forms of damage. DDR pathways include base and nucleotide excision repair (BER/NER), mismatch repair (MMR), homologous recombination (HR) and non-homologous end joining (NHEJ). Though DDR is proficient at driving overall cellular survival, it is not perfect, and erroneous repairs will accumulate in cells with age. Heavily damaged genomes typically result in apoptosis of the affected cell, and replacement of these lost cells is facilitated by the generation of replacement cells from pools of stem cells in most tissues. In the brain however, most neurons are born during embryogenesis and early life, synaptically integrate into a complex connectome, and thus face a demand for life-long survival. Given this very limited capacity for self-renewal, neurons are targets for age-related decline due to DNA damage.

In the aging brain, neurons face elevated rates of DNA damage, as harmful agents such as reactive oxygen species (ROS) are present at higher levels, and protective structures including the nuclear envelope and pores degrade with age. Thus, DNA repair failures are written into genomes, with the damage and its functional consequences being irreversible. In addition to elevated mutation rates, age-dependent defects in the DDR machinery can be causative for neurodegenerative phenotypes. Further, monogenic premature aging syndromes such as Cockayne syndrome or Trichothiodystrophy are caused by mutations in DDR genes and, in addition to other phenotypes, lead to neurodegeneration.

While it has been assumed that age-related DNA damage is randomly distributed over the genome, it might occur with greater frequency in certain genomic hotspots. However, previous data based on whole genome sequencing to identify mutations does not take into account error-free repair, which is the most common result of DNA damage and DDR. Provided herein are new methods to identify both mutating and error-free repair, which sequence DNA that was repaired within a set time frame. Such technology is valuable, as DNA damage are likely cell type-specific and might have very discrete consequences, such as transient disruption to chromatin by DDR-associated chromatin remodelers.

Based on the results provided herein, it is proposed that distinct hotspots for age-related DNA damage exist in aging neurons and that they are causative for the pathological gene expression changes occurring in AD patient-specific neurons. The combination of age-related decline in DDR and AD neuron-specific elevated levels of damage (e.g., ROS) causes an AD neuron-specific loss of genome maintenance, deleterious gene expression changes, and cellular decay. Based on observations in aging human induced neurons (iNs) from a cohort of well-characterized AD patients and healthy age-matched control subjects, profound changes in neuronal gene expression were detected that are indicative of a loss of neuronal connectivity and functionality, metabolic defects and dysregulation of DNA repair. Interestingly, all AD-specific differences present in iNs were erased when the cells underwent cellular rejuvenation by bypassing the induced pluripotent stem cell (iPSC) state before neuronal induction (iPSC-iN), indicating that cellular aging is required for AD-specific defects to unfold. Functional characterization of old AD iNs further confirmed that the cells undergo a metabolic switch from oxidative phosphorylation to aerobic glycolysis, which also results in elevated levels of ROS.

The method provided herein, termed "Repair-Seq," is summarized in FIG. 1A. This method is based on genomic incorporation of a reactive nucleoside analog, such as EdU, and isolation of reactive nucleoside analog-rich DNA fragments (e.g., EdU-rich DNA fragments), followed by sequencing. This method allows identifies the specific repaired sequence, and thereby quantifies, maps and characterizes repaired DNA in non-dividing cells (e.g., postmitotic neurons).

Figure 1B:
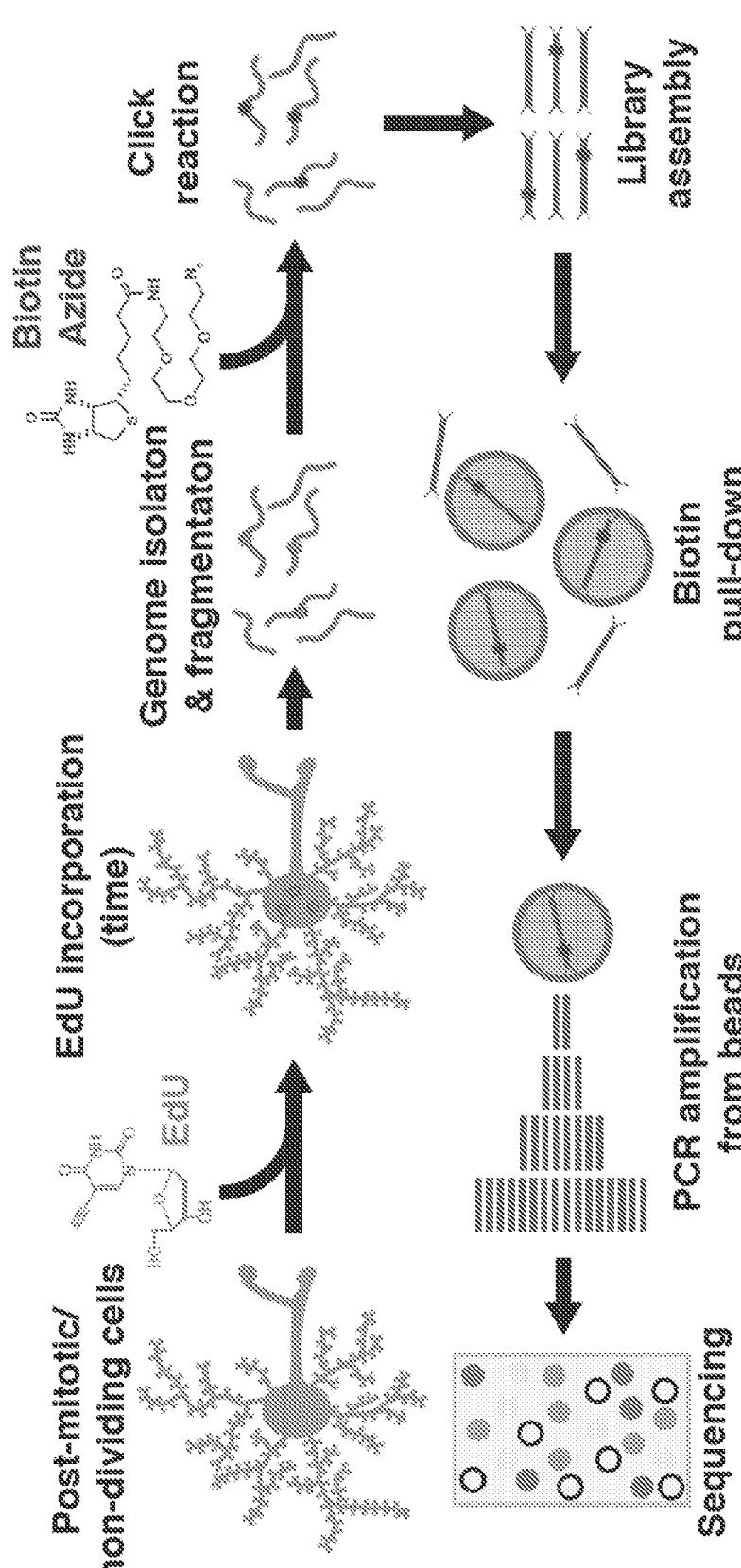
FIG. 1B. Schematic for specific example of assembly and sequencing of Repair-Seq libraries. Post-mitotic neurons are cultured in the presence of EdU for at least 24 hr. Neurons are harvested and their genomes are isolated and fragmented with sonication. A click reaction is performed to add on a biotin to the EdU present in the neuronal genome. Illumina compatible libraries are then assembled and EdU containing fragments, enriched on streptavidin beads, and subsequently amplified from the beads for NGS.

A specific example of the method is provided in FIG. 1B. Non-dividing cells, such as neurons, are incubated or contacted with a reactive nucleoside analog, here, EdU. Genomic DNA is subsequently isolated from the cells, and fragmented. The gDNA fragments are incubated with biotin azide in a click reaction, thereby labeling the gDNA fragments containing the reactive nucleoside analog with biotin. The gDNA fragments are used to assembly a library (e.g., adding molecular bar codes to the 5/- and 3'-ends of the gDNA fragments), and the biotin gDNA fragments containing the reactive nucleoside analog recovered using avidin or streptavidin beads (the order of these two steps can be reversed). The recovered gDNA fragments containing the reactive nucleoside analog are PCR amplified and then sequenced, for example with NGS or long read or nanopore sequencing. In the case of long read or nanopore sequencing, the location of nucleoside incorporation can be directly detected without the addition of specific epitopes for isolation, with enrichment via antibody mediated pull-down of single-strand intermediates (omitting PCR amplification).

One skilled in the art will appreciate that chromatin can be analyzed as an alternative to (or in addition to) gDNA using any of the methods provided herein (e.g., those exemplified in FIGS. 1A and 1B).

Repaired-Seq Method

Provided herein is a method that uses non-dividing cells for identifying the locations in a genome where DNA repair has occurred. Non-dividing cells are long-lived in comparison with rapidly dividing cells, and as such accumulate more DNA damage to their genomes. The appropriate repair of DNA lesions is essential for maintaining cell and organismal health—disruptions to DNA repair genes have been known to cause both neurodegeneration and cancer. The methods described herein allow for the determination of the location of DNA repair sites in cells that are not dividing over a short time period. This allows the determination of genes and gene networks that are more susceptible to disruption (i.e., altered chromatin state/transcription). Furthermore, this technique can reveal off target sites for gene editing methods, such as CRISPR/Cas or Zinc Finger Nuclease based technologies in these cell types.

As shown in FIG. 1A, the method 10 includes incubating a non-dividing cell containing genomic DNA (gDNA) with at least one reactive nucleoside analog under conditions that permit the at least one reactive nucleoside analog to be taken up by the cell and incorporated into the gDNA via a DNA repair polymerase of the non-dividing cell 12. This labels DNA repair sites, which can be subsequently detected. Incorporation of a reactive nucleoside and incorporation of it into the genome of a non-dividing cell occurs via the action of DNA repair polymerases. Unlike replicative DNA polymerases, repair polymerases only incorporate a few nucleotides as part of DNA repair processes in the cell. These include (but are not limited to) double-strand break repair, single-strand break repair, mismatch repair, nucleotide excision repair, base excision repair, and transcription coupled, and trans-lesion repair. Step 12 generates gDNA containing at least one reactive nucleoside analog that was incorporated during repair of the gDNA. In some examples, the non-dividing cell is incubated with the at least one reactive nucleoside for at least 6 hours, at least 8 hours, at least 10 hours, at least 12 hours, or at least 24 hours, such as 12-48 hours, such as 24 hours, for example at about 37° C. In some examples, the non-dividing cell is incubated with the at least one reactive nucleoside for a shorter period, for example when a nucleic acid damaging agent is also incorporated into the method, such as at least 15 minutes, at least 30 minutes, at least 1 hour, at least 2 hours, or at least 3 hours, for example at about 37° C.

As shown in FIG. 1A, gDNA containing the incorporated at least one reactive nucleoside analog is subsequently obtained or isolated from the non-dividing cells 14, for example using gDNA or chromatin purification methods. In some examples, the non-dividing cells are lysed or otherwise disrupted to liberate the gDNA or chromatin, which is then isolated. The obtained gDNA (or chromatin) containing at least one reactive nucleoside analog is fragmented into smaller pieces 16, for example by sonication or sheering (e.g., transposase mediated sheering). In some examples, the fragmenting produces a population of gDNA (or chromatin) fragments of no more than 1000 bp in length, no more than 700 bp in length, or no more than 550 bp in length, such as 200 bp to 700 bp, 300 bp to 500 bp, or about 350-450 bp in length. This population of gDNA (or chromatin) fragments includes (1) gDNA (or chromatin) fragments containing the at least one reactive nucleoside (e.g., contain a location where a repair was made), and (2) gDNA (or chromatin)

fragments not containing the at least one reactive nucleoside analog (e.g., do not include a sequence where a repair was made). In some examples, gDNA (or chromatin) containing the incorporated at least one reactive nucleoside analog is subsequently obtained or isolated from the non-dividing cells but a pull-down step is not performed (e.g., nucleoside analogs are detected directly during sequence, for example when using long read sequencing or direct nanopore sequencing).

Specific gDNA (or chromatin) fragments containing at least one reactive nucleoside analog are isolated 18, that is, they are separated away from gDNA (or chromatin) fragments not containing at least one reactive nucleoside analog. In some examples, this is achieved by separating the gDNA (or chromatin) fragments containing at least one reactive nucleoside analog into single stranded (ss) gDNA (or ss chromatin DNA) molecules (for example by heating and/or other denaturing methods), and containing the ssgDNA (or ss chromatin DNA) fragment with an antibody specific for the at least one reactive nucleoside analog, such as an anti-BrdU antibody, anti-IdU, or anti-EdU. In some examples, the antibody is attached (e.g., covalently attached) to a solid support, such as a bead (e.g., metal, glass, or plastic) or other surface (e.g., of a multi-well plate), allowing capture of the ssgDNA (or ss chromatin DNA) fragment containing at least one reactive nucleoside analog. ssgDNA (or ss chromatin DNA) fragments not containing at least one reactive nucleoside analog can we washed or otherwise separated away. In some examples, this is achieved by performing a click chemistry reaction compatible with the specific at least one reactive nucleoside analog used. For example, the population of gDNA (or chromatin) fragments can be incubated with a reporter molecule that reacts with the reactive nucleoside analog, thereby permitting separation or isolation of gDNA (or chromatin) fragments containing the at least one reactive nucleoside analog. Exemplary reporter molecules include fluorophores (such as a biotin-fluorescent conjugate) and molecules that can bind to a certain column or resin, such as biotin (which can bind to an avidin or streptavidin column/resin). In some examples flow cytometry is used to identify fluorescent cells. In some examples, a tyramide amplification assay is used (e.g., see Wienholz et al., Nucleic Acids Res. 45:e68, 2017). In some examples, the method can include contacting the population of gDNA fragments with a reporter molecule conjugated to a molecule that can bind to a solid support (such as biotin azide, which can bind an avidin or streptavidin column/resin), thereby conjugating the reporter molecule to the at least one reactive nucleoside analog. The population of gDNA (or chromatin) fragments are incubated with the solid support, under conditions that permit the ssgDNA (or ss chromatin) fragments comprising the at least one reactive nucleoside analog bind to the solid support (e.g., avidin beads), while ssgDNA (or ss chromatin) fragments not comprising the at least one reactive nucleoside analog do not bind to the solid support and thus can be separated from the ssgDNA (or ss chromatin) fragments bound to the solid support (e.g., by washing). In one example, click chemistry covalently couples an azide with an alkyne (copper(I)-catalyzed azide-alkyne cycloaddition, CuAAC). For example, detection of EdU employs the copper(I) catalyzed click reaction with an azide, such as one coupled to biotin. In some examples, the reactive nucleoside analog is one containing an alkyne (e.g., EdU) and the reporter molecule is an azide containing molecule (e.g., biotin-azide). Other examples including strain-promoted azide-alkyne cycloaddition (SPAAC) are provided in Dommerholt et al. (Top. Curr. Chem. 374:16, 2016).

As shown in FIG. 1A, once the gDNA (or chromatin) fragments containing the at least one reactive nucleoside analog are isolated 18, they can be sequenced 20, for example to identify the location of the reactive nucleoside analog incorporated into the gDNA (or chromatin) during repair. In some examples, next generation sequencing is performed. The method can further include aligning the sequenced isolated gDNA or chromatin) fragments comprising the at least one reactive nucleoside analog to a reference genome (i.e., reference assembly), such as a human reference genome (e.g., hg38/GRCh38) or a mouse reference genome (e.g., mm10).

The method shown in FIG. 1A can include other steps. For example, molecular bar codes can be added to the 5'-end, 3'-end, or both, of the gDNA (or chromatin) fragments generated in step 16. The addition of bar codes, can be done before or after the gDNA (or chromatin) fragments containing the reactive nucleoside analog are isolated in step 18. In one example, the molecular bar code includes a sequencing platform adaptor, which includes a nucleic acid sequence that permits capture of the gDNA (or chromatin) fragments onto a sequencing platform. This can be used for library assembly. In some examples, the molecular bar code is added to permit subsequent amplification of the isolated gDNA (or chromatin) fragments.

In some examples, the non-dividing cells are obtained from a subject, such as a mammalian subject, for example a human or mouse. In some examples, the non-dividing cells are obtained from a mammalian subject, such as one who was previously administered a CRISPR/Cas therapy, such as a Cas9 protein (or coding sequence thereof) and a guide sequence specific for a target gene (such as a gene containing a mutation causing disease). Thus, in some examples the non-dividing cells include a gRNA (specific for a target gene, such as one involved in disease), and a Cas protein (or coding sequence), such as Cas9. In some examples, the non-dividing cells are obtained from a mammalian subject having a neurodegenerative disease, such as Alzheimer's disease (AD), Parkinson's disease, Amyotrophic Lateral Sclerosis, Huntington's disease, Batten disease, or Fronto-temporal Dementia. In some examples, the non-dividing cells used are purified or isolated. In some examples, no more than $1 \times 10^6$ non-dividing cells are used, such as about 0.1 to $0.9 \times 10^6$ non-dividing cells, 0.4 to $0.6 \times 10^6$ non-dividing cells, or about $0.5 \times 10^6$ non-dividing cells are used. Exemplary non-dividing cells that can be used include myocytes, astrocytes, microglia, adipocytes, neurons, skeletal muscle cells, cardiac muscle cells, keratinocytes, pancreatic islet cells, issue resident macrophages, astrocytes, hepatocytes, T-cells, B-cells, oocytes, fibroblasts, osteocytes, senescent cells, cancer stem cells, and quiescent stem cells.

In some examples, the at least one reactive nucleoside analog is a thymidine analog or a cytidine analog. Exemplary thymidine analogs include 5-ethynyl-2'-deoxyuradine (EdU), 5-iodo-2'-deoxyuridine (IdU), 5-chloro-2'-deoxyuridine (CldU), and bromodeoxyuridine (BrdU). An exemplary cytidine analog is 5-ethynyl-2'-deoxycytidine (EdC).

In some examples, the method identifies DNA repair sites in vivo. In such a method, the reactive nucleoside analog is administered to the subject (i.e., step 12 of FIG. 1A is performed in vivo), and at least one non-dividing cell subsequently obtained from the subject and analyzed ex vivo using the disclosed methods (i.e., steps 14, 16, 18, 20 of FIG. 1A are performed ex vivo).

Identification of CRISPR/Cas Off-Target Editing

In one example, the method is used to identify CRISPR/Cas off target editing. For example, the method can be used to identify gain and loss of DNA repair hotspots in cells treated with CRISPR/Cas and cells from patients treated with CRISPR/Cas. Off-target editing includes unintended point mutations, deletions, insertions inversions, and translocations made to a nucleic acid molecule, such as gDNA, of the treated cells/subjects.

Central to the CRISPR system is a complex machinery formed by a Cas protein, guide RNA (gRNA or sgRNA), and the target DNA. Two factors that determine the specificity of CRISPR gene editing are (a) the hybridization between Cas/sgRNA and the target, as directed by the sequence recognition at the protospacer adjacent motif (PAM) site and the DNA target site, and (b) the subsequent specific conformational changes in the Cas/sgRNA/DNA complex for the cleavage reaction. CRISPR/Cas can be used for gene editing; however, the accuracy and reliability of this technology are severely hampered by the off-target effects, namely, the unintended cleavage of DNA at sites whose sequences show mismatches with the guide RNA (gRNA or sgRNA). The disclosed methods can be used to identify such off-target effects, such that if significant undesirable off-target effects are observed, one can redesign elements of a particular CRISPR/Cas system (e.g., modify gRNA sequence) to reduce off-target effects.

Thus, in some examples, the non-dividing cell used in the disclosed methods is one treated with CRISPR/Cas, or is a cell obtained from a subject treated with CRISPR/Cas. As a result, in some examples, the non-dividing cell used in the disclosed methods also includes a gRNA and a Cas protein (or a coding sequence thereof). In one example, the non-dividing cell used in the disclosed methods includes one or more plasmids or vectors to encoding the Cas enzyme and the gRNA with the target sequence. In one example, the non-dividing cell is obtained from a subject with a genetic disease and has been treated with CRISPR/Cas. Thus, in some examples, the non-dividing cell is obtained from a subject with a genetic disease that can be treated with CRISPR/Cas. Examples of such diseases include any genetic disease of the blood (e.g. sickle cell disease, primary immunodeficiency diseases), HIV (such as HIV-1), and hematologic malignancies or cancers. Examples of primary immunodeficiency diseases and their corresponding mutations include those listed in Al-Herz et al. (*Frontiers in Immunology*, volume 5, article 162, Apr. 22, 2014, herein incorporated by reference in its entirety). Hematologic malignancies or cancers are those tumors that affect blood, bone marrow, and lymph nodes. Examples include leukemia (e.g., acute lymphoblastic leukemia, acute myelogenous leukemia, chronic lymphocytic leukemia, chronic myelogenous leukemia, acute monocytic leukemia), lymphoma (e.g., Hodgkin's lymphoma and non-Hodgkin's lymphoma), and myeloma. Table 1 provides a list of exemplary disorders and genes that can be targeted and corrected by CRISPR/Cas.

TABLE 1

| Exemplary disorders and corresponding mutations | | |
| --- | --- | --- |
| Disease | Gene | Mutation |
| Blood cell disorder | | |
| sickle cell anemia | β-globin chain of hemoglobin | SNP (A to T) that gives rise to point mutation (Glu−>Val at $6^{th}$ aa) |
| hemophilia | any of clotting factors I through XIII | |
| hemophilia A | clotting factor VIII | large deletions, insertions, inversions, and point mutations |
| hemophilia B | clotting factor IX | |
| Alpha-Thalassemia | HBA1 or HBA2 | Mutation or a deletion in chromosome 16 p |
| Beta-Thalassemia | HBB | Mutations in chromosome 11 |
| Delta-Thalassemia | HBD | mutation |
| von Willebrand Disease | von Willebrand factor | mutations or deletion |
| pernicious anemia | MTHFR | |
| Fanconi anemia | FANCA, FANCC, FANCD2, FANCG, FANCJ | FANCA: c.3788__3790del (p.Phe1263del); c.1115__1118delTTGG (p.Val372fs); Exon 12-17del; Exon 12-31del; c.295C > T (p.Gln99X) FANCC: c.711 + 4A > T (originally reported as IVS4 + 4A > T); c.67delG (originally reported as 322delG) FANCD2: c.1948 − 16T > G FANCG; c.313G > T (p.Glu105X); c.1077 − 2A > G; c.1480 + 1G > C; c.307 + 1G > C; c.1794__1803del (p.Trp599fs); c.637__643del (p.Tyr213fs) FANCJ: c.2392C > T (p.Arg798X) |
| Thrombocytopenic purpura | ADAMTS13 | Missense and nonsense mutations |
| thrombophilia | Factor V Leiden Prothrombin | Mutation in the F5 gene at position 1691 Prothrombin G20210A |
| Primary Immunodeficiency Diseases | | |
| T-B+ SCID | IL-2RG, JAK3, defect in gamma chain of receptors for IL-2, -4, -7, -9, -15 and -21 | |
| T-B− SCID | RAG1, RAG2 | |
| WHIM syndrome | CXCR4 | heterozygous mutations (e.g., in the carboxy-terminus); carboxy-terminus truncation (e.g., 10-19 residues) |
| Other Primary immune deficiency (PID) syndromes | | |
| IL-7 receptor severe combined immune deficiency (SCID) | IL7 receptor | |
| Adenosine deaminase deficiency (ADA) SCID | ADA | |
| Purine nucleoside phosphorylase (PNP) deficiency | PNP | |
| Wiskott-Aldrich syndrome (WAS) | WAS | More than 300 mutations identified |
| Chronic granulomatous disease (CGD) | CYBA, CYBB, NCF1, NCF2, or NCF4 | |
| Leukocyte adhesion deficiency (LAD) | Beta-2 integrin | |
| HIV | C-C chemokine receptor type 5 (CCR5), MSRB1 HIV long terminal repeats CSCR4 P17 PSIP1 | Deletion of 32 bp in CCR5 |

TABLE 1-continued

| Exemplary disorders and corresponding mutations | | |
| --- | --- | --- |
| Disease | Gene | Mutation |
| Duchenne muscular dystrophy | CCR5 DMD | |
| Glycogen storage disease type IA | G6Pase | |
| Retinal Dystrophy | CEP290 | C2991 + 1655A > G |
| | ABCA4 | 5196 + 1216C > A; 5196 + 1056A > G; 5196 + 1159G > A; 5196 + 1137G > A; 938 − 619A > G; 4539 + 2064C > T |
| X-linked immunodeficiency with magnesium defect, Epstein-Barr virus infection, and neoplasia (XMEN) MonoGenetic Disorders | MAGT1 | |
| Metachromatic leukodystrophy (MLD) | arylsulfatase A (ARSA) | |
| Adrenoleukodystrophy (ALD) | ABCD1 | |
| Mucopolysaccaridoses (MPS) disorders | IDS | |
| Hunter syndrome | IDUA | |
| Hurler syndrome | IDUA | |
| Scheie syndrome | SGSH, NAGLU, | |
| Sanfilippo syndrome A, B, C, and D | HGSNAT, GNS GALNS | |
| Morquio syndrome A | GLB1 | |
| Morquio syndrome B | ARSB | |
| Maroteaux-Lamy syndrome | GUSB HYAL1 | |
| Sly syndrome | | |
| Natowicz syndrome | | |
| Alpha manosidosis | MAN2B1 | |
| Nieman Pick disease types A, B, and C | SMPD1, NPC1, NPC2 | |
| Cystic fibrosis | cystic fibrosis transmembrane conductance regulator (CFTR) | ΔF508 |
| Polycystic kidney disease | PKD-1, PDK-2, PDK-3 | |
| Tay Sachs Disease | HEXA | 1278insTATC |
| Gaucher disease | GBA | |
| Huntington's disease | HTT | CAG repeat |
| Neurofibromatosis types 1 and 2 | NF-1 and NF2 | CGA−>UGA−>Arg1306Term in NF1 |
| Familial hypercholesterolemia Cancers | APOB, LDLR, LDLRAP1, and PCSK9 | |
| Chronic myeloid leukemia (CML) | BCR-ABL ASXL1 | fusion |
| Acute myeloid leukemia (AML) | Chromosome 11q23 or t(9; 11) | translocation |
| Osteosarcoma | RUNX2 | |
| Colorectal cancer | EPHA1 | |
| Gastric cancer, melanoma | PD-1 | |
| Prostate cancer | Androgen receptor | |
| Cervical cancer | E6, E7 | |
| Glioblastoma Neurological disorders | CD | |
| Alzheimer's disease | NGF | |
| Metahchromatic leukodystrophy | ARSA | |
| Multiple sclerosis | MBP | |
| Wiskott-Aldrich syndrome | WASP | |
| X-linked adrenoleukodystrophy | ABCD1 | |
| AACD deficiency | AADC | |
| Batten disease | CLN2 | |

TABLE 1-continued

| Exemplary disorders and corresponding mutations | | |
| --- | --- | --- |
| Disease | Gene | Mutation |
| Canavan disease | ASPA | |
| Giant axonal neuropathy | GAN | |
| Leber's hereditary optic neuropathy | MT-ND4 | |
| MPS IIIA | SGSH, SUMF1 | |
| Parkinson's disease | GAD, NTRN, TH, AADC, CH1, GDNF, AADC | |
| Pompe disease | GAA | |
| Spinal muscular atrophy type 1 | SMN | |

Drug Screening

In one example, the method is used to screen drugs (e.g., therapeutic compounds) to determine their effect on introducing mutations into the genome, or for their ability to repair DNA. For example, the method can including incubating or treating the non-dividing cells with one or more test agents (e.g., before or during step 18 of FIG. 1A), and the effect of the one or more test agents on DNA repair determined.

In one example, the method is used to determine if a therapeutic agent is having the desired effect on a subject. For example, following treatment, non-dividing cells can be obtained from the subject and analyzed with the disclosed methods. For example, changes in DNA repair response can be measured in quiescent cancer stem cells obtained from a patient previously treated with a chemotherapy or other cancer treatment. For example, the method can be performed on quiescent cancer stem cells obtained from a patient within 1 hour, within 2 hours, within 4 hours, within 12 hours, within 24 hours, within 48 hours, or within 72 hours of being treated with a chemotherapy or other cancer treatment.

Example 1

Materials and Methods

This example describes the materials and methods used to generate the results described in the Examples below.

Cell Culture

H1 and H9 ESCs were cultured on Matrigel (R&D Cultrex Reduced Growth Factor BME, 3433-005-01) in StemMACS iPSC-Brew XF (Miltenyi Biotech Order no, 130-104-368). Differentiated cells were manually removed, and cells were then passaged with Gentle Cell Dissociation Reagent (StemCell Technologies Catalog #07174) in the presence of Y-27632 ROCK inhibitor (ROCKi).

To generate induced neurons, ESCs were dissociated into small colonies and infected with lentivirus containing doxycycline inducible NEUROG2 (lentiUNGrv, Addgene #127288) (Schafer et al., *Nat Neurosci* 22:243-255, 2019). After three days, cells were selected with 0.5 µM puromycin for several days, and subsequently passaged as described above with selection on the days following splitting. Stable ESC lines (H1- and H9-UNG) were banked in Cryostor (StemCell Technologies Catalog #07930) after three post-viral passages.

To generate ESC-iNs, cells were thawed, expanded, and reselected with puromycin. When sufficiently confluent, cells were monolayers with TrypLE Express (ThermoFisher 12604013) in the presence of ROCKi. The following day 2 µg/mL doxycycline was added to the media to induce the expression of Ngn2. On day 3, cells were again monolayered with TrypLE and ROCKi, but transitioned into BrainPhys® based neural maturation media (Stem Cell Technologies Catalog #05790; NMM; BrainPhys, N2, B27, BDNF, GDNF, dbcAMP, Laminin, and doxycycline). On day 5, cells were dissociated into single-cells with TrypLE and counted. ESC-iNs were then plated at a density of ~600-700 k cells/well onto poly-ornithine/laminin coated 6-well plates in the presence of ROCKi and 2 µM AraC (SigmaAldrich C1768). After 2 days, media was completely exchanged, and cells were subsequently supplemented with fresh NMM every 3-4 days. On day 21 post-induction, cells were used for experiments following a complete media exchange. For all Repair-Seq experiments, ESC-iNs were fed 10 µM EdU for 24 hr.

Single-Molecule Super Resolution Imaging

H9 ESC-iNs were generated and plated on polyornithine and laminin coated 8-well ibidi chambers and allowed to mature to 21 days post-doxycycline induction. They were then fed 10 µM EdU for 4 days and fixed with 4% paraformaldehyde for 10 minutes. They were subsequently washed twice with DPBS and blocked overnight at 4° C. with blocking solution (Reid et al., *Proc Natl Acad Sci USA* 112: E2575-2584, 2015). The samples were then labeled with Alexa Flour 647 azide via a copper catalyze azide alkyne cycloaddition click reaction for 30 minutes at room temperature (ThermoFisher #C10337). The cells were washed twice with blocking solution to remove unconjugated dyes and blocked again overnight at 4° C. They were then stained for Map2ab (ab32454) for 1 hour at room temperature, followed by two washes with blocking solution to remove unbound antibody. Secondary antibody conjugated to Alexa Fluor 568 was applied for 1 hour at room temperature, followed by two washed with blocking solution to remove unbound secondary antibody. ESC-iNs (identified via Map2ab staining) were then imaged with a Zeiss Elyra super-resolution microscope for at least 4000 frames in imaging buffer containing (10 mM Tris HCl pH 8.0, 10 mM NaCl, 0.5 mg/mL glucose oxidase, 40 ug/mL catalase, 10% w/v glucose, 100 mM 2-aminoethanethiol) (Dempsey et al., *Nat Methods* 8:1027-36, 2011). Images of EdU were reconstructed with QuickPALM (Henriques et al., *J. Nat Methods* 7:339-340, 2010).

Repair-Seq

Repair-Seq NGS libraries were prepared by harvesting 2-5 µg of genomic DNA (gDNA) from ~500-750,000 ESC-iNs with a Thermo Fisher Scientific Dynabeads MyOne Silane genomic DNA extraction kit (Thermo Fisher

37002D). Purified gDNA was fragmented with a Covaris m220 Focused ultra-sonicator (Target BP: 450, Peak Incident Power (W): 50, Duty Factor: 10%, Cycles per Burst: 200, Treatment Time (s): 65) to sizes between 350-450 bp as measured by an Agilent TapeStation. Sheered fragments were then cleaned with AMPure XP beads (1:1.4 v:v ratio) and resuspended in nuclease free water. A 30-minute Click reaction was performed using a ThermoFisher Click-iT EdU imaging kit (#C10337), where Alexa Fluor 647 was replaced with 0.1 mM Biotin-TEG-azide (Barry & Associates #BT1085). The reaction was then cleaned with AMPure XP beads (1:1.4 v:v ratio) and resuspended in 20 μL of nuclease free water. The Clicked gDNA fragments (2×250 ng by Qubit measurement) were then assembled in NGS sequencing libraries using the SwiftBio Accel-NGS 2S Plus DNA library kit (Catalog No. 21096). Prior to PCR amplification, the assembled libraries were bound to 10 QuickPALM L T1 streptavidin coated Dynabeads (ThermoFisher 65601) for 30-minutes in a buffer containing 5 mM Tris pH 7.5, 0.5 mM EDTA, and 1M NaCl. Following binding, the beads were washed twice with the same buffer containing 0.01% Tween-20 (Rao et al., *Cell* 159:1665-80, 2014). Following this, beads were washed with low EDTA Tris HCl (10 mM Tris HCl, 0.01 mM EDTA and finally resuspended in 20 μL of low EDTA Tris HCl. They were then amplified according to the SwiftBio Accel-NGS 2S protocol with dual indexes. Libraries were pooled and loaded onto an Illumina NextSeq 500 and read to a depth of ~18M paired end reads/sample. Repair-Seq was performed on 2 H1 and 2 H9 ESC-iN samples.

RNA-Seq

RNA was isolated with Trizol LS (ThermoFisher 10296010) and Zymogen Direct-zol extraction columns (R2050). RNA quality was measured using an Agilent Tape Station, and 400 ng of input RNA was then assembled into libraries using an Illumina TruSeq Stranded Total RNA kit (20020596). Libraries were pooled and subsequently sequenced on an Illumina NextSeq 500 to a depth of ~63M paired end reads/sample. RNA-Seq was performed on 2 H1 and 2 H9 ESC-iN samples.

ATAC-Seq

ATAC-Seq was performed as previously described (Gosselin et al., *Science* 356: eaal3222, 2017). Briefly, ESC-iNs (~100,000 cells) were lysed in 50 μL lysis buffer (10 mM Tris-HCl pH 7.5, 10 mM NaCl, 3 mM MgCl$_2$, 0.1% IGEPAL, CA-630, in water) on ice and nuclei were pelleted by centrifugation at 500 RCF for 10 min. Nuclei were then resuspended in 50 μL transposase reaction mix (1× Tagment DNA buffer (Illumina 15027866), 2.5 μL Tagment DNA enzyme I (Illumina 15027865), in water) and incubated at 37° C. for 30 min on a PCR cycler. DNA was then purified with Zymo ChIP DNA concentrator columns (Zymo Research D5205) and eluted with 11 μL of elution buffer. DNA was then amplified with PCR mix (1.25 μM Nextera primer 1, 1.25 μM Nextera primer 2-bar code, 0.6×SYBR Green I (Life Technologies, S7563), 1×NEBNext High-Fidelity 2×PCR MasterMix, (NEBM0541)) for 9 cycles, run on an 10% TBE gels (Life Technologies) for size selection of fragments (165-250 bp), and were single-end sequenced for 51 cycles on an Illumina HiSeq 4000 (Illumina, San Diego, CA)

ChIP-Seq

ChIP-Seq was performed as previously described (Nott et al., *Science* 366:1134-9, 2019). ESC-iNs (~500,000 cells) were cross-linked at room temperature for 10 min with 1% formaldehyde. Next, ESC-iNs were incubated for 5 min at room temperature with glycine to a final concentration of 0.125M. Cells were washed three times with 1% BSA, and cell pellet was stored at −80° C. until further processing.

Frozen ESC-iNs were resuspended in 130 ml lysis buffer (10 mM Tris-HCl pH 7.5, 100 mM NaCl, 1 mM EDTA, 0.5 mM EGTA, 0.1% Na-Deoxycholate, 0.5% N-Lauroylsar-cosine, 1× protease inhibitors), transferred to microtubes with an AFA Fiber (Covaris, MA) and placed on ice. Samples were sonicated using a Covaris E220 focused-ultrasonicator (Covaris, MA) for 240 secs (Duty: 5, PIP: 140, Cycles: 200, AMP/Vel/Dwell: 0.0). Samples were adjusted to 250 ml with 1% Triton X-100, centrifuged at 21,000×g for 10 mins and the pellet was discarded. 1% of the sample was stored at −20° C. for DNA input control. For ChIP, the following were added and rotated at 4° C. overnight: 25 ml Protein G Dynabeads and H3K27ac antibody (2 ml serum; Active Motif, 39135). Dynabeads were washed 3 times with Wash Buffer 1 (20 mM Tris-HCl pH 7.4, 150 mM NaCl, 2 mM EDTA, 0.1% SDS, 1% Triton X-100), three times with WB3 (10 mM Tris-HCl pH, 250 mM LiCl, 1 mM EDTA, 1% Triton X-100, 0.7% Na-Deoxycholate) and three times with TET (10 mM Tris-HCl pH 8, 1 mM EDTA, 0.2% Tween®-20 surfactant). Dynabeads were washed once with TE-NaCl (10 mM Tris-HCl pH 8, 1 mM EDTA, 50 mM NaCl) in PCR tubes and resuspended in 25 ml TT (10 mM Tris-HCl pH 8, 0.05% Tween®-20 surfactant). Input samples were adjusted to 25 ml with TT and libraries were generated in parallel with ChIP samples. Library NEBNext End Prep and Adaptor Ligation were performed using NEB-Next Ultra II DNA Library Prep kit (New England BioLabs) according to manufacturer instructions using barcoded adapters (NextFlex, Bio Scientific). Libraries were PCR amplified for 14 cycles with NEBNext High Fidelity 2×PCR MasterMix (New England BioLabs, NEBM0541). Libraries were size selected for 200-400 bp fragments by gel extraction (10% TBE gels, Life Technologies) and were single-end sequenced for 51 cycles on an Illumina HiSeq 4000 (Illumina, San Diego, CA).

Hi-C

Hi-C libraries were constructed from ~1M ESC-iNs as described previously (Dixon et al., *Nat Genet* 50:1388-98, 2018). Briefly, adherent ESC-iNs were fixed for 10 minutes at room temperature while still attached to tissue culture plates by addition of formaldehyde directly to the cell culture media at a final concentration of 1%. The reaction was quenched for 5 minutes at room temperature with addition of 2.5M Glycine to a final concentration of 0.2M. Cells were washed twice with 1×DPBS and removed with a cell scraper. The samples were pelleted, the supernatant removed, and samples were then frozen at −80° C. until ready for further processing. Hi-C libraries were prepared using the in situ method with the MboI restriction enzyme. The libraries were sequenced the Illumina HiSeq X platform. Hi-C experiments were performed on 1 H1 and 1 H9 ESC-iN sample each.

RIME

H9 ESC-iNs labelled with EdU for 4 days were cross-linked at room temperature by addition of 1% formaldehyde in DPBS for 8 min followed by quenching with 125 mM Tris-HCl pH 8.0. The cells were then washed with 1 mg/mL BSA in DPBS three times and snap frozen. Chromatin was prepared and processed for RIME as previously described (Mohammed et al., *Nat Protoc* 11:316-326, 2016), with modifications. All subsequent buffers were supplemented with protease inhibitor tablets (Roche #05056489001). Briefly, cells were lysed with lysis buffer 1 (50 mM HEPES pH 7.4, 140 mM NaCl, 1 mM EDTA, 10% glycerol, 0.5% NP-40, and 0.25% Triton X-100) and washed with lysis buffer 2 (10 mM Tris-HCl pH 8.0, 200 mM NaCl, 1 mM EDTA, and 0.5 mM EGTA). The nuclei were resuspended in CuAAC click reaction buffer (10 mM CuSO4, 5 mM THPTA, 1 mM Biotin-TEG-Azide, 125 mM sodium ascorbate) or PBS (no click control) and incubated at room temperature for 45 min in the dark. The biotin-labeled (or non-labeled control) nuclei were collected via centrifugation, washed three times in cold DPBS, and resuspended in TF sonication buffer (300 mM NaCl, 10 mM Tris-HCl pH 8.0, 1 mM EDTA pH 8.0, 0.1% Na-deoxycholate, 0.1% SDS, 1% Triton X-100, 0.25% sarkosyl), then sheared for 4 min with a probe tip sonicator (Epishear, pulse 1 s on/1 s off, 25% amplitude) on a cold block. Sonicated lysates were clarified by centrifugation (16,000 g, 10 min, 4° C.) and incubated overnight at 4° C. with Streptavidin T1 Dynabeads (Thermo Fisher #65601) with rocking. Chromatin from 200 million ESC-iNs were pooled for each individual pulldown. Beads were washed 10 times with cold RIME-RIPA buffer (50 mM HEPES pH 7.6, 1 mM EDTA, 0.7% wt/vol sodium deoxycholate, 1% vol/vol NP-40 and 0.5 M LiCl) and twice with 100 mM triethylammonium bicarbonate (TEAB) buffer. Proteins were reduced/alkylated and trypsin was digested on the beads. RIME experiments were repeated 2 times.

Mass Spectrometry

Samples were precipitated by methanol/chloroform and redissolved in 8 M urea/100 mM TEAB, pH 8.5. Proteins were reduced with 5 mM tris(2-carboxyethyl)phosphine hydrochloride (TCEP, Sigma-Aldrich) and alkylated with 10 mM chloroacetamide (Sigma-Aldrich). Proteins were digested overnight at 37° C. in 2 M urea/100 mM TEAB, pH 8.5, with trypsin (Promega). Digestion was quenched with formic acid, 5% final concentration.

The digested samples were analyzed on a Fusion Orbitrap tribrid mass spectrometer (Thermo). The digest was injected directly onto a 30 cm, 75 um ID column packed with BEH 1.7 um C18 resin (Waters). Samples were separated at a flow rate of 200 nL/min on a nLC 1000 (Thermo). Buffer A and B were 0.1% formic acid in water and 0.1% formic acid in 90% acetonitrile, respectively. A gradient of 1-25% B over 110 min, an increase to 40% B over 10 min, an increase to 90% B over 10 min and held at 90% B for a final 10 min was used for 140 min total run time. The column was re-equilibrated with 15 ul of buffer A prior to the injection of sample. Peptides were eluted directly from the tip of the column and nanosprayed directly into the mass spectrometer by application of 2.5 kV voltage at the back of the column. The Orbitrap Fusion was operated in a data-dependent mode. Full MS scans were collected in the Orbitrap at 120K resolution with a mass range of 400 to 1500 m/z and an AGC target of $4e^5$. The cycle time was set to 3 sec, and within this 3 sec the most abundant ions per scan were selected for CID MS/MS in the ion trap with an AGC target of $1e^4$ and minimum intensity of 5000. Maximum fill times were set to 50 ms and 100 ms for MS and MS/MS scans respectively. Quadrupole isolation at 1.6 m/z was used, monoisotopic precursor selection was enabled, and dynamic exclusion was used with an exclusion duration of 5 sec. Protein and peptide identification were done with Integrated Proteomics Pipeline-IP2 (Integrated Proteomics Applications). Tandem mass spectra were extracted from raw files using RawConverter and searched with ProLuCID against Uniprot human database (He et al., *Anal Chem* 87:11361-7, 2015; Xu et al., *J Proteomics* 129:16-24, 2015). The search space included all fully tryptic and half-tryptic peptide candidates. Carbamidomethylation on cysteine was considered as a static modification. Data were searched with 50 ppm precursor ion tolerance and 600 ppm fragment ion tolerance. Identified proteins were filtered to using DTASelect and utilizing a target-decoy database search strategy to control the false discovery rate to 1% at the protein level (Tabb et al., *J Proteome Res* 1:21-26 (2002; Peng et al., *J Proteome Res* 2:43-50, 2003).

Analysis of Repair-, ATAC-, and ChIP-Seq Data

Blue Collar Bio (BCBio) was used for core NGS data functions including genome alignment and transcriptomics.

To align sequencing reads to the human genome draft 38 (hg38), FASTQ files for each sample were de-multiplexed for R1 and R2. Ends containing adapters and barcodes were trimmed using Atropos (Patro et al., *Nat Methods* 14, 417-419, 2017) (—quality-base 33—format fastq—overlap 8—no-default-adapters—no-cache-adapters), and bowtie2 v. 2.3.5 was used for alignment (Langmead et al., *Nat Methods* 9, 357-359, 2012). Following alignment to hg38, duplicate reads were marked with biobambam2 version 2.0.87 [gitlab.com/german.tischler/biobambam2], peaks were called using MACS2 version 2.1.2 (-f BAMPE -g 3217346917-B) (Zhang et al., *Genome Biol* 9, R137, 2008), and bedgraph browsers were generated with Homer (Heinz et al., *Mol Cell* 38, 576-589, 2010) and visualized with Integrated Genomics Viewer (Robinson et al., Integrative genomics viewer. *Nat Biotechnol* 29, 24-26, 2011). The following tools were also used by BCBio in the ChIP-Seq/ ATAC-Seq pipelines: FastQC (www.bioinformatics.babraham.ac.uk/projects/fastqc/), Bedtools (Quinlan and Hall, *Bioinformatics* 26, 841-842, 2010), Sambamba (Tarasov et al., *Bioinformatics* 31, 2032-2034, 2015), Samtools (Li et al., *Bioinformatics* 25, 2078-2079, 2009) and MultiQC [github.com/ewels/MultiQC].

Peak and Bam files were loaded into R (www.r-project.org), and the R/Bioconductor and its associate packages were employed for most analysis functions (Gentleman et al., *Genome Biol* 5, R80, 2004; Huber et al., *Nat Methods* 12, 115-121, 2015). Peaks from H1 and H9 ESC-iNs were compared using R/DiffBind to measure associated reads in peaks (Ross-Innes et al., *Nature* 481, 389-393, 2012). Peaks that exhibited FDR<0.05 with DiffBind/DESeq2 across biological replicates were scored as being reproducible and subsequently used for further analysis (Love, W. Huber, S. Anders, *Genome Biol* 15, 550, 2014)). Peaks were annotated in R using the ChipSeeker and ChipPeakAnno Packages. Peak intersections, relative distance, and distance calculations were performed using bedtools (Ross-Innes et al., *Nature* 481, 389-393, 2012) intersect, reldist, and closest respectively. TSS plots were made using deepTools directly from bed files (deeptools.readthedocs.io/en/develop/content/about.html).

To identify de novo sequence motifs, the meme-chip functions from MEME Suite package was used with the parameter -meme-nmotifs 20. De novo identified motifs were annotated against the *Homo Sapiens* Comprehensive Model Collection (HOCOMOCO) database, version v11 hocomocoll.autosome.ru. Discriminative Regular Expression Motif Elicitation (DREME) output from the meme-chip function are used specifically and give propriety over Multiple Em for Motif Elicitation (MEME) output in the analysis. The intersection of ATAC- and H3K27Ac ChIP-Seq peaks was used for background correction (Machanick et al., *Bioinformatics* 27:1696-7, 2011; Bailey, *Bioinformatics* 27:1653-9, 2011).

Gene ontology enrichment was performed with G-profiler (Raudvere et al. *Nucleic Acids Res* 47:W191-W198, 2019).

Analysis of RNA-Seq Data

RNA-Seq analysis was performed by calling Salmon in BCBio (Patro et al., *Nat Methods* 14:417-419, 2017). Reads were aligned using HISAT2 (Xu et al., *J Proteomics* 129: 16-24, 2015).

Analysis of Hi-C Data

Raw Hi-C data was aligned with BWA to the hg38 reference genome and post-processed as previously described (Dixon et al., *Nat Genet* 50:1388-1398, 2018). Contact files were generated from the filtered, deduplicated alignments and converted to hic files using Juicer tools (Durand et al., *Cell Syst* 3, 95-98, 2016). The matrices were normalized using hiccups CPU using GW_KR normalization at resolutions of 5 kb, 10 kb, and 25 kb. Eigenvectors were calculated using juicer tools at a resolution of 50 kb. Hi-C TAD call were generated at a resolution of 40 kb as previously described (Dixon et al., *Nature* 485, 376-380, 2012). Loops calls, eigenvector tables, and TAD calls were exported, and analysis was performed in R. Hi-C figures were generated with the Juicebox browser (Durand et al., *Cell Syst* 3, 99-101, 2016).

Analysis of RIME Data

Proteins were considered streptavidin-enriched hits if corresponding total spectral counts in duplicate click samples were 1.33-fold enriched compared to duplicate controls (spec count cutoff=3), with filtering out of structural proteins. These hits (79 proteins) were analyzed for functional interactions against the STRING database (string-db.org). Each protein from this list was analyzed for differential abundance in the Consensus Brain Protein Coexpression Study consisting of 419 proteomics samples from dorsolateral prefrontal cortex across 4 patient cohorts (Banner, BLSA, ACT, MSSB) grouped into cognitively normal controls, asymptomatic AD, and AD patients. Source data (syn21441771) were downloaded as log 2(abundance), age, sex, and PMI-regressed, batch- and site-corrected median (near-zero) centered, with outliers removed. One-way ANOVA with a post-hoc Tukey test was performed to assess significance for differential protein abundance among the three groups, and a hypergeometric test was used to quantify significance of the overlap between differentially abundant proteins in the Consensus dataset and differentially enriched proteins in the RIME dataset.

Example 2

Figures 1C, 1D:
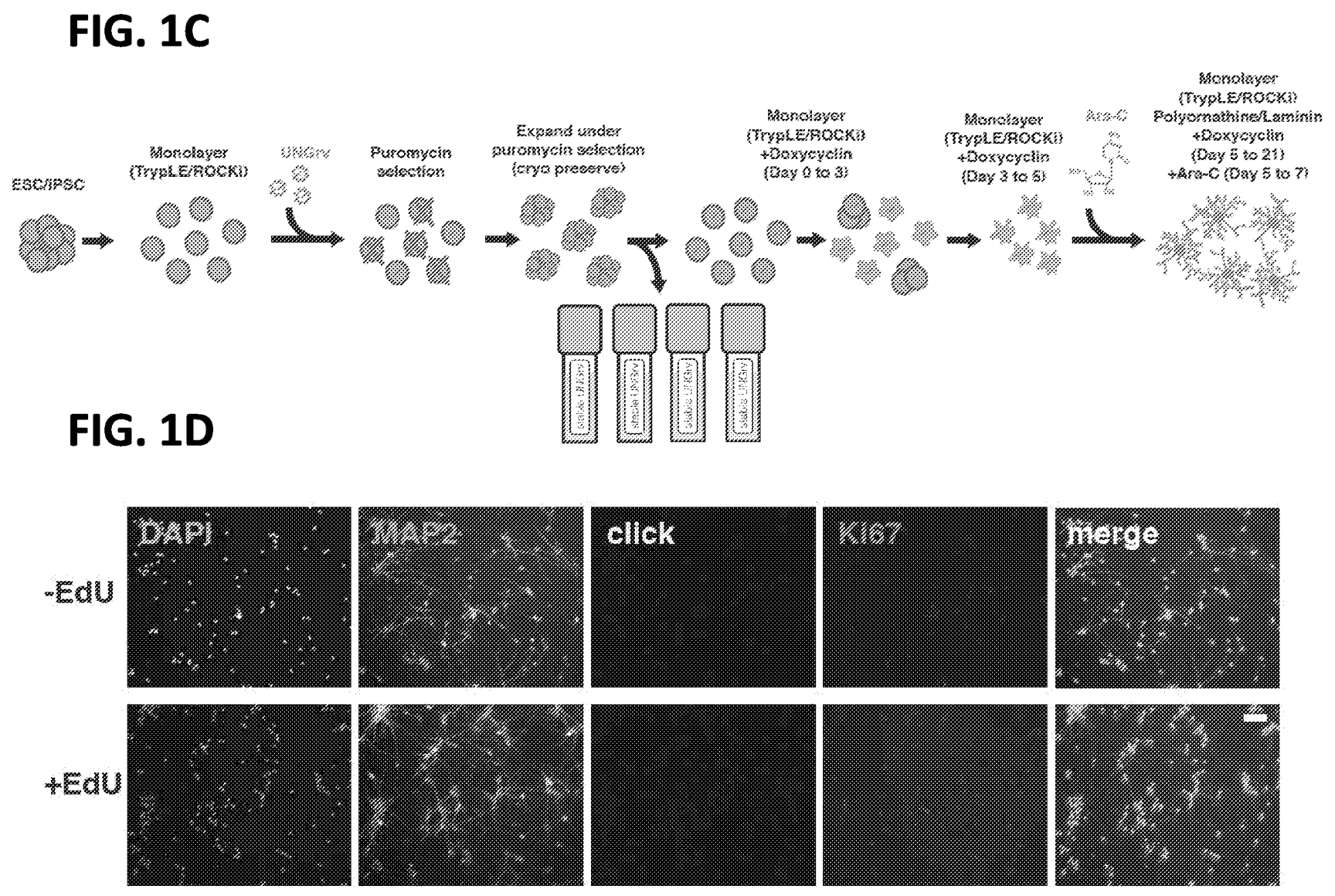
Figures 2A, 2B:
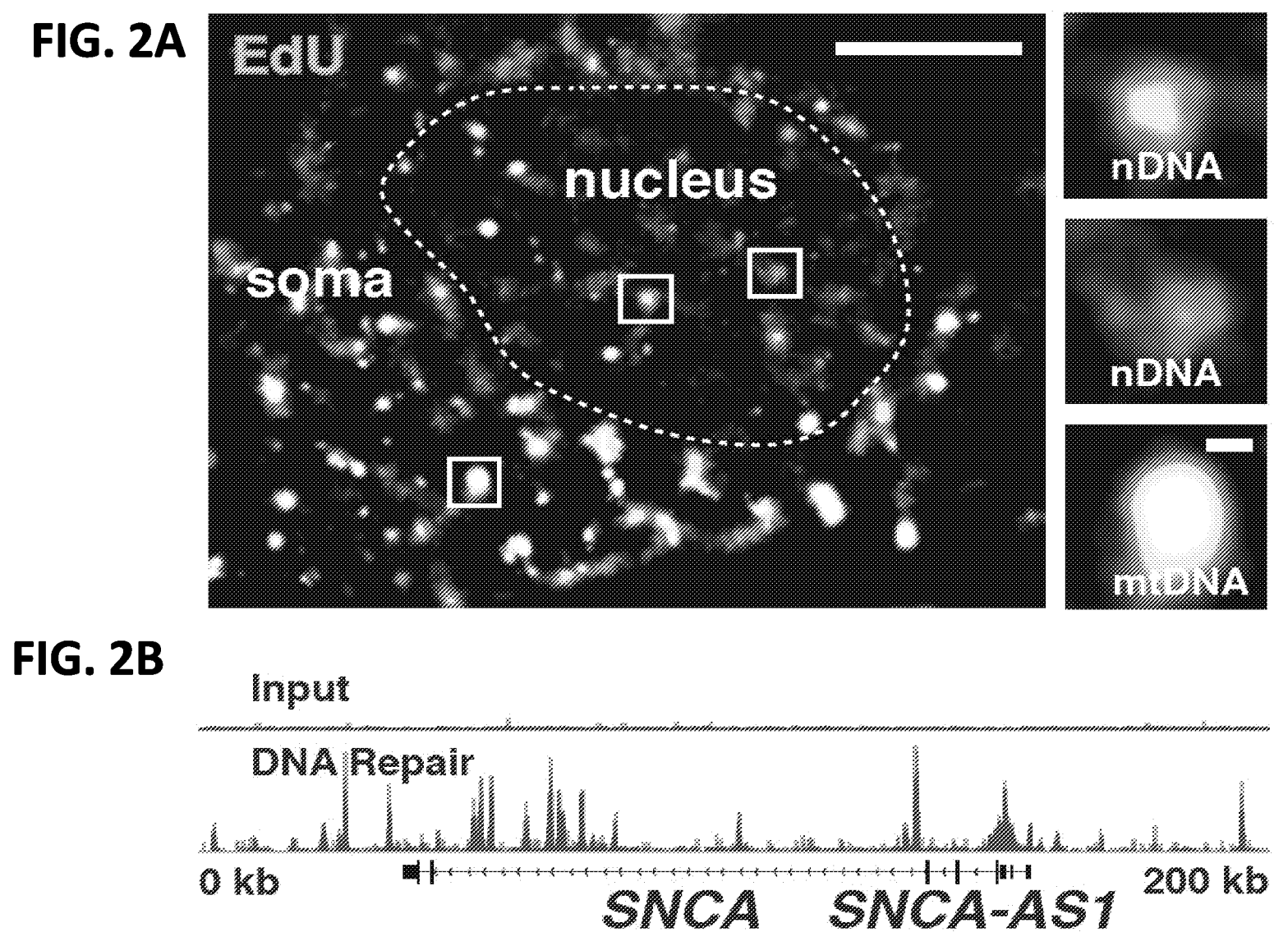
Figures 3A, 3B:
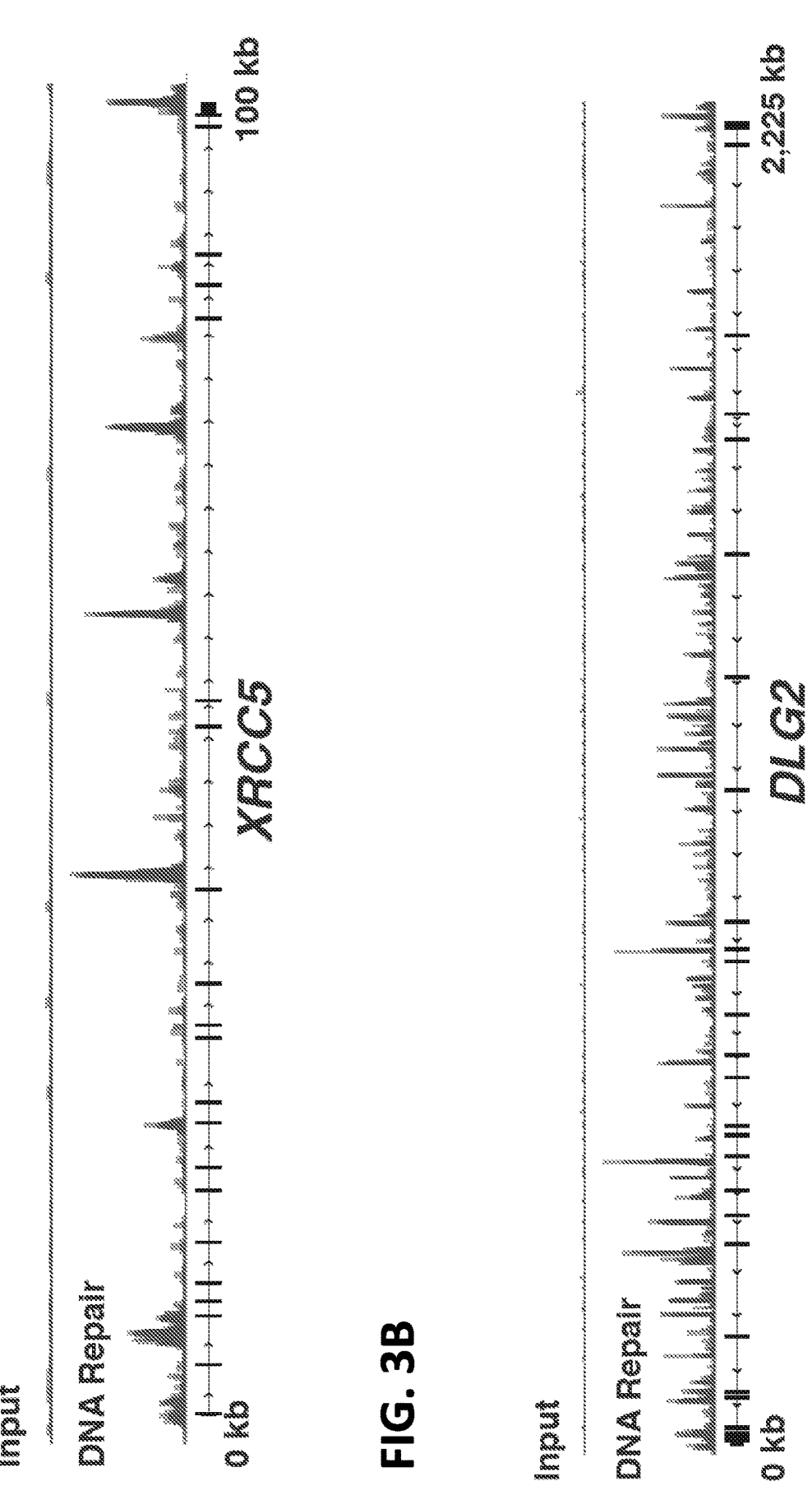
FIGS. 3A-3H. Genomics of stable genome repair hotspots in post-mitotic human neurons. (A-B) Further examples of DNA repair hotspots in the XRCC5 and DLG2 loci. (C) Histogram of genome repair hotspot peak widths. (D) Reproducibility of Repair-Seq peaks in normalized read counts for biological replicates of H1 and H9 ESC-iNs. (E) Genome map of DNA repair hotspots in ESC-iNs. (F) Detailed view of DNA repair hotspots (purple) and gene density (green) on Chromosome X. (G) Genome annotations for DNA repair hotspots show distributions primarily in promoters, gene bodies, and intergenic regions. (H) Fold-enrichment of DRHs over predicted genome distribution. Scale bars are 5 microns and 250 nm.

Incorporation of EdU into Post-Mitotic Neuron Genomes by DNA Repair can be Mapped by Next-Generation Sequencing To better understand genome integrity in neurons, a sequencing method capable of capturing the genomic locations of all DNA repair based on the incorporation of the click chemistry nucleoside analog, EdU (5-ethynyl-2'-deoxyuridine) was developed. Neurons can incorporate radioactive thymidine into their genomes following DNA damage or under normal resting conditions by DNA repair pathways (Sanes and Okun, J Cell Biol 53:587-590, 1972; Korr and Schultze, Exp Brain Res 74, 573-8, 1989). To test this finding in human neurons, embryonic stem cell induced neurons (ESC-iNs) were generated that assume a fully post-mitotic cortical neuron identity 21 days after the addition of doxycycline via the expression of NEUROG2 (FIGS. 1C, 1D) (Mertens et al., *Cell Stem Cell* 17:705-718, 2015), Schafer et al., Nat Neurosci 22:243-255, 2019). These ESC-iNs were used to confirm the incorporation of EdU into the genome by using single-molecule localization-based super-resolution imaging of EdU in human embryonic stem cell-induced neurons (ESC-iNs) incubated with EdU for 24 hrs (FIG. 2A) (Schafer et al., Nat Neurosci 22:243-255, 2019; Huang et al., *Annu Rev Biochem* 78: 993-1016, 2009). These neurons have EdU clusters in both the nucleus and cytosol, where EdU is incorporated into mitochondrial nucleoids during mitochondrial biogenesis. To identify the genomic locations where EdU molecules incorporated into the nuclear genome of ESC-iNs fed EdU for 24 hrs, next-generation sequencing libraries were enriched for fragments that contain EdU using click chemistry addition of a biotin epitope (FIG. 1B). This strategy is similar to the targeted sequencing of newly synthesized DNA containing nucleoside analogs to identify the locations of replication forks (Hansen et al., Proc Natl Acad Sci USA 107:139-44, 2010; Rivera-Mulia et al., Proc Natl Acad Sci USA 114:E10972-E10980, 2017). This new method, termed "Repair-Seq," revealed many locations across the neuronal genome that exhibited substantial EdU enrichment over comparable whole-genome sequencing to the same depth (FIGS. 2B, 3A, 3B).

Figures 3C, 3D:
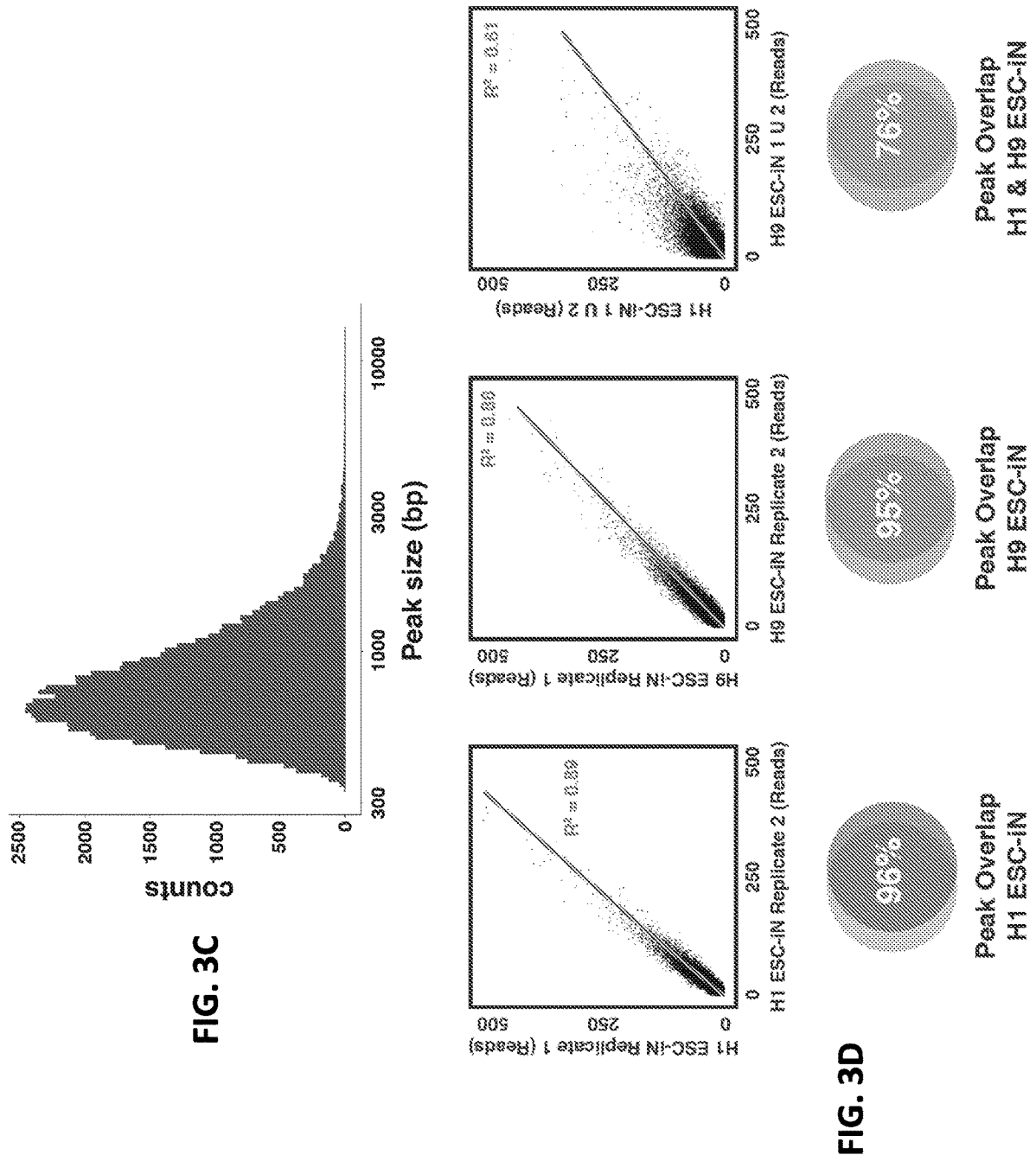
Figures 3E, 3F, 3G:
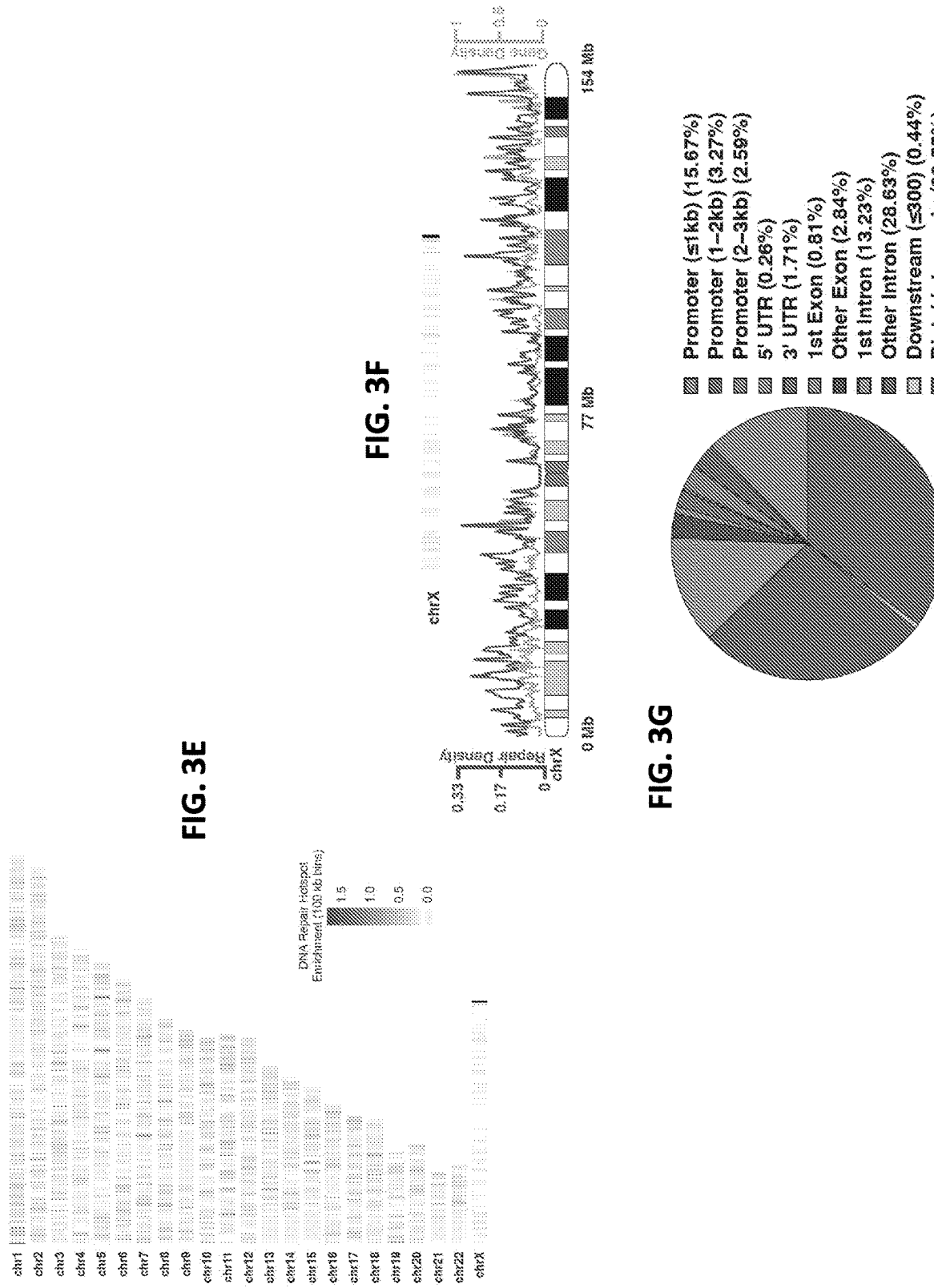
Figure 3H:
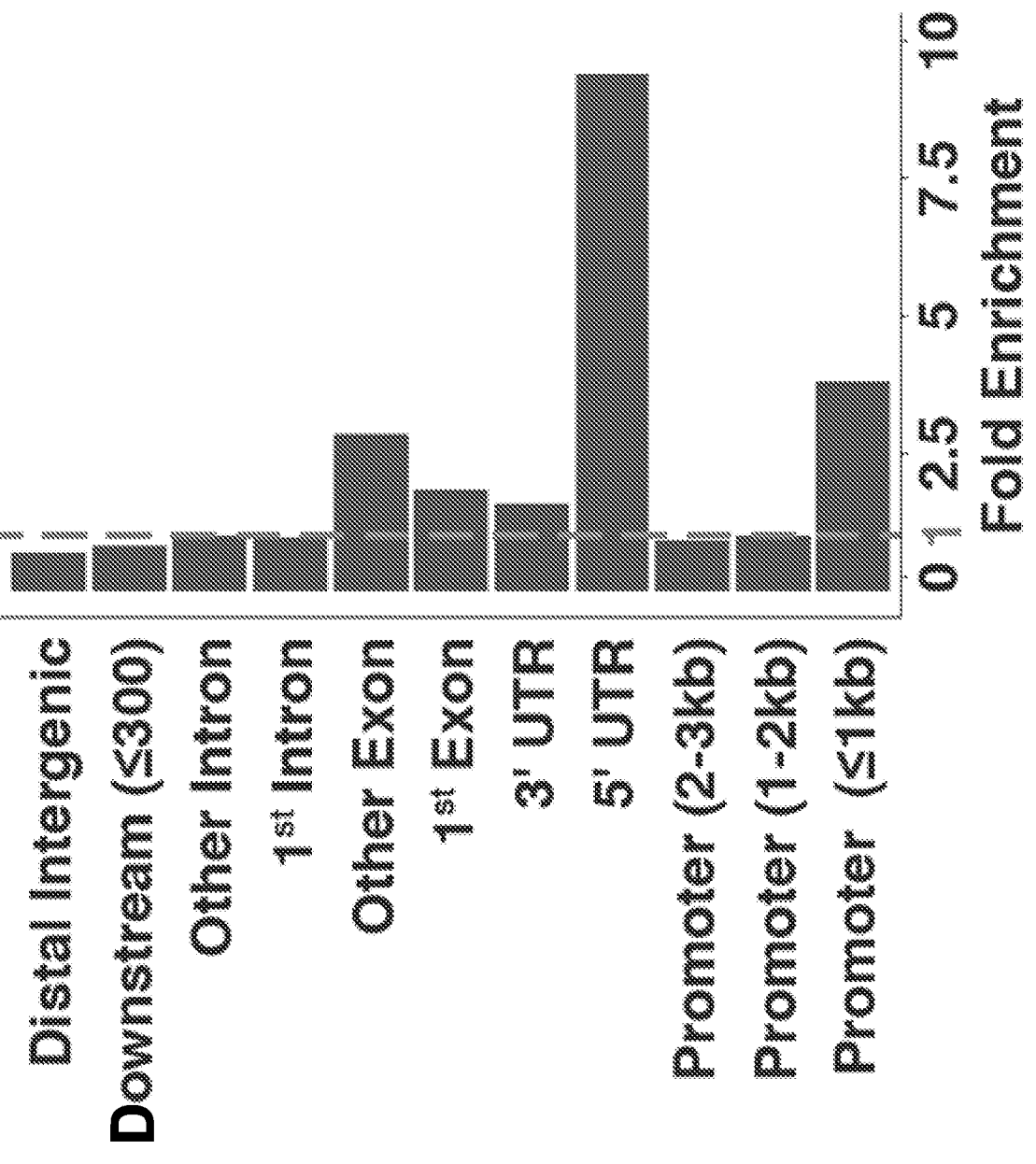

EdU enriched sites appear as well-defined peaks ~500 base pairs (FIG. 6D), so a genome peak calling algorithm (Zhang et al., *Genome Biol* 9:R137, 2008) was applied to the data, finding 87,000 total peaks across two H1 and two H9 ESC-iN biological replicates (all sequencing experiments unless otherwise noted are the results of 2 H1 and 2 H9 samples). DiffBind and DESeq2 were used to define differential peaks between biological replicates, finding good agreement (FIG. 3D) (Ross-Innes et al., Nature 481:389-393, 2012; Love et al., Genome Biol 15:550, 2014). Similar analysis of all Repair-Seq samples resulted in 61,178 reproducible peaks in common for both lines, covering ~1.6% of the genome (FIGS. 3C-3D). As these sites exhibit relative enrichment for DNA repair over the rest of the genome, they are termed DNA repair hotspots (DRHs). These DRHs are distributed throughout the genome on all chromosomes, and appear to be enriched in promoters ≤, 5'UTRs, and gene bodies (FIGS. 3E-3H). To exhibit such a stable signal in this assay, recurrence across lines and replicates indicates that these locations are frequently repaired in the sequenced ESC-iN population. Additionally, this approach is not specific for a particular DNA repair pathway, instead capturing a heterogeneous mix of all repair pathways capable of nucleotide incorporation (e.g., single-strand break, DSB, base excision, nucleotide excision, and transcription coupled repair).

Example 3

Chromatin Accessibility Controls the Placement of DNA Repair Hotspots

Figures 4A, 4B, 4C, 4D:
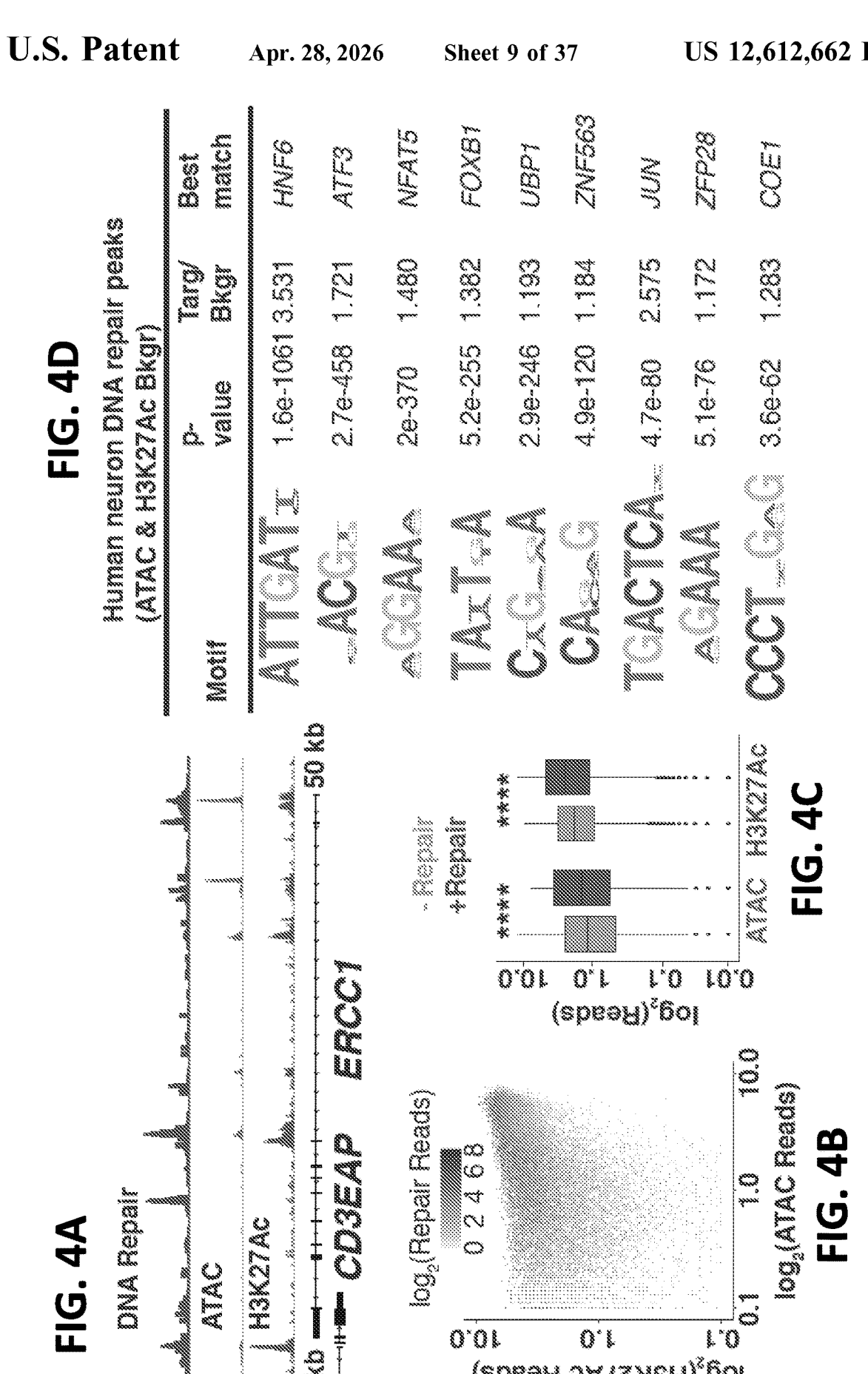
FIGS. 4A-4D. Chromatin accessibility controls the placement of DNA repair hotspots. (A) Repair-, ATAC-, and H3K27Ac ChIP-Seq data at the ERCC1 locus demonstrate overlap between DNA repair, chromatin accessibility, and histone acetylation. (B) Scatter plot of Repair-Seq normalized read counts compared to ATAC and H3K27Ac normalized read counts. (C) Box plots of ATAC and H3K27Ac peaks with and without DNA repair. (D) DNA sequence motifs identified de novo and predicted as enriched in DRHs relative to randomized sequence. **** p-value<2.2e-16 Kruskal-Wallis test.
Figure 5A:
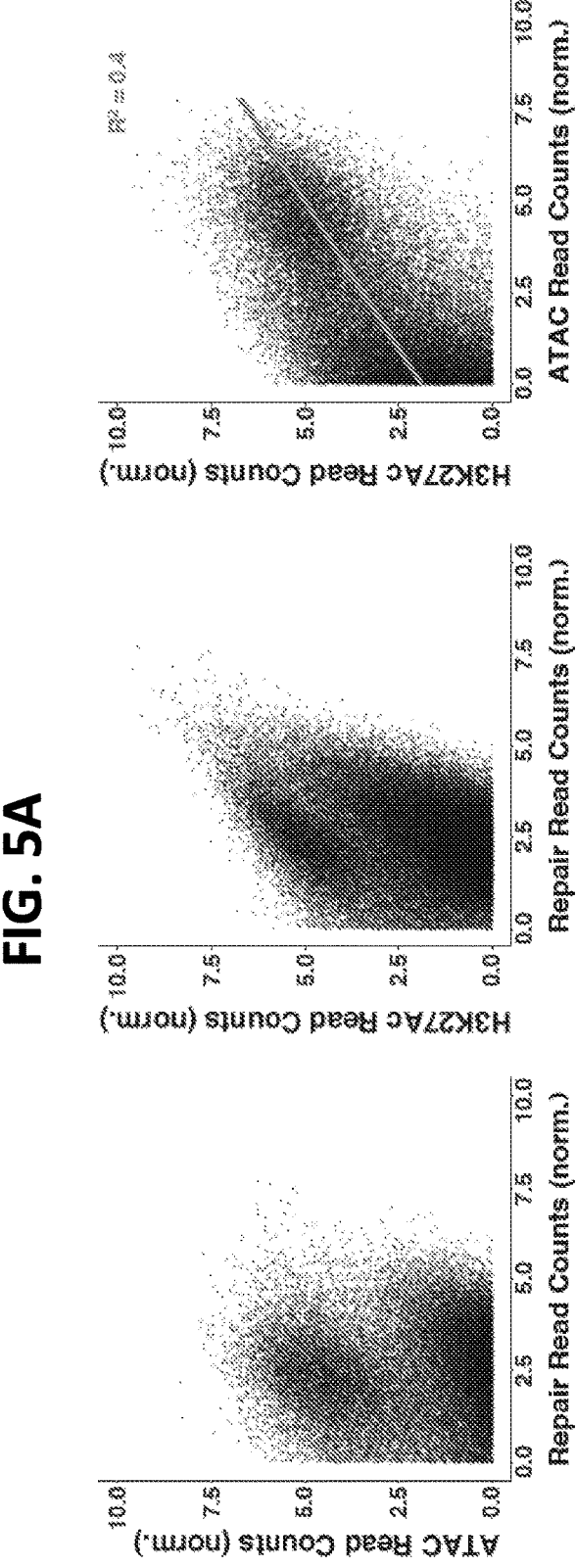
Figure 5B:
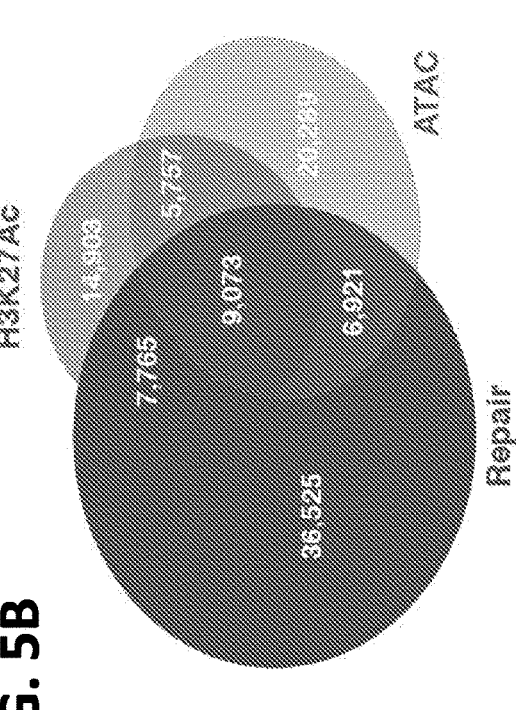
Figures 5C, 5D:
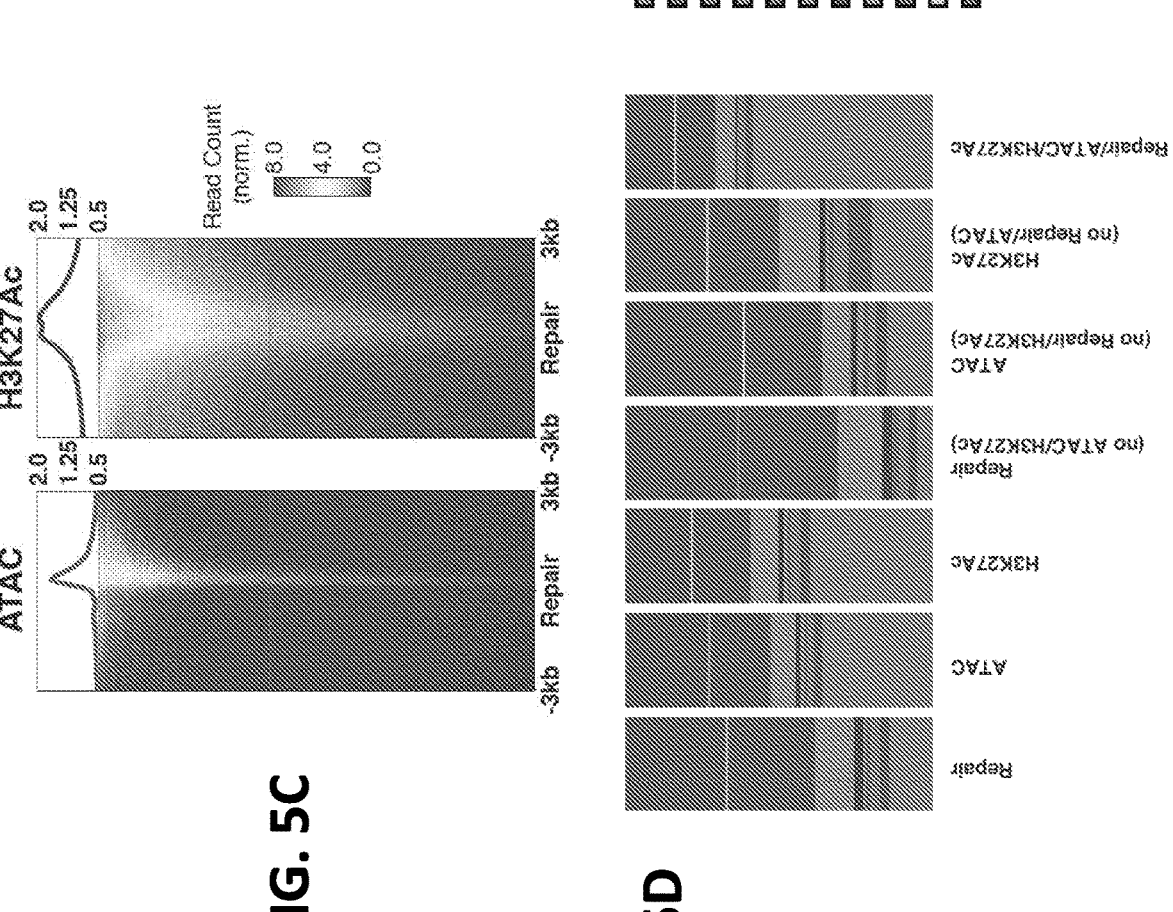

Given the stability and reproducibility of these DRHs, the genomic and epigenomic features that contribute to their establishment in neurons was determined. To map the locations of open chromatin and active regulatory regions in the ESC-iNs, ATAC-Seq and H3K27Ac ChIP-Seq, were performed. About 23.5% of Repair-Seq common peaks were located within these genomic regions (FIG. 4A, 5A-5B) (Buenrostro et al., Nat Methods 10:1213-8, 2013). This represents a ~15-fold enrichment over expected associations for repair and these chromatin marks. Intersecting peaks in open regions correlate with greater DNA repair signal strength (FIG. 4B) (Hauer and Gasser, Genes Dev 31:2204-21, 2017; Dabin et al., Mol Cell 62: 712-27, 2016). This conclusion is supported by evidence of ATAC and H3K27Ac sites that intersect with DRHs having more normalized reads than those lacking repair (FIG. 4C). Additionally, when Repair-Seq peaks are used as a reference and plot ATAC and H3K27Ac signal intensity, both of these marks, if not directly overlapping, are proximal to DRHs (FIG. 5C). Promoters are the predominate point of intersection for Repair, ATAC, and H3K27Ac peaks, whereas DRHs that do not associate with open chromatin are predominately located in intergenic and intronic elements of the genome (FIG. 5D).

Figure 5G:
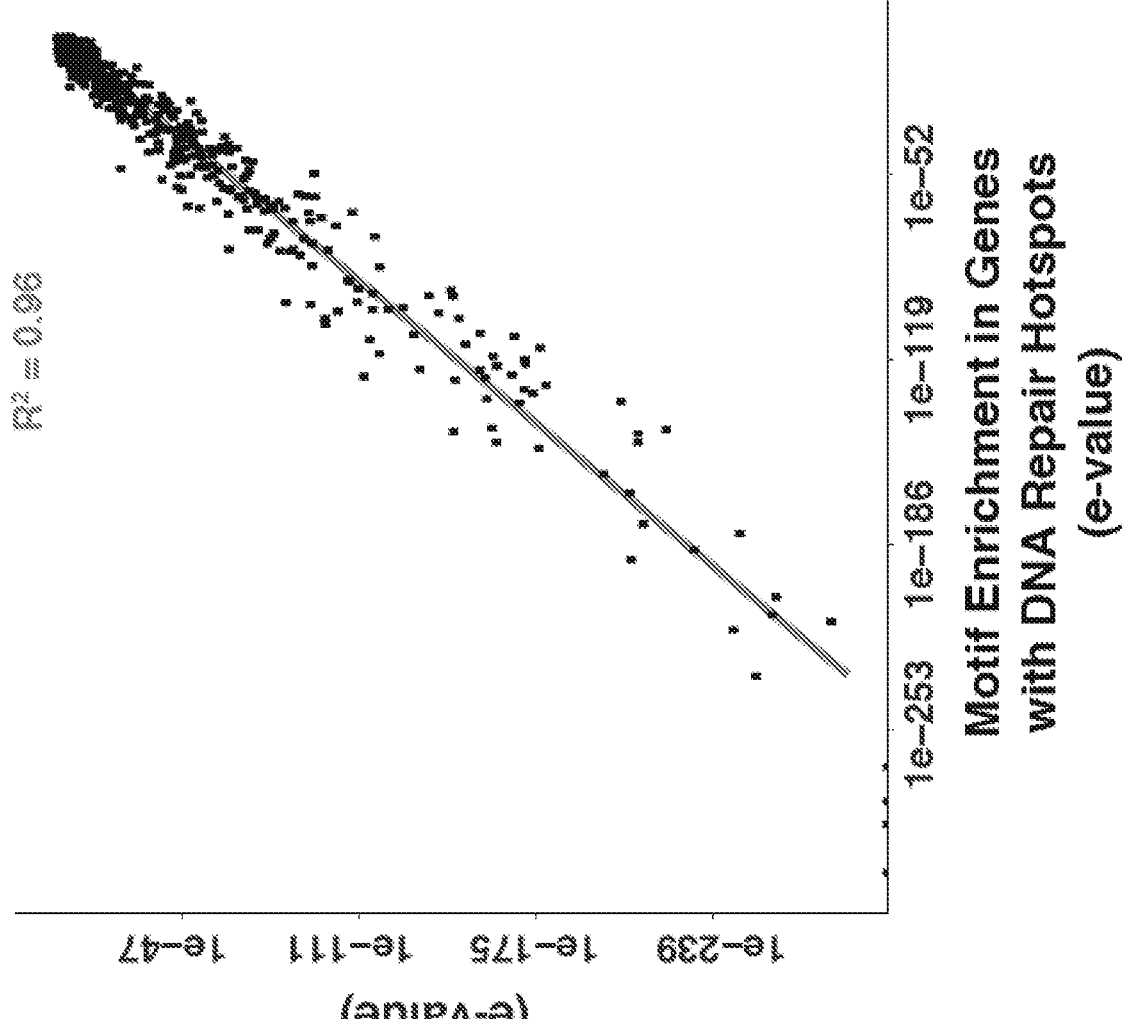

To examine the underlying contribution of the genome to the formation of DRHs, de novo DNA sequence motif analysis was performed for all peaks. DNA sequence motifs were identified, including ones associated with the factors HNF6, ATF3, NFAT5, FOXBJ, UBP1, ZNF563, JUN, ZFP28, and COE1 as being significantly enriched in Repair-Seq peaks when taking ATAC and H3K27Ac peaks as background to correct for the contributions of open chromatin. (FIGS. 4D, 5E-5F). Many of the factors associated with these motifs have roles in specifying neuronal characteristics (van der Raadt et al., Nucleic Acids Res 47:5587-5602, 2019; Hunt et al., Front Mol Neurosci 5:7, 2012; Maallem et al., Neuroscience 137:51-71, 2006). The de novo DNA repair-associated motifs were enriched in genes with DRHs, compared to genes that do not form DHRs, and it was observed that these motifs are not enriched in DRH containing genes (FIG. 5G). This lack of enrichment indicates that the establishment of DRHs could occur in other genes and that there might "organizing factors" that coordinate sites of recurrent DNA repair in non-dividing cells.

Example 4

Figures 6A, 6B:
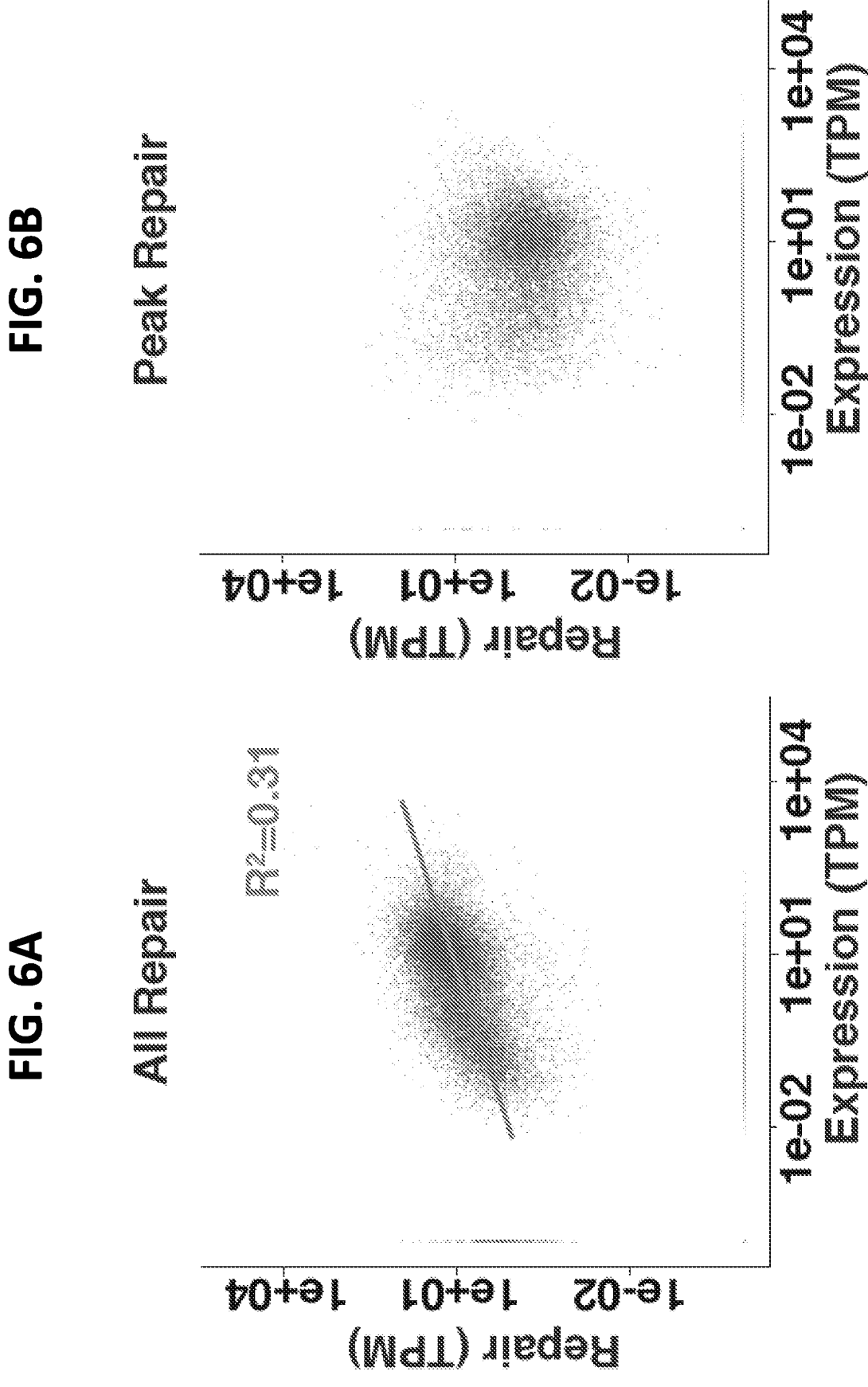
Figures 7A, 7B, 7C:
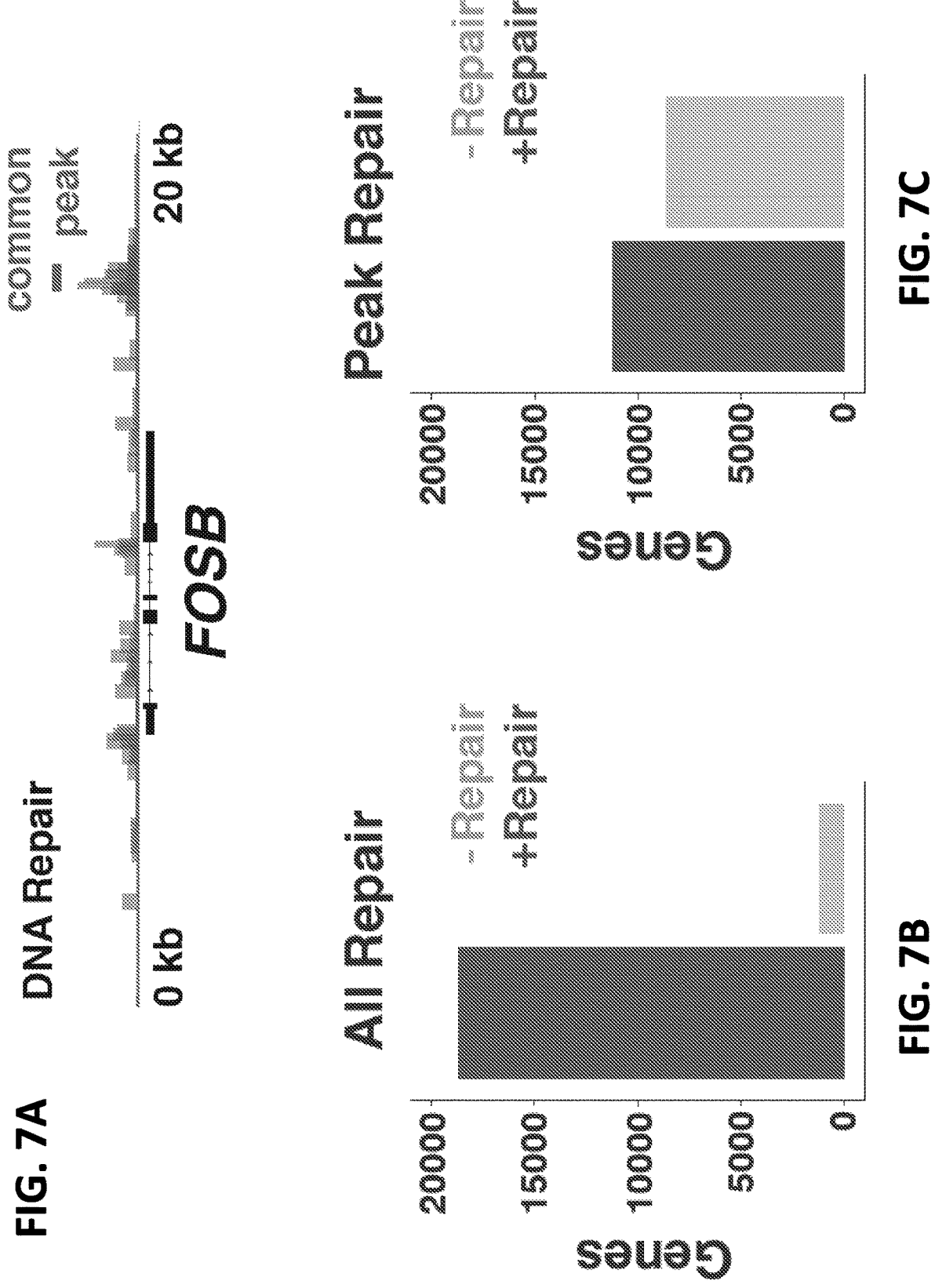
FIGS. 7A-7C. Quantification of genes with DNA repair. (A) DNA repair in FOSB locus. Bar plot displaying the number of protein-coding genes that have DNA repair-associated reads. (B) Bar plot displaying the number of protein-coding genes that have DNA repair-associated reads. (C) Bar plot displaying the number of protein-coding genes that have DNA repair-associated reads found in DNA repair hotspots.

Transcriptional Output Correlates with Total DNA Repair but not DNA Repair Hotspots Repair-Seq allowed for a direct comparison of all DNA repair- and transcription-associated reads. A majority of Repair-Seq reads (~67%) could be assigned to gene bodies using RNA-Seq pipelines (Patro et al., Nat Methods 14:417-9, 2017), with most of the neuronal transcriptome exhibiting some level of maintenance that increased with expression (FIGS. 6A, 7A-7B). This indicates that in neurons, global DNA repair is attenuated and consolidated to actively transcribed genes, presumably to suppress the accumulation of lesions and mutations (Nouspikel et al., Mol Cell Biol 20:1562-70, 2000). However, when the reads that comprise DRHs (~23% of all repair reads) were examined, many more genes lacked these recurrent DNA repair sites and no relationship to expression was found (FIGS. 6B & 7C). Almost a third of DRHs were located in intergenic regions; therefore, these could not readily be correlated with transcription of single genes.

Figures 6C, 6D:
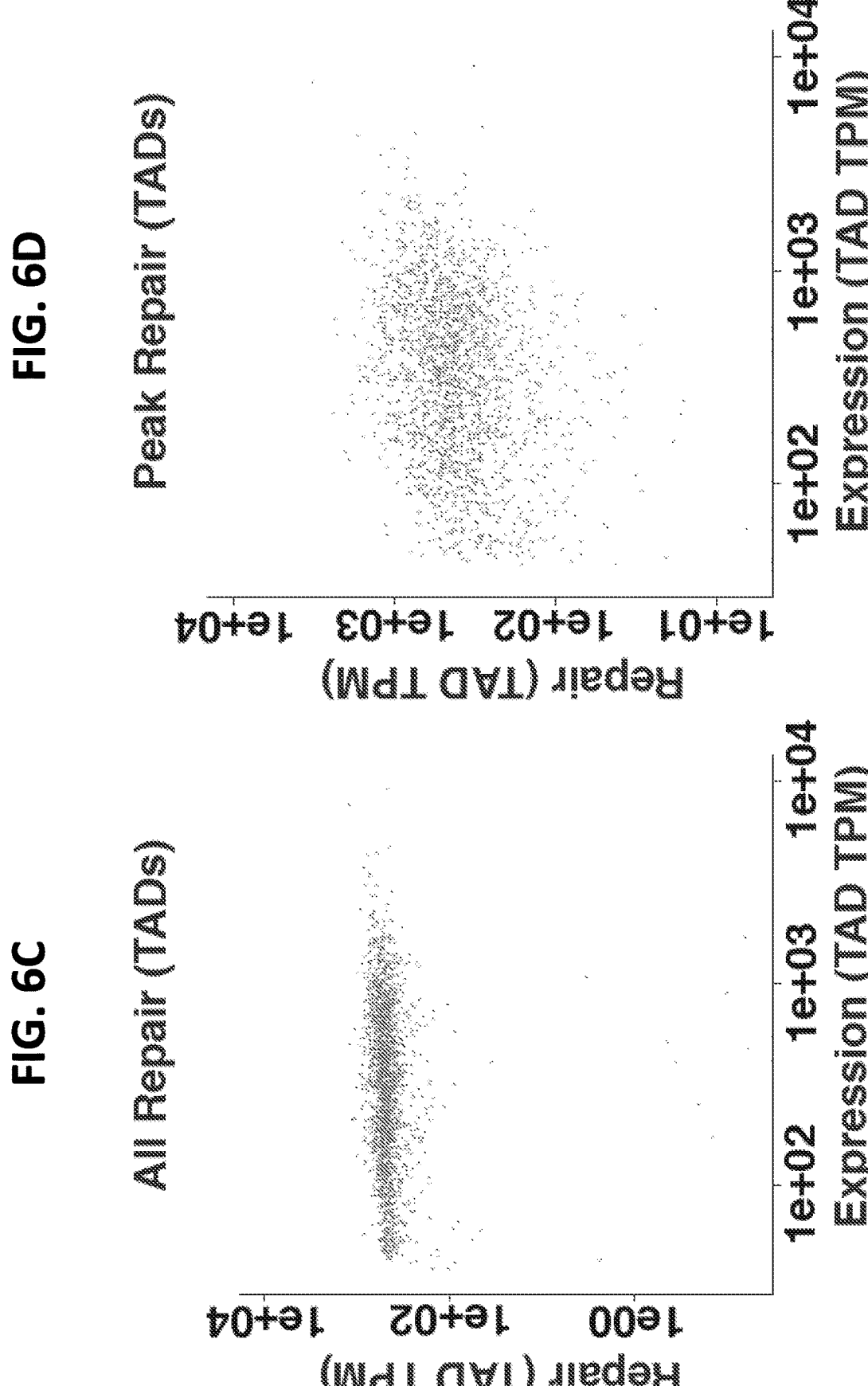
Figure 8A:
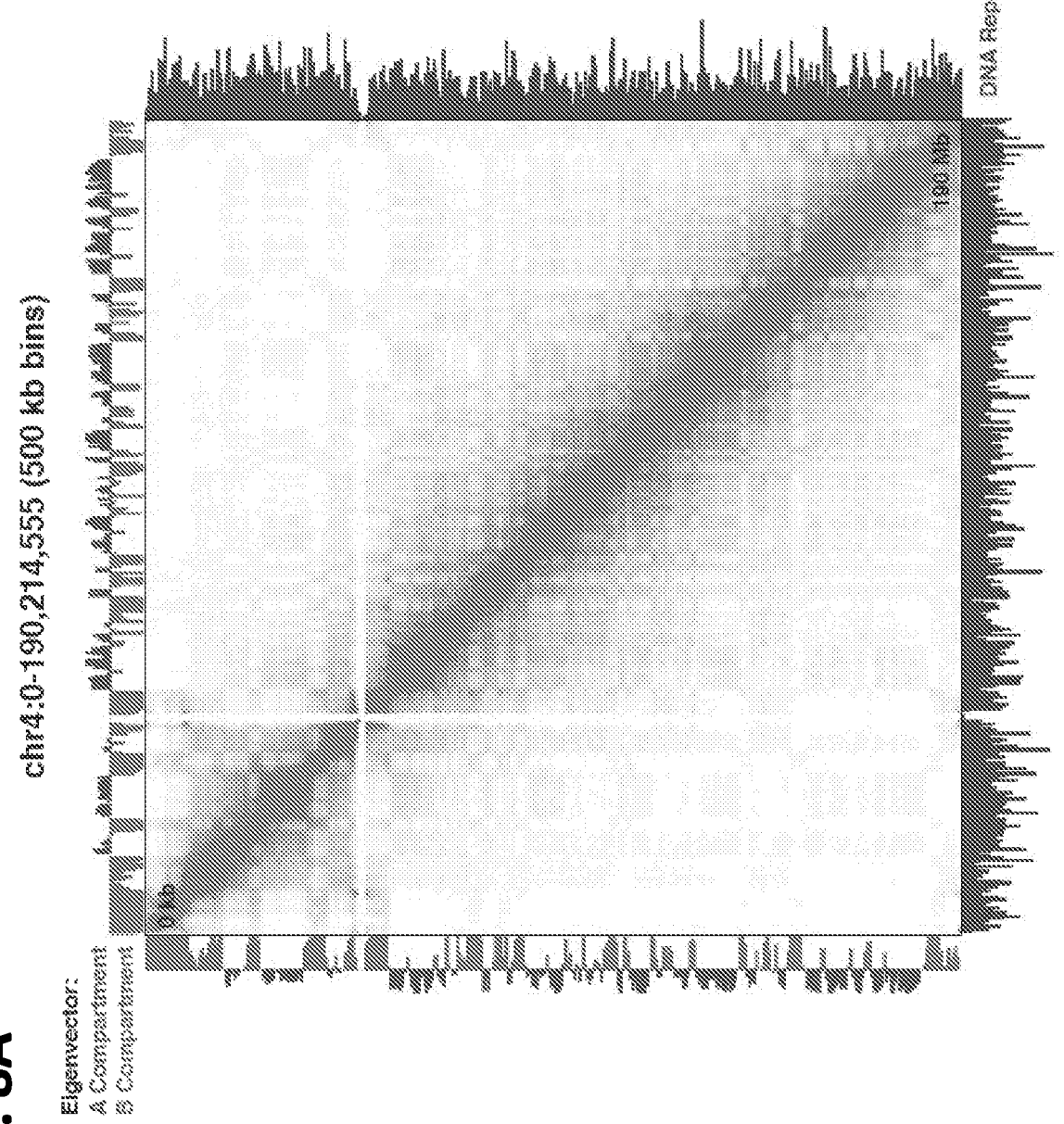
FIGS. 8A-8C. Hi-C A/B compartments are enriched for DNA repair. (A) Representative Hi-C data for chromosome 4 displaying eigenvalues corresponding to A/B compartments and DNA repair from Repair-Seq. (B) Box and scatter plots of all DNA repair associated reads compared with transcription in Hi-C A/B compartments. (C) Box and scatter plots of all DNA repair peak associated reads compared with transcription in Hi-C A/B compartments. ** p-value<2.8e-44, * p-value<8.5e-19, ** p-value<3.8e-13 by Wilcoxon test.
Figures 8B, 8C:
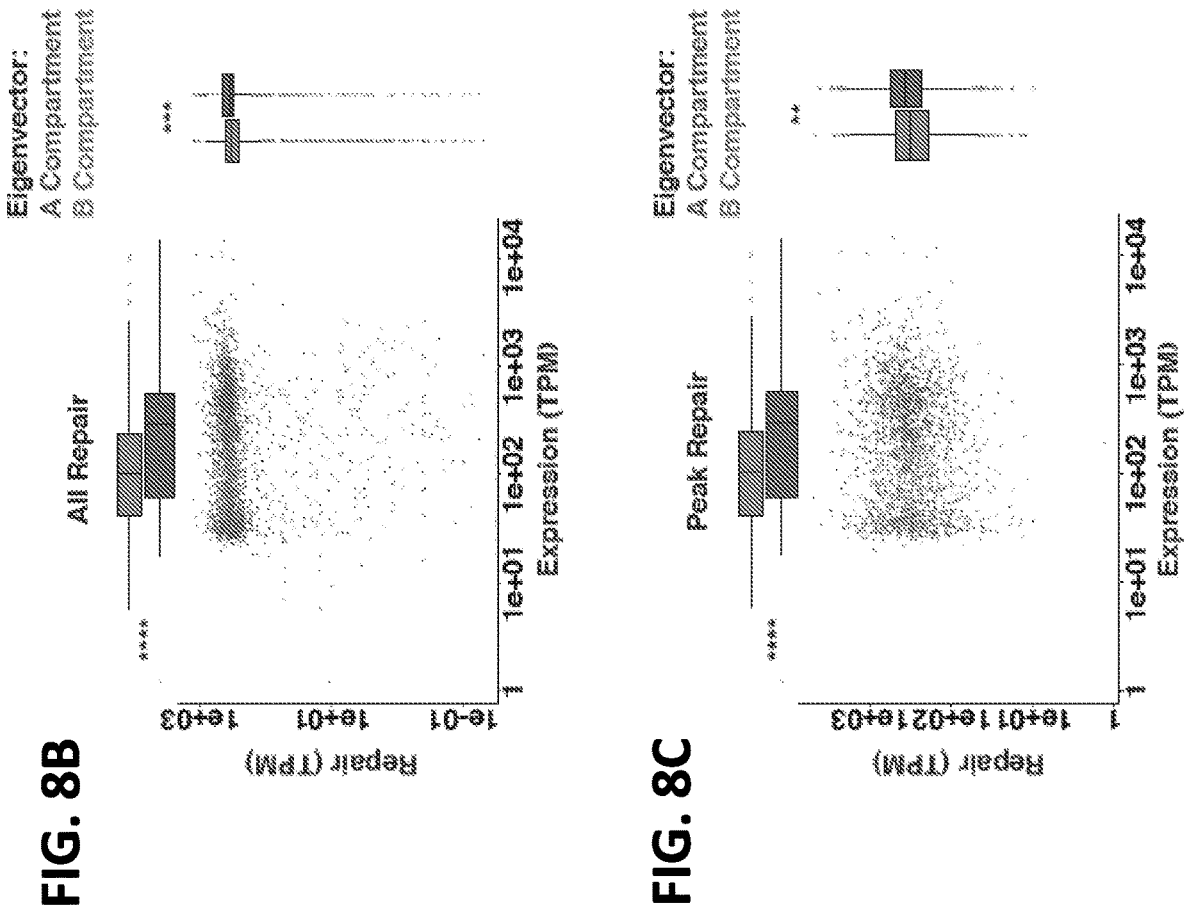
Figures 9A, 9B:
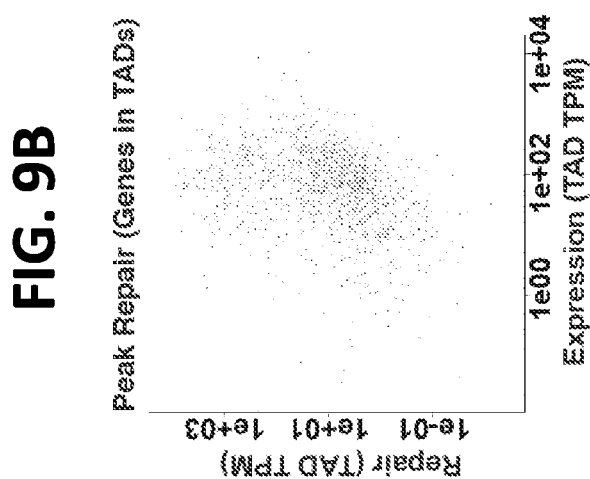
FIGS. 9A-9B. TADs are not preferentially enriched for DNA repair. (A) Representative Hi-C data from chromosome 21 displaying loop contacts, TADs, DNA repair and genes. (B) Scatter plot of DNA repair-associated reads found in SGRHs in genes compared with total expression normalized to TAD width.

To address the potential contribution of these sites to transcription-associated repair, Hi-C contact maps were generated for ESC-iNs (1 H1 and 1 H9 sample), such that intergenic peaks could be assigned to genes based on features of 3D genome organization, such as Topologically Associating Domains (TADs) (Dixon et al., Nature 485:376-380, 2012). Total DNA repair levels in most TADs were uniform (FIG. 6C). Assignment of intergenic peaks did not substantially alter the interpretation that DRHs are correlated with the levels of gene transcription (FIGS. 6D, 9A-9B). Comparing the distribution of either all DNA repair-associated reads or Repair-Seq peaks with genome wide features of 3D genome organization such as A/B compartments, enrichment of DNA repair in the "active" A compartment was observed (FIGS. 8A-8C).

Figures 6E, 6F:
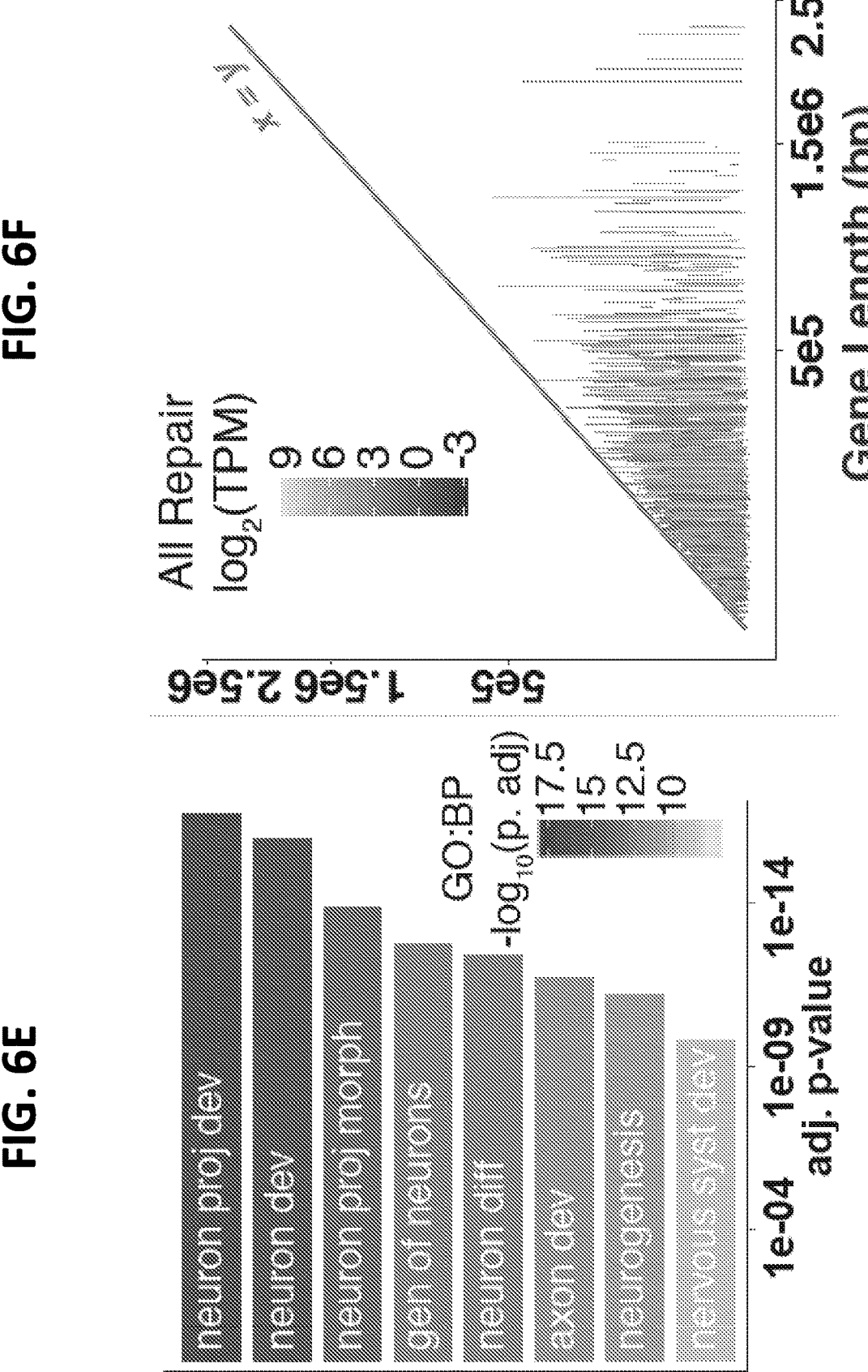
Figure 11B:
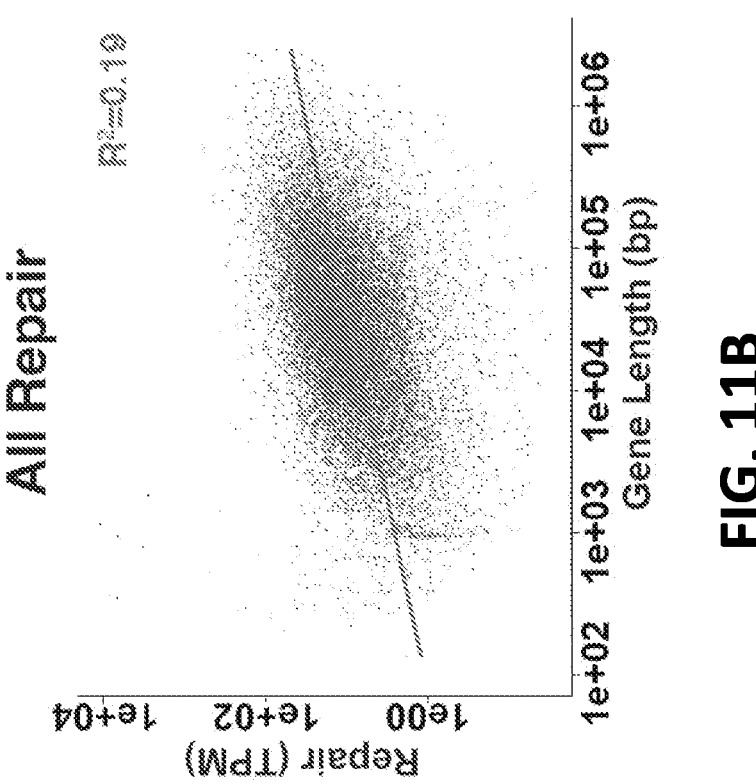
FIGS. 11A-11D. Length dependency of DNA repair hotspots. (A) Normalized transcription compared with gene length. (B) Normalized DNA repair compared with gene length. (C) Normalized DNA repair in peaks compared with gene length. (D) Number of DNA repair hotspots compared with gene length.
Figure 11A:
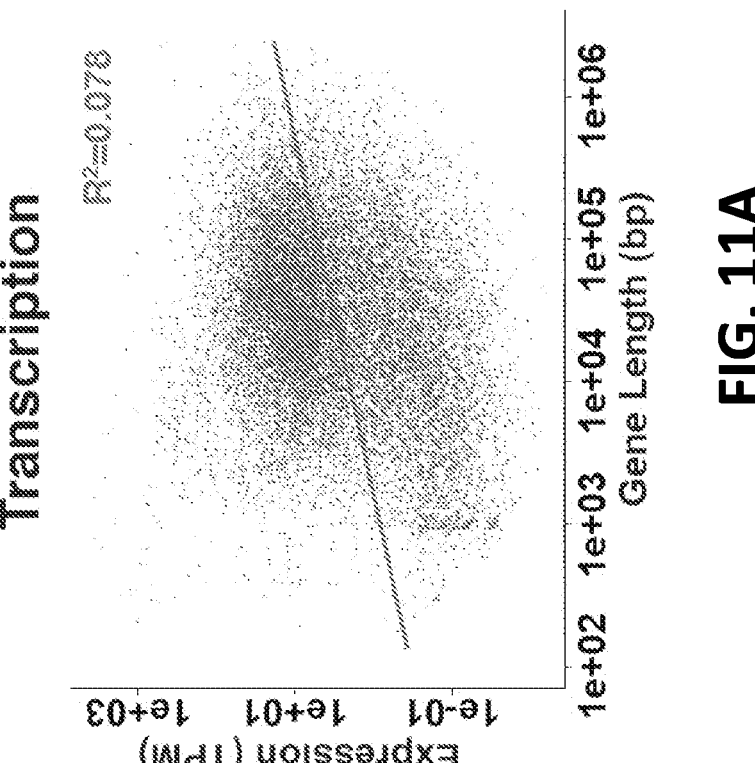
Figures 11C, 11D:
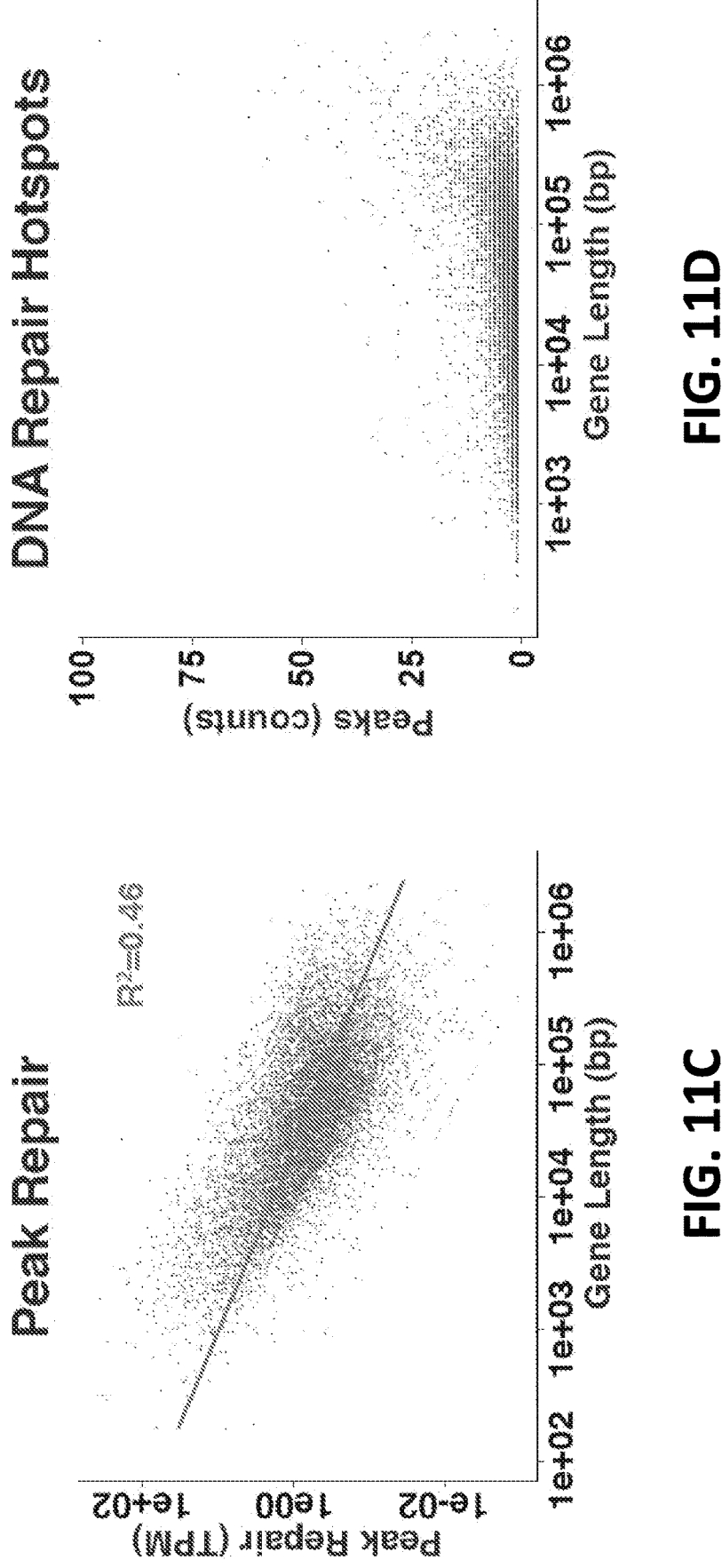

Hotspots genes were significantly enriched for specific cellular processes and are more correlated with genes essential for neuronal identity and function irrespective of expression level (e.g., DLG4, ARC, GRIA4, GRIN2B, MAP2, HOMER1) (FIGS. 6E, 10A-10B). Given that neural genes are typically quite long (Zylka et al., Neuron 86:353-5, 2015), it was determined whether gene length played a role in DRH density. Both total repair and transcription were compared to gene length. It was found that they were independent of size (FIGS. 11A-11B). However, when reads that were only from DRHs were examined in relationship to length, the total level of repair in these sites as well as total peak density paradoxically diminished as genes grew larger (FIGS. 6F, 11C-11D). These findings indicate that DRHs in neural genes might in part arise from the specific requirements of maintaining transcriptional elongation and splicing in genes containing large introns (Takeuchi et al., Cell Rep 23:1326-41, 2018).

To investigate if DRHs were linked to splicing in neurons, rapid immunoprecipitation mass spectrometry of endogenous proteins (RIME) was performed on chromatin that had undergone repair (Mohammed et al., Nat Protoc 11:316-26, 2016). ESC-iNs were labeled with EdU as in Repair-Seq, cells were fixed and nuclei were isolated. Half the samples underwent a click reaction to add a biotin epitope; the other samples were treated as a negative control for any background peptide signal. Chromatin was then sheared and pulled down via streptavidin coated beads. Following stringent washing, proteins were eluted and identified via mass spectrometry. 79 proteins enriched in the clicked samples relative to the controls were identified (Table 2).

TABLE 2

| uniprot | gene |
| --- | --- |
| Q14011 | CIRBP |
| Q13151 | HNRNPA0 |
| Q07666 | KHDRBS1 |
| O00148 | DDX39A |
| Q13838 | DDX39B |
| Q14240 | EIF4A2 |
| P07305 | H1-0 |
| Q02539 | H1-1 |
| P16403 | H1-2 |
| P16402 | H1-3 |
| P10412 | H1-4 |
| P16401 | H1-5 |
| P0C0S8 | H2AC11 |
| Q99878 | H2AC14 |
| P04908 | H2AC4 |
| P20671 | H2AC7 |
| Q9BTM1 | H2AFJ |
| Q71UI9 | H2AFV |
| P16104 | H2AFX |
| O75367 | H2AFY |
| P0C0S5 | H2AZ1 |
| Q96A08 | H2BC1 |
| P62807 | H2BC10 |
| P06899 | H2BC11 |
| O60814 | H2BC12 |
| Q99880 | H2BC13 |
| Q99879 | H2BC14 |
| Q99877 | H2BC15 |
| P57053 | H2BFS |
| P84243 | H3-3A |
| P68431 | H3C1 |
| Q6NXT2 | H3F3C |
| P62805 | H4-16 |
| P22492 | HIST1H1T |
| Q96QV6 | HIST1H2AA |
| Q93077 | HIST1H2AC |
| Q96KK5 | HIST1H2AH |
| P33778 | HIST1H2BB |
| P58876 | HIST1H2BD |
| Q93079 | HIST1H2BH |
| P23527 | HIST1H2BO |
| Q6FI13 | HIST2H2AA3 |

35

TABLE 2-continued

| uniprot | gene |
|---------|------|
| Q8IUE6 | HIST2H2AB |
| Q16777 | HIST2H2AC |
| Q16778 | HIST2H2BE |
| Q5QNW6 | HIST2H2BF |
| Q71DI3 | HIST2H3A |
| Q7L7L0 | HIST3H2A |
| Q8N257 | HIST3H2BB |
| Q16695 | HIST3H3 |
| O00479 | HMGN4 |
| P09651 | HNRNPA1 |
| P22626 | HNRNPA2B1 |
| P51991 | HNRNPA3 |
| Q14103 | HNRNPD |
| P31943 | HNRNPH1 |
| P55795 | HNRNPH2 |
| P61978 | HNRNPK |
| P14866 | HNRNPL |
| P52272 | HNRNPM |
| Q00839 | HNRNPU |
| Q1KMD3 | HNRNPUL2 |
| P54652 | HSPA2 |
| P11142 | HSPA8 |
| Q12906 | ILF3 |
| Q92945 | KHSRP |
| P43243 | MATR3 |
| Q15233 | NONO |
| Q15365 | PCBP1 |
| Q15366 | PCBP2 |
| P57721 | PCBP3 |
| P38159 | RBMX |
| Q96E39 | RBMXL1 |
| P62979 | RPS27A |
| Q9TTE1 | SERPINA3-1 |
| P23246 | SFPQ |
| P62987 | UBA52 |
| P0CG47 | UBB |
| P0CG48 | UBC |

These proteins were largely grouped into histones and RNA binding proteins (RBPs) when network analysis was performed (FIG. 6G). GO analysis of these proteins indicated that their function largely comprised DNA packaging and RNA processing (FIGS. 17A-17C). It was next determined whether these proteins were differentially enriched in age-associated neurodegenerative disease. The Consensus Brain Protein Coexpression Study dataset was used to compare protein abundance (label free quantitation; LFQ) in cognitive normal (CN), asymptomatic Alzheimer's disease (AsymptAD), and Alzheimer's disease (AD) patients. 21 of these showed differences between CN and AD patients, indicating a role for DRHs in neurological disease (FIG. 611), a significant fraction as assessed by a hypergeometric test (p-value<2.67e-10).

Figures 12A, 12B:
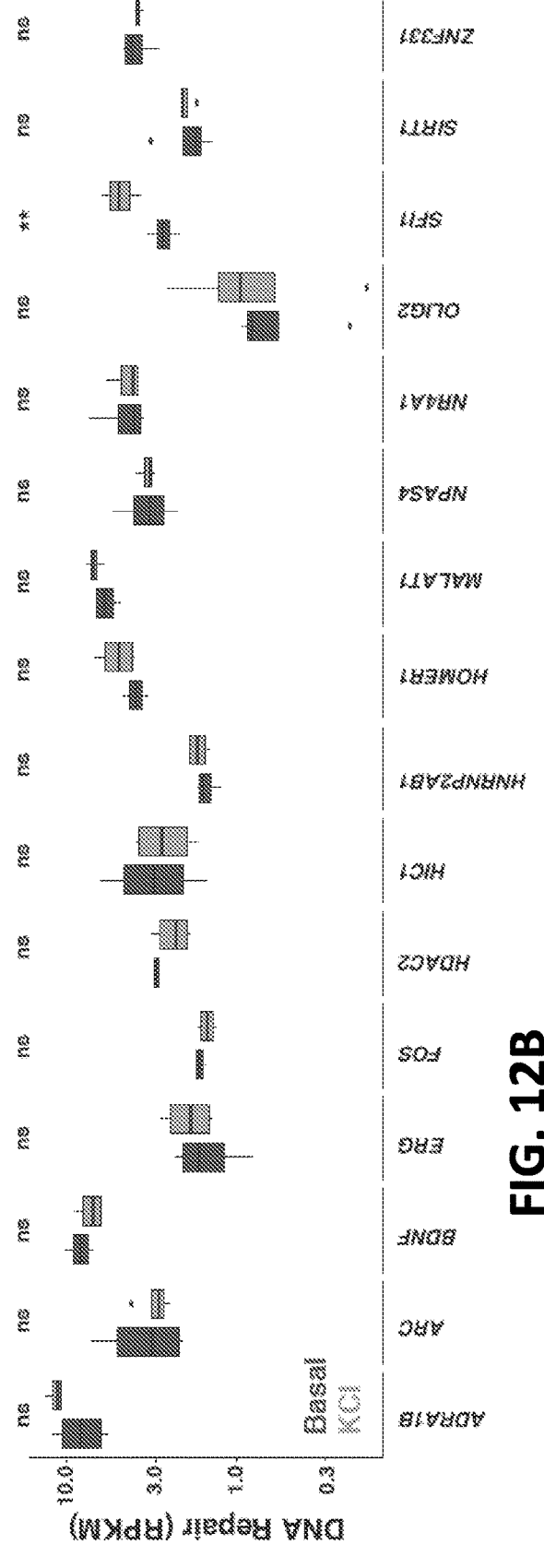
FIGS. 12A-12B. Neuronal depolarization does not increase DNA repair levels in the promoters of immediate early genes. (A) Promoter region of FOS and NPAS4 loci in basal conditions (purple) and with the addition of 50 mM KCl for 30 minutes and 24 hr of recovery (green). (B) TPM box plots for the promoters of genes thought to have activity-induced DSBs found in mouse cortical neuron culture (FOS, MALAT1, NPAS4, ERC, OLIG2, NR4A1, HOMER1, NR4A3, HDAC2, HNRNP2AB1, SIRT1) and human-specific activity-related genes (BDNF, ARC, HIC1, LINC00473, ZNF331, ADRA1B). ** p-value<0.01 by Wilcoxon test.

Prior reports suggested that neuronal activity generates DSBs and the associated DNA damage marker γH2AX (phospho-histone H2A.X Ser139) in the promoters of a small subset of immediate early genes required for learning and memory to initiate transcription in mice (Suberbielle et al., Nat Neurosci 16:613-621, 2013; Madabhushi et al., Cell 161:1592-1605, 2015). Human ESC-iNs were stimulated for 30 minutes with 50 mM KCl and then allowed 24 hrs to recover in the presence of EdU to label activity-induced DSB sites. Examination of the promoters for activity-related genes indicated that repair occurred there under steady state with no change following stimulation and recovery (FIGS. 12A-12B). The lack of elevated DNA repair at these sites indicates that there might be some species-specific differences in how these genes are transcribed (Pruunsild et al., Cell Rep 18:122-135, 2017), that their repair might be highly reliable and not incorporate new nucleotides, or that the γH2AX that is associated with activity may not be a reliable marker of DSBs (Shanbhag et al., *Acta Neuropathol Commun* 7:77, 2019)

Figure 18B:
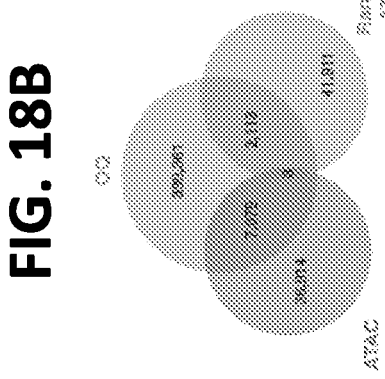
FIGS. 18A-18E. DNA G-quadruplexes at DNA repair hotspots in neuronal genomes. (A) Representative genome browser displaying Repair-Seq, ATAC-Seq, and OQ (observed G-quadruplexes). (B) Intersection of OQ with ATAC or random ATAC-peaks. (C) Intersection of DRHs with ATAC/OQ. (D). Genome distributions of PQFS, ATAC/OQ, and DRH/ATAC/OQ. (E) Top 20 biological process GO terms for DRH/ATAC/OQ-containing genes.
Figure 18E:
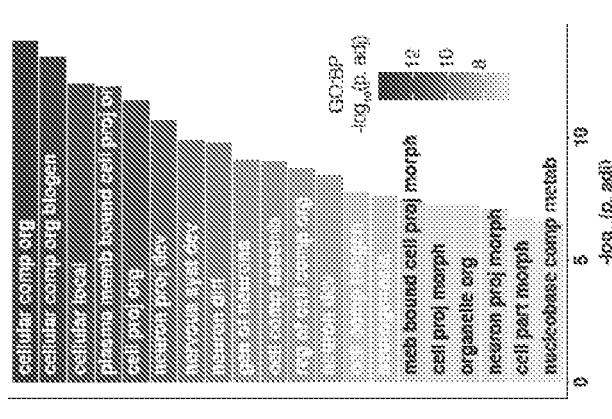
Figure 18A:
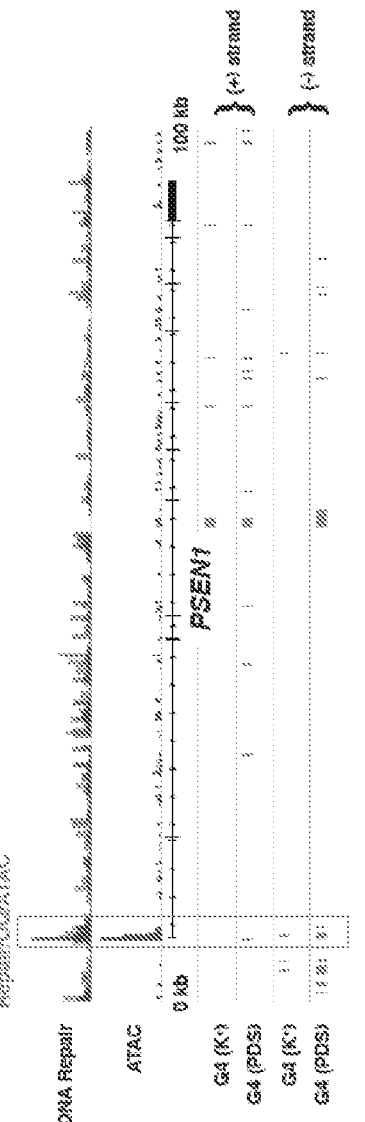
Figure 18D:
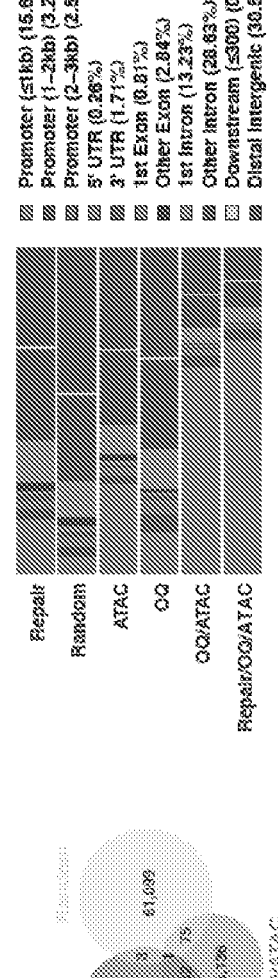
Figure 18C:
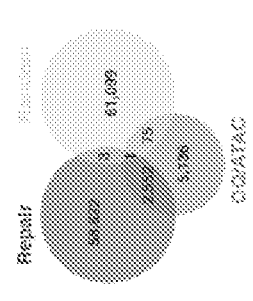

DNA G-quadruplexes (G4s)—knotted DNA secondary structures—can act as transcriptional modulators (Hansel-Hertsch et al., *Nat Genet* 48:1267-72, 2016). These structures have been suspected to be a source of genome instability in replicating cells, though their persistence in mammalian genomes indicates that there may be some utility to their formation. Locations of high confidence (OQs were defined as the intersection of both positive and negative strand OQs from G4-Seq K+ and K+PDS samples) observed quadruplex (OQ)-forming sequences from G4-Seq (Chambers et al., *Nat Biotechnol* 33:877-881, 2015; Hansel-Hertsch et al., *Nat Protoc* 13:551-564, 2018) were compared with regions defined as open by ATAC-Seq. 7,764 sites were identified that may form G4s in cortical neurons (FIGS. 18A-18B). Of these, 2,553 directly overlapped with DRHs, a ~34-fold enrichment over expected (FIG. S11C). These ATAC/OQs were largely located in the promoter≤1 kb of genes and likely represent sites of DNA repair of G4 structures (FIGS. 18D-18E). GO terms for these 2,114 genes were consistent with an enrichment for neuronal development and function (ex: PSEN1, FOS, BDNF, AUTS2).

Example 5

Figure 13B:
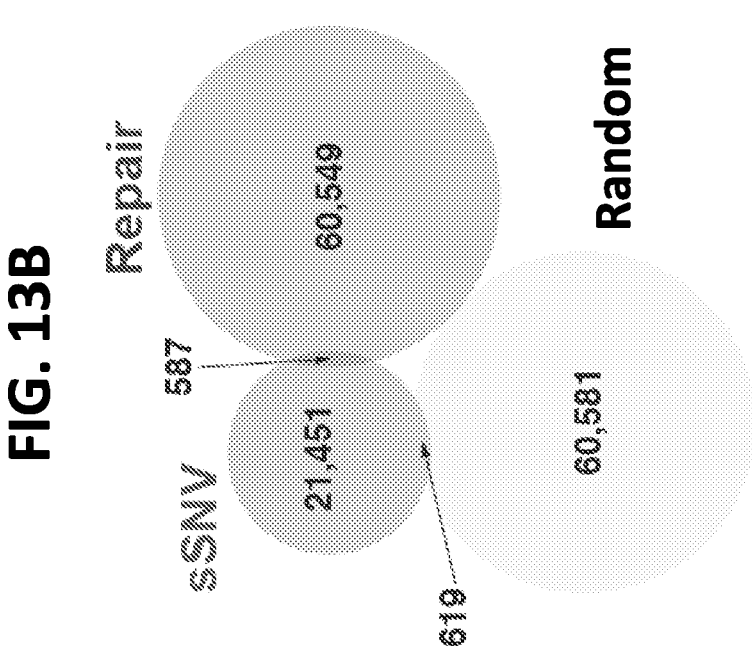
FIGS. 13A-13G. DNA repair hotspots correlate with key genomic regions. (A) Genomic distributions of DNA repair hotspots, random peaks, and sSNVs from human neurons. (B) Venn diagram for overlaps of Repair-Seq peaks with sSNVs and Random peaks with sSNVs. (C) Schematic for relative distance (reldist) function from bedtools. (D) Max GERP score for CEs, Repair-Seq peaks, ATAC-Seq peaks, Random peaks, and sSNVs. (E) Upset plot of intersections for CEs, Repair-Seq peaks, Random peaks, ATAC-Seq peaks, and sSNVs. (F) Interpeak distances for ATAC-Seq peaks, Repair-Seq peaks, Random peaks, and sSNVs normalized (bp*peaks/1e6). (G) Box plots for absolute distances for CE to Repair-Seq peaks, CE to ATAC-Seq peaks, CE to Random peaks, and CE to sSNVs. **** p-value<2e-16 by one-way ANOVA.
Figure 13A:
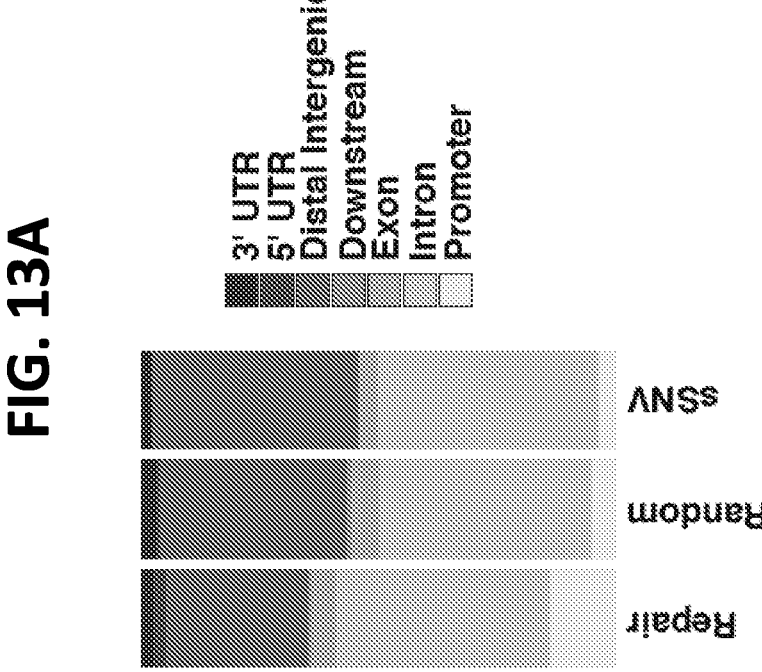

DNA Repair Hotspots Protect Evolutionarily Constrained Regions of the Human Genome from Epigenetic Drift As cells age, the activity of DNA repair mechanisms declines (Gorbunova et al., *Nucleic Acids Res* 35:7466-74, 2007), leading to an increase in genome instability in the form of information loss via somatic mutations and the accumulation of unrepaired lesions (Maynard et al., *Cold Spring Harb Perspect Med* 5, 2015). The locations of somatic single-nucleotide variants (sSNVs) (treated as a 500 base pair window around the called variant) identified from single neurons isolated from post-mortem humans were compared with the DRHs identified herein in ESC-iNs. It was found that they had negligible overlap (FIGS. 13A-13B). Relative distance comparison (a normalized metric that described the relative distances between each interval in a set compared with the two closest intervals of another set) for DRHs showed no proximal enrichment to sSNVs (FIGS. 14A, 13C), indicating mutations were occurring randomly throughout the genome, irrespective of repair efforts (Favorov et al., *PLoS Comput Biol* 8:e1002529, 2012).

Figures 13C, 13D:
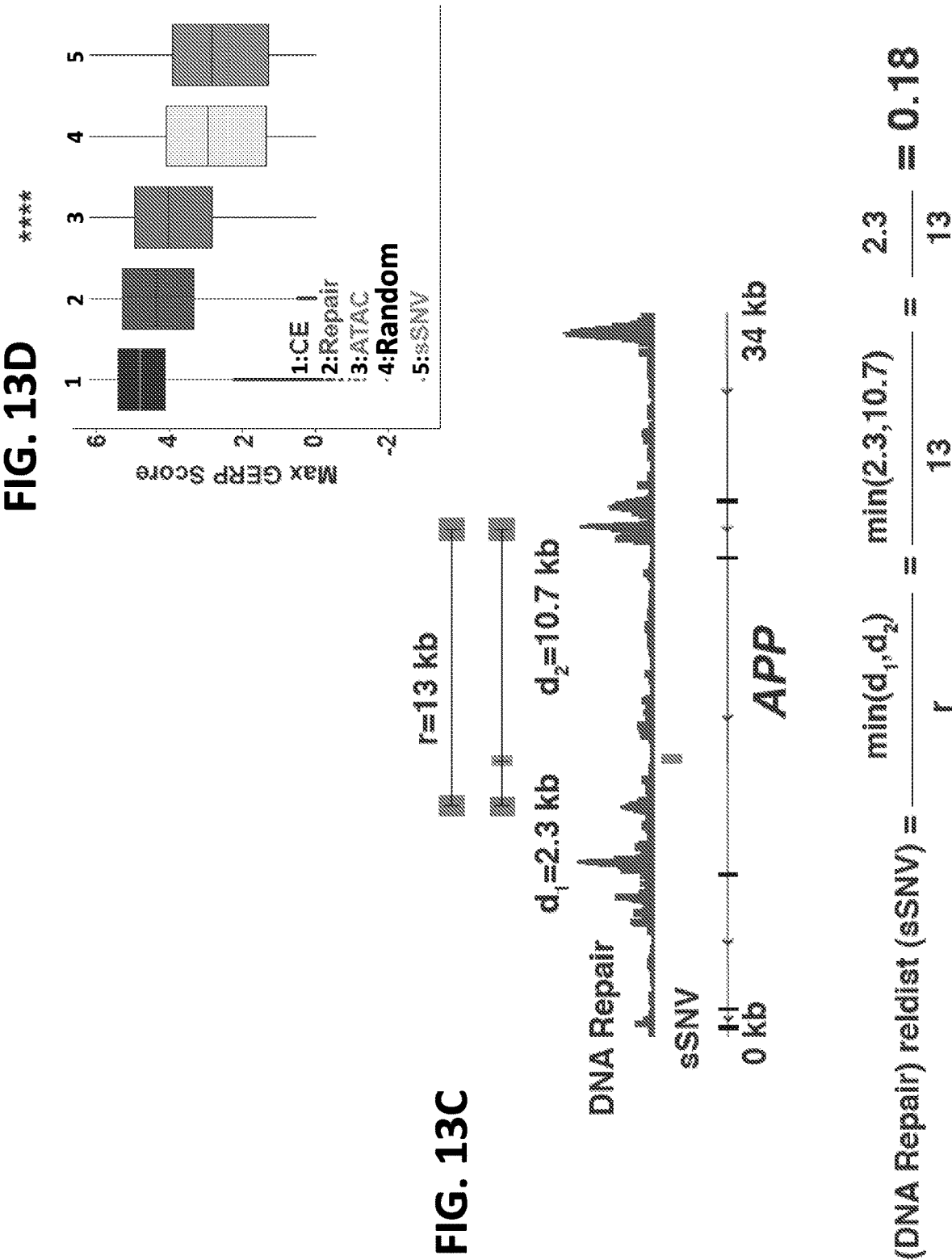
Figure 13E:
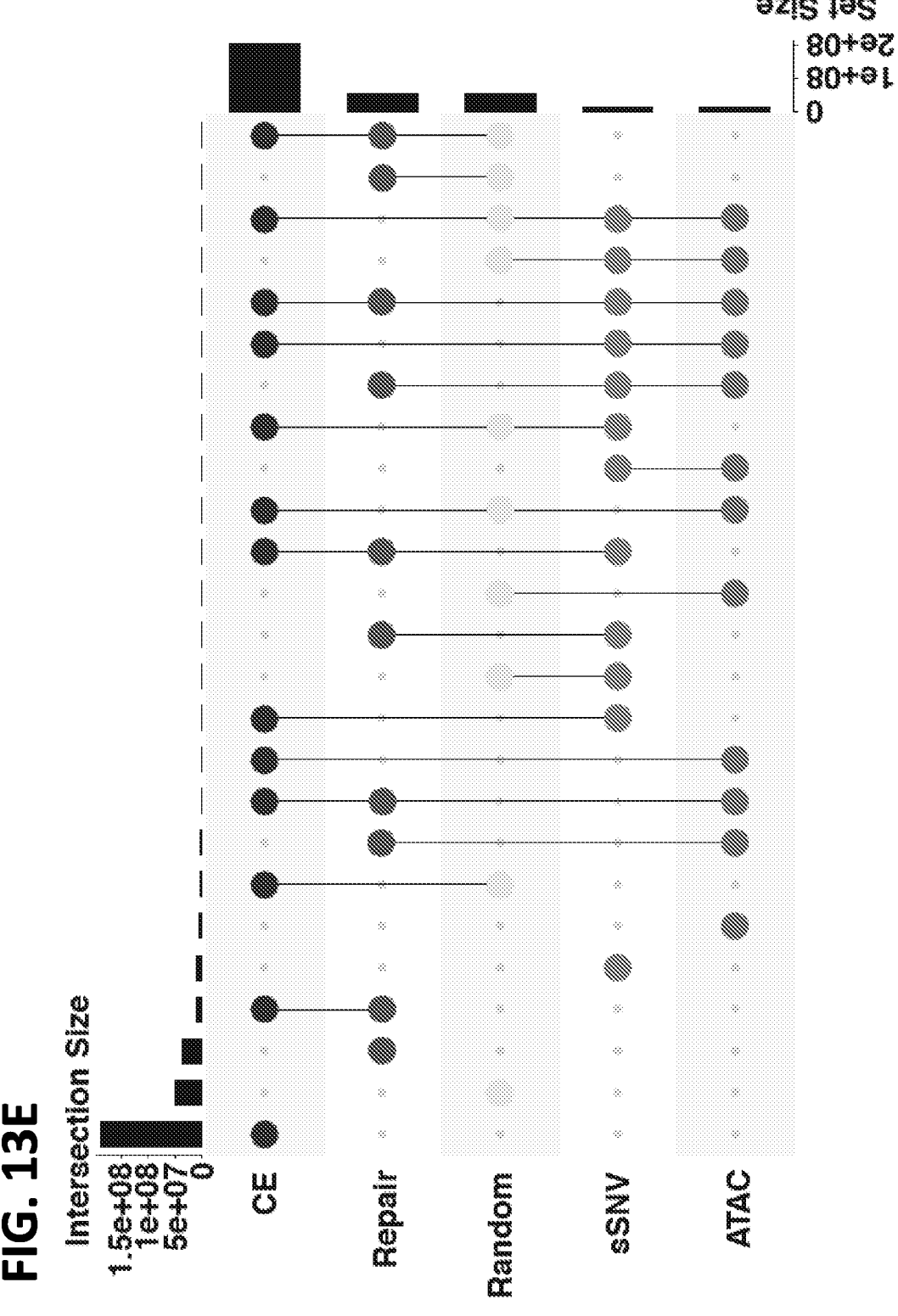
Figure 13F:
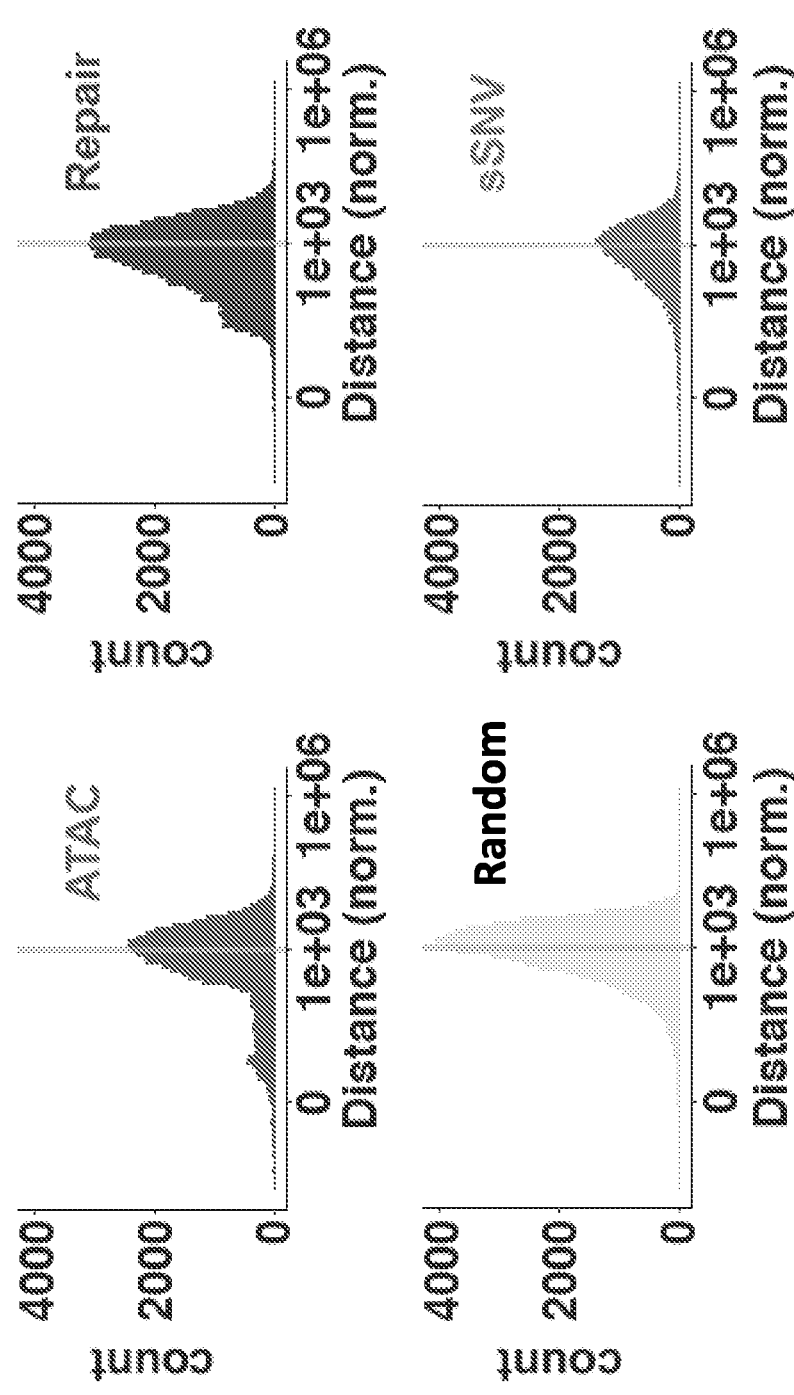
Figure 13G:
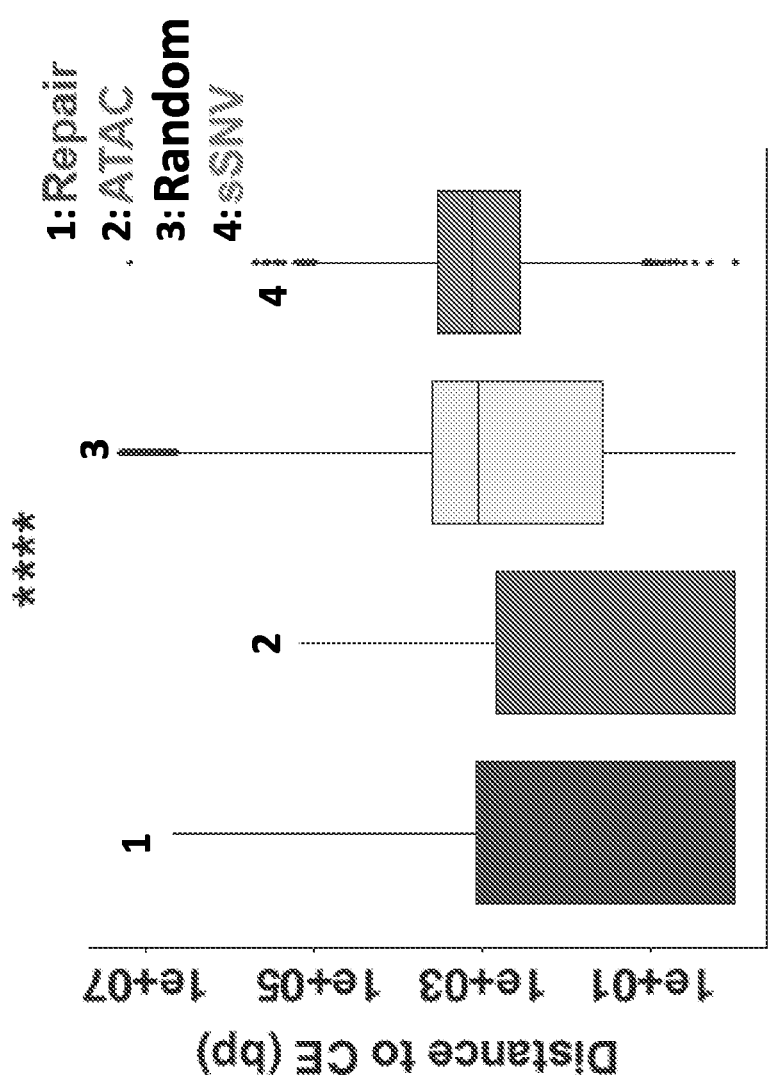
Figures 14A, 14B:
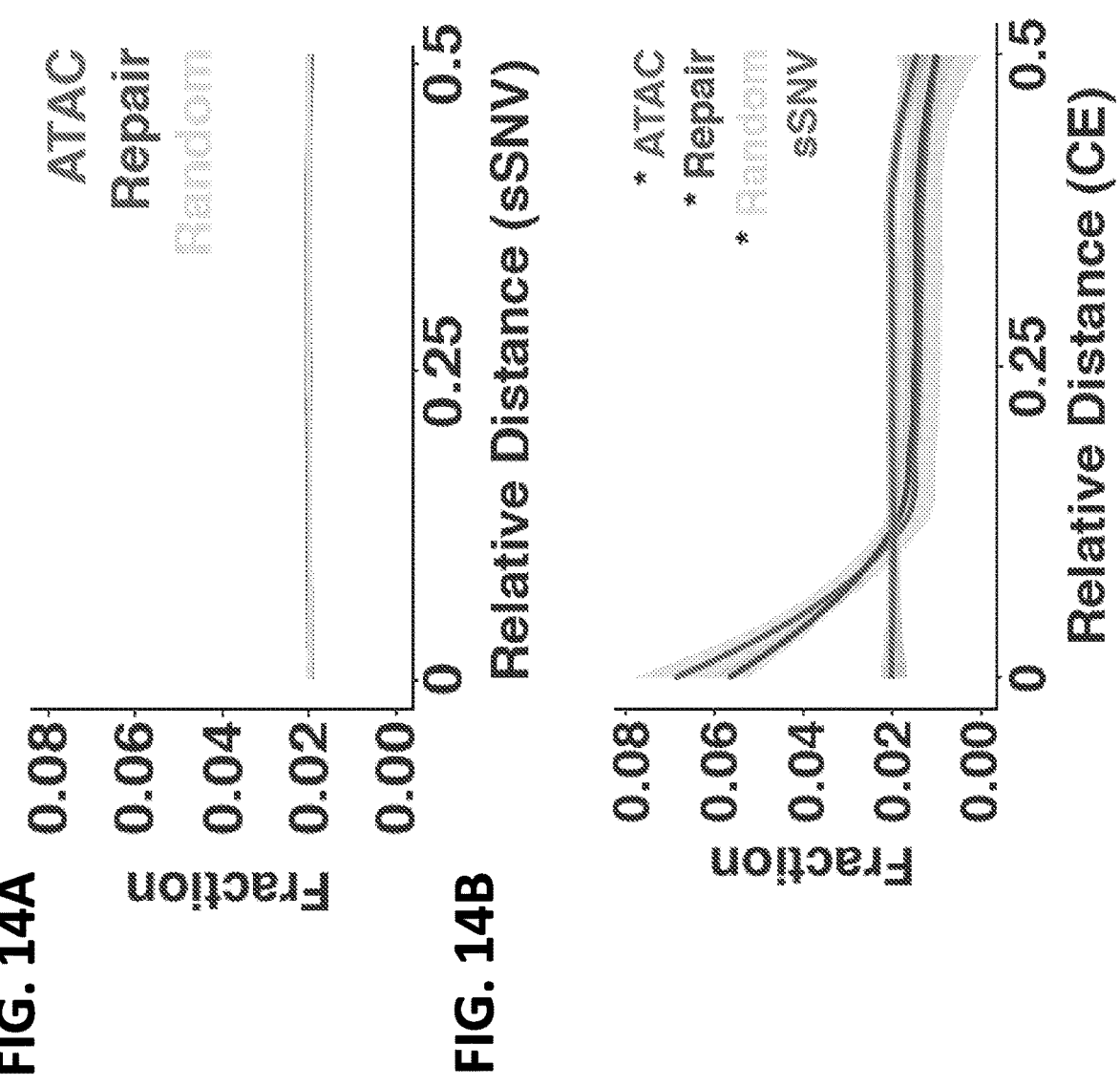
FIGS. 14A-14E. DNA repair hotspots protect evolutionarily constrained regions of the human genome from epigenetic drift. (A) Relative distance measurement from sSVNs identified from whole genome sequencing of single post-mortem human nuclei to nearest DRH or randomly placed peaks. (B) Relative distance measurement from GERP CE to nearest sSNV, DRH, ATAC-Seq peaks, or randomly placed peaks. (C) Representative browser view of DNA repair hotspots at baseline and 24 hrs after 10 min of 10 ng/mL NCS treatment demonstrates that peaks are lost and gained. (D) Volcano plot for NCS differential peaks using FDR<0.1 for DNA repair hotspots from 2 H1 and 2 H9 ESC-iNs samples. (E) Heat map of the stability (absolute fold change) of all DNA repair peaks in NCS-treated neurons compared with CG methylation changes from sorted human neurons. * p-value<0.01 by Jaccard distance test and **** p-value<2.47e-17 by hypergeometric test.

The relative value of the genetic information that these DRHs appeared to protect was determined. Evolutionary conservation based on the genomic evolutionary rate profiling (GERP) score was used as a proxy for the relative importance of the underlying sequence (Davydov et al., *PLoS Comput Biol* 6:e1001025, 2010). Intriguingly, DRHs often contained a single base pair under strong conservation, whereas randomly simulated peaks and sSVNs were more likely to be found at sites with negligible selective pressure (FIG. 13D).

The overlap of GERP-identified constrained elements (CEs) was compared to DRHs. Repair was more enriched near CEs than somatic mutations (FIGS. 13B, 13E-13G, 15) (genomic regions under selection to change little with evolution) (Davydov et al., *PLoS Comput Biol* 6:e1001025, 2010). These data indicate that DRHs protect essential elements from both erroneous repairs and potentially from going unrepaired.

Figures 16A, 16B, 16C, 16D, 16E:
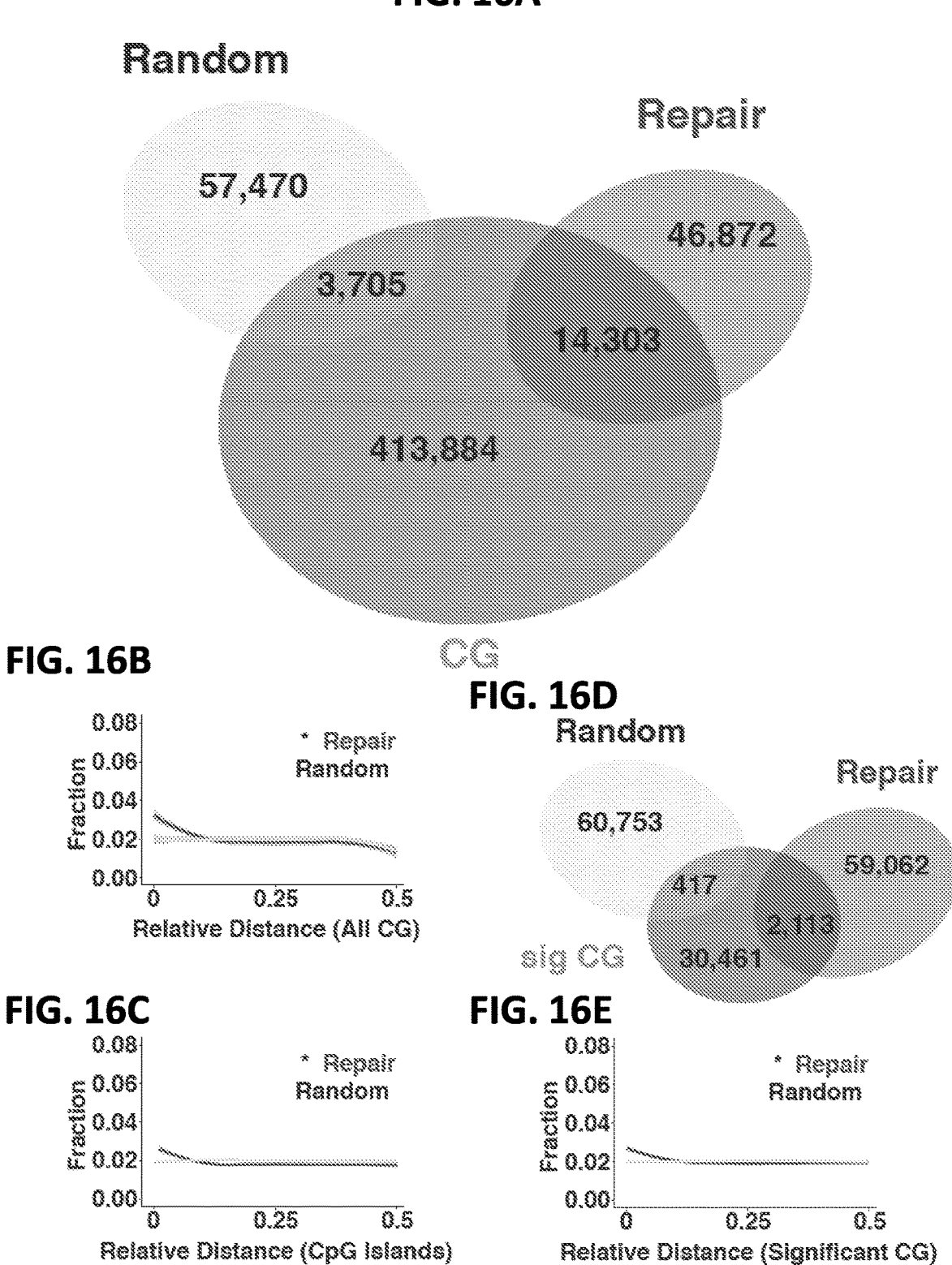
FIGS. 16A-16G. DNA damage and epigenetic drift. (A) Overlaps between CG dinucleotides on Illumina Infinium 450K methylation array, Repair-Seq peaks, and Random peaks. (B-C) Relative distance plot of Repair-Seq and Random peaks to CG dinucleotides from an Illumina Infinium 450K methylation array and CpG islands in the human genome. (D) Overlaps between CG dinucleotides that are significantly associated with methylation changes in aging human neurons and Repair-Seq or Random peaks. (E) Relative distance from significant CG dinucleotides to either Repair-Seq or Random peaks. (F) NCS peaks that are gained and lost largely at random when normalized to existing DRHs. (G) Relative distance measurement from NCS gained and lost sites to significant CG dinucleotides. * p-value<0.01 by Jaccard distance test.

Aging drives fundamental changes in the epigenome—epigenetic drift—which include alternation of chromatin marks and packaging, as well as changes directly to DNA methylation patterns (Lopez-Otin et al., *Cell* 153:1194-1217, 2013). Biological age is can be quantified with epigenetic clocks—changes in the methylation patterns on CG dinucleotides that are calibrated for specific cell and tissue types (Horvath, *Nat Rev Genet* 19, 371-384, 2018). Many thousand CG dinucleotides may have statistically significant methylation changes during aging; however, only a small subset of a few hundred are needed to accurately train a model for aging. Despite the accuracy of such models, no satisfying biological explanation exists as to why these DNA modifications are linked to aging (Horvath, *Nat Rev Genet* 19:371-384, 2018). The direct overlap of DRHs with CG dinucleotides from an Illumina Infinium 450K methylation array was compared and substantial overlap observed (FIG. 16A). The relative distance to CG dinucleotides and CpG islands is much closer to DRHs than random placed peaks (FIGS. 16B-16C). Using CG dinucleotides that exhibited methylation changes statistically associated with aging neurons from human prefrontal cortex (Kozlenkov et al., Genes (Basel) 8, (2017), some direct overlap with DRHs and a closer relative distance than random was observed (FIGS. 16D-16E).

Figures 14C, 14D, 14E:
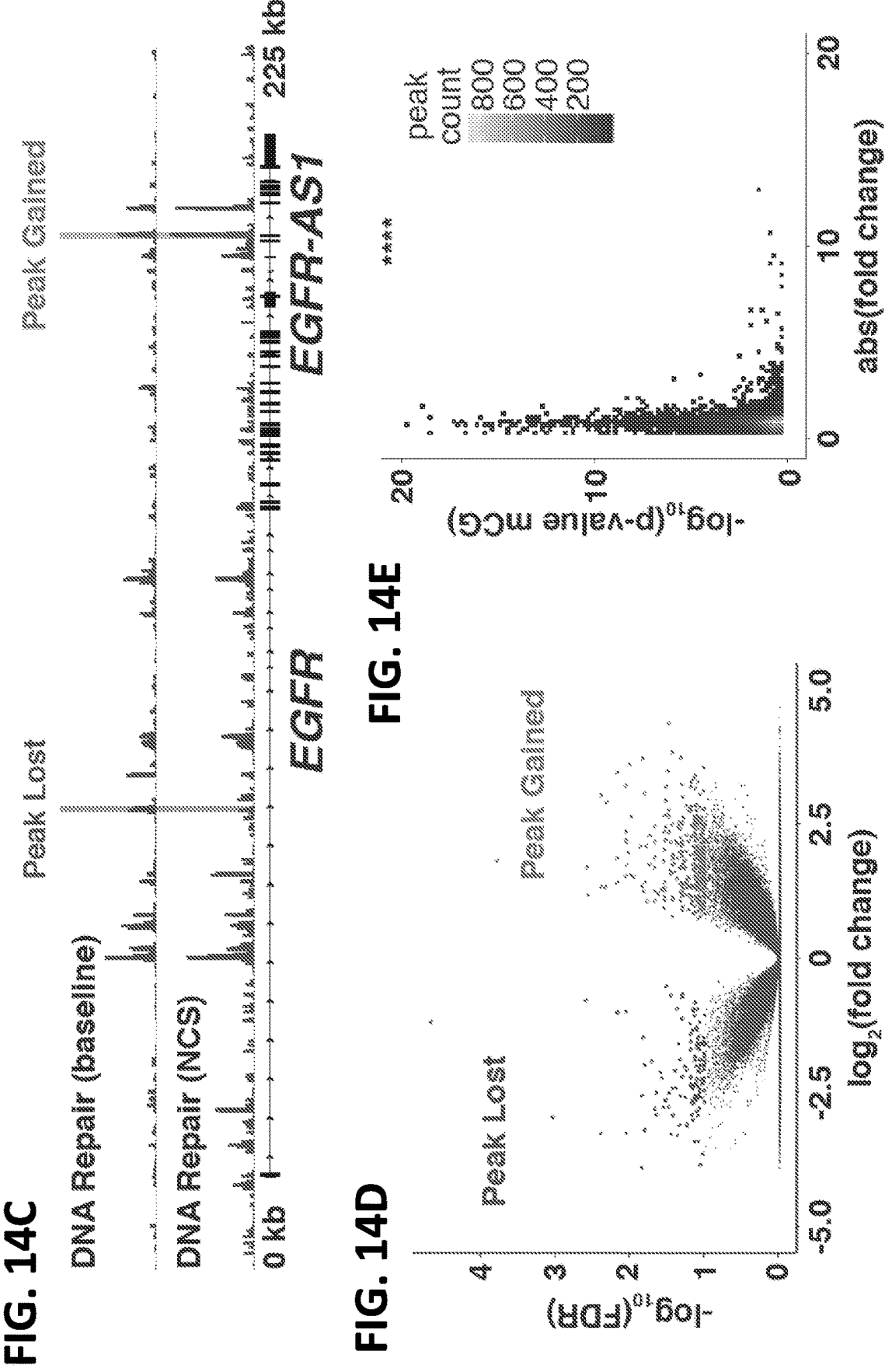
Figure 15:
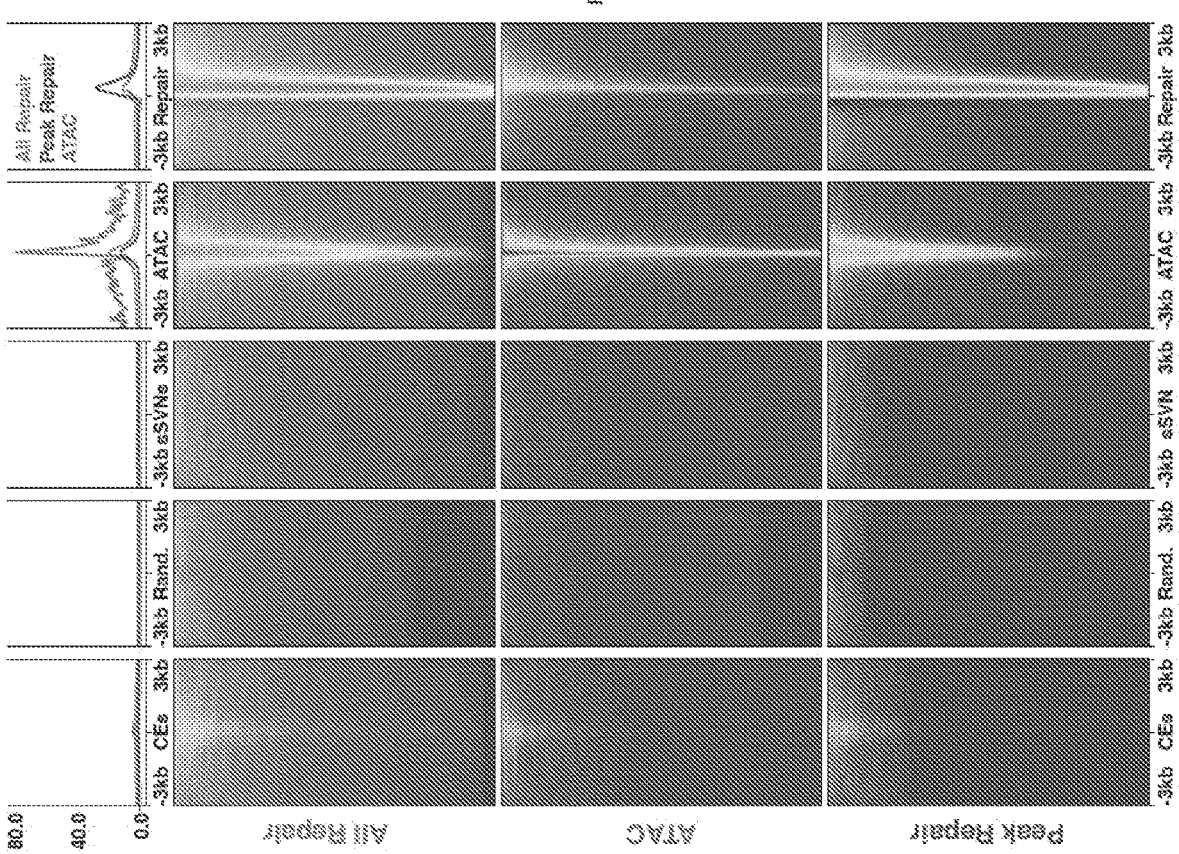
FIG. 15. Heatmaps for All Repair, Peak Repair, and ATAC-Seq. Heatmaps centered on CEs, Random peaks, sSNVs, ATAC-Seq peaks, and Repair-Seq peaks compared with all Repair-Seq reads, ATAC-Seq peaks, and Repair-Seq peaks.
Figures 16F, 16G:
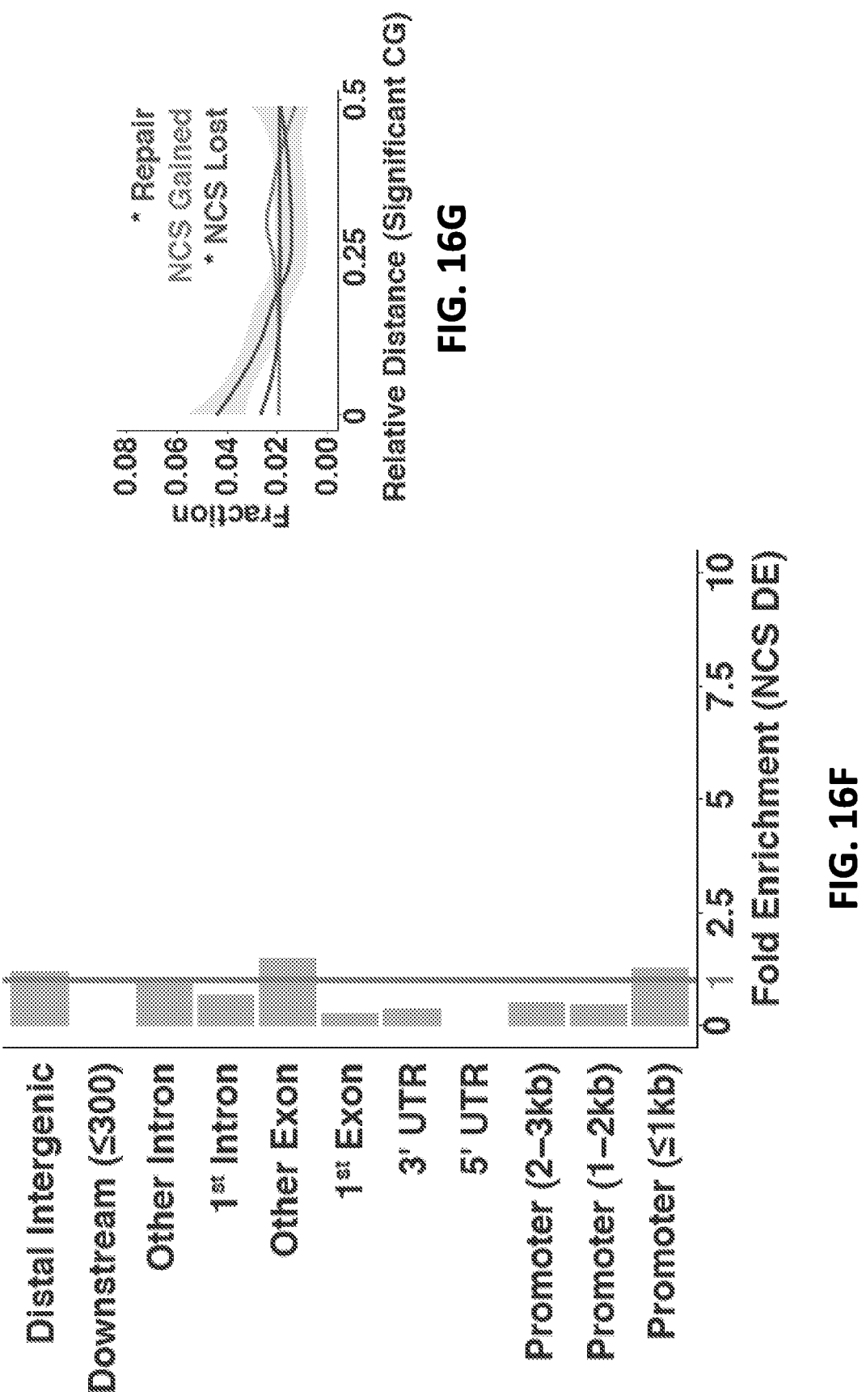

Genome instability in the form of DSBs is thought to be a primary driver of biological aging (White et al., *Nat Commun* 6:6790, 2015). Neurons were treated with the radiomimetic DNA damaging agent neocarzinostatin (NCS) to assay the changes to DRHs following injury. Acute NCS treatment triggered both the gain and loss of DRHs in neurons in a largely stochastic fashion, though at the dosage used relatively few peaks demonstrated consistent change (FIGS. 14C-14D, 16F).

In the context of aging, genome instability potentially redistributes repair efforts away from hotspots to other locations in the genome—similar to what is observed with NCS treatment (Van Meter et al., *Nat Commun* 5, 5011, 2014). Absolute fold change for NCS-treated samples was compared with statistically significant CG methylation sites and found that the most stable sites were those most likely to be associated with the epigenetic clock (FIGS. 14E, 16G). Therefore, as DNA repair capacity declines with age, these many of these sites might become less maintained as pathways become overtaxed, and subsequently more susceptible to changes in methylation status.

Incorporation of the click nucleoside analog EdU into the genome by repair polymerases provides a useful tool to visualize the locations of DNA repair in neurons as well as a means to isolate genome fragments and sequence their locations. These results demonstrate the existence of recurrent DRHs in post-mitotic neurons and indicate they play a key role in neuron identity and function. Repair-Seq can be a tool to explore how age and disease can disrupt genome integrity in the nervous system. In addition, the disclosed Repair-Seq methods can be used to analyze other cell types, such as other non-dividing cells. The identification of these sites in other cell types can further aid in the understanding of how age-related changes in their organization could drive differential aging or the development of disease in other tissue types.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of identifying DNA repair locations in a genome of a non-dividing cell, comprising:

incubating a non-dividing cell comprising genomic DNA (gDNA) with at least one reactive nucleoside analog under conditions that permit the at least one reactive nucleoside analog to be incorporated into the gDNA via a repair DNA polymerase of the non-dividing cell, thereby generating gDNA comprising the at least one reactive nucleoside analog;

obtaining gDNA comprising the at least one reactive nucleoside analog from the non-dividing cells;

generating a population of gDNA fragments, wherein the population of gDNA fragments comprises gDNA fragments comprising the at least one reactive nucleoside analog, and gDNA fragments that do not comprise the at least one reactive nucleoside analog;

isolating from the population of gDNA fragments those gDNA fragments comprising the at least one reactive nucleoside analog; and sequencing the isolated gDNA fragments comprising the at least one reactive nucleoside analog, thereby identifying DNA repair locations in the genome of the non-dividing cell.

2. The method of claim 1, wherein the non-dividing cell is a myocyte, astrocyte, microglia, adipocyte, neuron, skeletal muscle cell, cardiac muscle cell, keratinocytes, pancreatic islet cell, fibroblast, osteocyte, senescent cell, cancer stem cell, tissue resident macrophage, astrocyte, hepatocyte, T-cell, B-cell, oocyte, or quiescent stem cell.

3. The method of claim 2, wherein the non-dividing cell is a neuron obtained from a subject with a neurodegenerative disease.

4. The method of claim 3, wherein the neurodegenerative disease is Alzheimer's disease (AD), Parkinson's disease, Amyotrophic Lateral Sclerosis (ALS), Huntington's disease, Batten disease, or Frontotemporal Dementia.

5. The method of claim 2, wherein the non-dividing cell is obtained from a subject who has previously been administered a CRISPR/Cas therapy, wherein the CRISPR/Cas therapy comprises a guide RNA and a Cas protein or nucleic acid molecule encoding the Cas protein, and the method identifies off-target CRISPR/Cas gene editing.

6. The method of claim 3, wherein the subject has a genetic disorder.

7. The method of claim 1, wherein the at least one reactive nucleoside analog is a thymidine analog or a cytidine analog.

8. The method of claim 7, wherein the thymidine analog is 5-ethynyl-2'-deoxyuradine (EdU), 5-iodo-2'-deoxyuridine (IdU), 5-chloro-2'-deoxyuridine (CldU), or bromodeoxyuridine (BrdU).

9. The method of claim 7, wherein the cytidine analog is 5-ethynyl-2'-deoxycytidine (EdC).

10. The method of claim 1, wherein the incubating comprises incubating the non-dividing cell with the at least one reactive nucleoside analog for at least 12 hours, or at least 24 hours.

11. The method of claim 1, wherein generating the population of gDNA fragments comprises shearing the gDNA comprising the at least one reactive nucleoside analog or sonicating the gDNA comprising the at least one reactive nucleoside analog.

12. The method of claim 1, wherein the isolating comprises:

contacting the population of gDNA fragments with a reporter molecule conjugated to a molecule that can bind to a solid support, thereby conjugating the reporter molecule to the at least one reactive nucleoside analog;

contacting the population of gDNA fragments with the solid support, wherein gDNA fragments comprising the at least one reactive nucleoside analog bind to the solid support; and removing gDNA fragments not comprising the at least one reactive nucleoside analog.

13. The method of claim 1, wherein the isolating comprises:

denaturing the population of gDNA fragments into single-stranded (ss) gDNA fragments;

contacting the population of ssgDNA fragments with an antibody specific for the at least one reactive nucleoside analog, under conditions that allow the antibody to bind to the at least one reactive nucleoside analog, wherein the antibody is attached to a solid support; and separating ssgDNA fragments bound to the antibody and solid support, away from ssgDNA fragments not bound to the antibody and solid support.

14. The method of claim 1, wherein sequencing comprises next generation sequencing.

15. The method of claim 1, wherein the method further comprises incorporating molecular bar codes to a 5'-end, 3'-end, or both ends, of the population of gDNA fragments or the isolated gDNA fragments comprising the at least one reactive nucleoside analog.

16. The method of claim 1, wherein the method further comprises amplifying the isolated gDNA fragments comprising the at least one reactive nucleoside analog.

17. The method of claim 1, wherein the method further comprises aligning the sequenced isolated gDNA comprising the at least one reactive nucleoside analog to a reference genome.

18. The method of claim 17, wherein the non-dividing cell is a human cell and the reference genome is a human reference genome.

19. The method of claim 1, wherein the method further comprises incubating the non-dividing cell with one or more test agents before or during the incubating with the at least one reactive nucleoside analog, and the method determines if the one or more test agents can increase or decrease DNA repair as compared to an amount of DNA repair without the one or more test agents.

20. The method of claim 1, wherein the non-dividing cells are obtained from a subject previously treated with chemotherapy.

* * * * *